(12) United States Patent
Blakemore et al.

(10) Patent No.: US 10,662,477 B2
(45) Date of Patent: May 26, 2020

(54) BIOMARKERS AND METHODS TO PREDICT RESPONSE TO INHIBITORS AND USES THEREOF

(71) Applicant: Millennium Pharmaceuticals, Inc., Cambridge, MA (US)

(72) Inventors: Stephen J. Blakemore, Littleton, MA (US); Bin Li, Belmont, MA (US); Hyunjin Shin, Brookline, MA (US); William L. Trepicchio, Andover, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 821 days.

(21) Appl. No.: 14/432,587

(22) PCT Filed: Oct. 1, 2013

(86) PCT No.: PCT/US2013/062902
§ 371 (c)(1),
(2) Date: Mar. 31, 2015

(87) PCT Pub. No.: WO2014/055543
PCT Pub. Date: Apr. 10, 2014

(65) Prior Publication Data
US 2015/0240315 A1  Aug. 27, 2015

Related U.S. Application Data

(60) Provisional application No. 61/708,349, filed on Oct. 1, 2012.

(51) Int. Cl.
*G01N 33/48* (2006.01)
*C12Q 1/6886* (2018.01)
*G16B 5/00* (2019.01)
*C12Q 1/6834* (2018.01)
*A61K 31/519* (2006.01)
*G06F 17/18* (2006.01)

(52) U.S. Cl.
CPC .......... *C12Q 1/6886* (2013.01); *A61K 31/519* (2013.01); *C12Q 1/6834* (2013.01); *G06F 17/18* (2013.01); *G16B 5/00* (2019.02); *C12Q 2600/106* (2013.01); *C12Q 2600/112* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS 9,827,246 B2  11/2017  Blakemore et al.
2008/0026385 A1  1/2008  Sharma et al.
2010/0227838 A1*  9/2010  Shah .................. A61K 31/454
                                                        514/89
2011/0081362 A1  4/2011  Elledge et al.
2011/0118298 A1*  5/2011  Fritz ................. G01N 33/57492
                                                        514/291
2011/0287974 A1  11/2011  Benvenisty et al.
2012/0010230 A1*  1/2012  MacDougall ...... A61K 31/4355
                                                        514/278
2012/0041683 A1*  2/2012  Vaske .................... G06F 19/12
                                                        702/19
2012/0214829 A1  8/2012  Spellman et al.
2017/0105995 A1  4/2017  Benes et al.

FOREIGN PATENT DOCUMENTS

CN        101027410 A    8/2007
CN        102459638 A    5/2012
WO    WO 2010/132110 A1  11/2010
WO    WO 2011/130402 A2  10/2011
WO    WO 2013/063481 A1   5/2013

OTHER PUBLICATIONS

Liao et al. "Quantitative proteomic analysis of cellular protein modulation upon inhibition of the NEDD8-activating enzyme by MLN4924." Molecular & Cellular Proteomics 10, No. 11 (2011): M111-009183.*
Soucy, Teresa A., et al. "An inhibitor of NEDD8-activating enzyme as a new approach to treat cancer." Nature, vol. 458 (2009) pp. 732-736.*
Luo, Zhongguang, et al. "The Nedd8-activating enzyme inhibitor MLN4924 induces autophagy and apoptosis to suppress liver cancer cell growth." Cancer research (2012) canres-0388.*
Nawrocki, Steffan T., et al. "MLN4924: a novel first-in-class inhibitor of NEDD8-activating enzyme for cancer therapy." Expert opinion on investigational drugs 21.10 (2012): 1563-1573.*
Bignell, G. R. et al. , "Signatures of mutation and selection in the cancer genome," *Nature*, vol. 463: 893-898, Macmillan Ltd., United Kingdom, 2010.
Guihard, S. et al., "The NEDD8 conjugation pathway regulates p53 transcriptional activity and head and neck cancer cell sensitivity to ionizing radiation," *International Journal of Oncology*, vol. 41: 1531-1540, 2012.
Li, B. et al., "Investigation of efficacy of the NAE inhibitor MLN4924 across large-scale cell line panels, reveals potentially sensitive cancer indications and candidate predictive biomarkers," *Mol. Cancer Ther.*, vol. 10(11): Abstract A45, 2011.
Liao, H. et al., "Quantitative Proteomic Analysis of Cellular Protein Modulation upon Inhibition of the NEDD8-Activating Enzyme by MLN4924," *Mol. & Cell Proteomics*, vol. 10(11), 2011.

(Continued)

*Primary Examiner* — Anna Skibinsky
(74) *Attorney, Agent, or Firm* — Sterne, Kessler, Goldstein and Fox P.L.L.C.

(57) ABSTRACT

Disclosed herein are markers associated with sensitivity to treatment with therapeutic agents. Methods to identify markers for predicting outcome to treatment with a therapeutic agent are disclosed as well as methods to predict outcome of treatment using markers. Compositions and methods are provided to predict response to NAE inhibition or EGFR inhibition treatment.

Figure 1A:
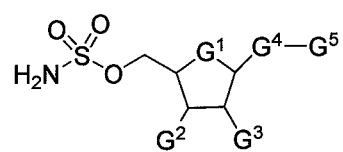

26 Claims, 13 Drawing Sheets
Specification includes a Sequence Listing.

(56) References Cited

OTHER PUBLICATIONS

Luo, Z. et al., "Inactivation of the Cullin (CUL)-RING E3 ligase by the NEDD8-activating enzyme inhibitor MLN4924 triggers protective autophagy in cancer cells," *Autophagy*, vol. 8(11), 1677-1679, 2012.

Mackintosh, C. et al., "WEE1 accumulation and deregulation of S-phase proteins mediate MLN4924 potent inhibitory effect on Ewing sarcoma cells," *Oncogene*, vol. 32: 1-11, 2012.

Milhollen, M. A. et al., "MLN4924, a NEDD8-activating enzyme inhibitor, is active in diffuse large B-cell lymphoma models: rationale for treatment of NF-κB-dependent lymphoma," *Blood*, vol. 116(9): 1515-1523, 2010.

Milhollen, M. A. et al., "Treatment-Emergent Mutations in NAEβ Confer Resistance to the NEDD8-Activating Enzyme Inhibitor MLN4924," *Cancer Cell*, vol. 21: 388-401, Elsevier Inc., United States, 2012.

Narwocki, S. T. et al., "MLN4924: a novel first-in-class inhibitor of NEDD8-activating enzyme for cancer therapy," *Expert Opinion on Investigational Drugs*, vol. 21(10): 1563-1573, 2012.

Soucy, T.A. et al., "The NEDD8 Conjugation Pathway and Its Relevance in Cancer Biology and Therapy," *Genes & Cancer*, vol. 1(7): 708-716, 2010.

Tanaka, T. et al., "Inhibition of NEDD8-conjugation pathway by novel molecules: Potential approaches to anticancer therapy," *Mol. Onc.*, vol. 6: 267-275, Elsevier B.V., Netherlands, 2012.

Toth, J. I. et al., "A Gatekeeper Residue for NEDD8-Activating Enzyme Inhibition by MLN4924," *Cell Reports*, vol. (1): 309-316, 2012.

Wei, D. et al., "Radiosensitization of Human Pancreative Cancer Cells by MLN4924, an Investigational NEDD8-Activating Enzyme Inhibitor," *Cancer Res.*, vol. 72(1): 282-293, 2012.

Watson, I. R., et al., "NEDD8 Pathways in Cancer, Sine Quibus Non," *Cancer Cell*, vol. 19: 168-176, 2011.

Soucy, T. A., et al., "An inhibitor of NEDD8-activating enzyme as a new approach to treat cancer," *Nature*, vol. 458: 732-737, 2009.

Shin, Y.J. et al., "The role of EZH2 in the regulation of the activity of matrix metalloproteinases in prostate cancer cells," PLOS ONE 7(1): e30393, Public Library of Science, United States (2012).

\* cited by examiner

A.

B.

A.

B.

C.

D.

A.

B.

BIOMARKERS AND METHODS TO PREDICT RESPONSE TO INHIBITORS AND USES THEREOF

RELATED APPLICATIONS

This application claims priority to U.S. Provisional Application No. 61/708,349 filed on Oct. 1, 2012. The entire contents of the foregoing application are incorporated herein by reference.

SEQUENCE LISTING

The contents of the Sequence Listing are submitted herewith in electronically readable format. The Sequence Listing file was created on Oct. 1, 2013, is named "sequencelisting.txt," and its size is 1160 kb (1,223,135 bytes). The entire contents of the Sequence Listing in the sequencelisting.txt file are incorporated herein by this reference.

BACKGROUND

Cells become cancerous when their genotype or phenotype alters in a way that there is uncontrolled growth which is not subject to the confines of the normal tissue environment. One or more genes is mutated, amplified, deleted, overexpressed or underexpressed. Chromosome portions can be lost or moved from one location to another. Some cancers have characteristic patterns by which genotypes or phenotypes are altered.

A variety of agents treat cancers. Cancers of the blood and bone marrow often are treated with steroids/glucocorticoids, imids, proteasome inhibitors and alkylating agents. Cancers of other tissues often are treated with alkylating agents, topoisomerase inhibitors, kinase inhibitors, microtubule inhibitors, angiogenesis inhibitors or other agents.

One of the continued problems with therapy in cancer patients is individual differences in response to therapies. Some patients respond to one therapy better than another, presenting the potential for a patient to follow multiple therapeutic routes to effective therapy. With the narrow therapeutic index and the toxic potential of many available cancer therapies, such differential responses potentially contribute to patients undergoing unnecessary, ineffective and even potentially harmful therapy regimens. If a designed therapy could be optimized to treat individual patients, such situations could be reduced or even eliminated and there may be more focused, successful patient therapy overall.

SUMMARY

The present disclosure relates to prognosis and planning for disease treatment by identifying and using markers and marker sets for testing diseased cells or tissues to enable determination of the benefit of a particular treatment to a patient. Provided herein are biomarkers, compositions and methods that predict response to treatment with an agent, evaluate the resistance or sensitivity of diseases to targeted therapeutic agents prior to the initiation of therapeutic regimen and monitor the effectiveness of the therapeutic regimen. Further provided are therapeutic methods which incorporate steps of quantifying aspects of the markers and marker sets in diseased cells and modeling the quantities for determining the behavior of the disease upon treatment.

In one aspect, the invention provides measurement of the amount or presence of markers provided herein. For example, the compositions and methods provided herein can be used to determine outcome of treatment with an agent, such as a NEDD8-activating enzyme (NAE) inhibitor, such as a 1-substituted methyl sulfamate, such as MLN4924, an epidermal growth factor receptor (EGFR) inhibitor, such as a tyrosine kinase inhibitor (such as erlotinib) or a pan-kinase inhibitor, such as sorafenib: whether a patient will be responsive or non-responsive, whether enhanced survival time can be expected by treatment, or whether an alternative therapy to and/or a more aggressive therapy may enhance expected survival time. Furthermore the compositions and methods provided herein can be used to determine whether a patient will be responsive or non-responsive to an agent or a long term or short term survivor after administration of the agent. In some examples, the methods and compositions can determine whether an NAE inhibitor, EGFR inhibitor or pan-kinase inhibitor will or will not be effective in stopping or slowing tumor growth, can determine whether a an NAE inhibitor, EGFR inhibitor or pan-kinase inhibitor therapy regimen will or will not be effective to enhance patient survival time, can monitor the effectiveness of an NAE inhibitor, EGFR inhibitor or pan-kinase inhibitor used for the treatment of tumors, can be included in treatments of tumors comprising NAE inhibitor, EGFR inhibitor or pan-kinase inhibitor therapy; and can identify specific therapeutic agents or combinations of therapeutic agents that are effective for the treatment of tumors in specific patients.

In one embodiment, the markers are predictive of whether there will be a favorable outcome (e.g., good response, long time-to-progression, and/or long term survival) after treatment with a NEDD8-activating enzyme (NAE) inhibitor, such as a 1-substituted methyl sulfamate. Testing samples comprising tumor cells to determine the presence or amounts of markers or expression profile of a marker set identifies particular patients who are expected to have a favorable outcome with treatment, e.g., with an NAE inhibitor, such as a 1-substituted methyl sulfamate, and whose disease may be managed by standard or less aggressive treatment, as well as those patients who are expected have an unfavorable outcome with the treatment and may require an alternative treatment to, a combination of treatments and/or more aggressive treatment with an NAE inhibitor to ensure a favorable outcome and/or successful management of the disease.

In one aspect, the invention provides kits useful in determination of characteristics, e.g., amounts or presence of the markers. In another aspect, the invention provides methods for determining prognosis and treatment or disease management strategies. In these aspects, the characteristic, e.g., presence or amount of marker or expression profile of a marker set in a sample comprising tumor cells is measured. In one embodiment, the tumor is a liquid, e.g., hematological tumor, e.g., acute myelogenous leukemia, myelodysplastic syndrome or multiple myeloma. In another embodiment, the tumor is a solid tumor, e.g., melanoma, non-small cell lung cancer, esophageal cancer, bladder cancer, neuroblastoma cancer, mesothelioma, or pancreatic cancer. In another embodiment, the tumor is in lung cancer and metastases therefrom, e.g., in the brain, pancreatic cancer or breast cancer.

In various embodiments, the characteristic, e.g., composition or amount of DNA, the composition or amount of RNA and/or the composition or amount of protein corresponding to a marker gene or marker set, described herein is measured. Useful information leading to the prognosis or treatment or disease management strategies is obtained when assays reveal information about a marker gene, e.g., whether the RNA or protein amount of a marker gene or genes indicates overexpression or underexpression. In one embodiment, the strategy is determined for E1 enzyme inhibition, e.g., NAE inhibition, e.g., MLN4924, therapy. In another embodiment, the strategy is determined for EGFR inhibition, e.g., tyrosine kinase inhibition, e.g., erlotinib therapy. In another embodiment, the strategy is determined for the pan-kinase, e.g., multiple tyrosine kinase inhibition, e.g., sorafenib therapy.

A marker gene useful to test for determination of prognosis or treatment or disease management strategy and whose expression correlates with the response to an agent is selected from the group consisting of markers identified in Table 1, Table 2 and Table 3. A marker gene set whose expression profile correlates with the response to an agent can comprise one or more markers identified in Table 1, Table 2 and Table 3. By examining the characteristic, e.g., expression of one or more of the identified markers or marker sets in a diseased tissue, e.g., tumor, it is possible to determine which therapeutic agent or combination of agents will be most likely to inhibit disease activity, e.g., reduce the growth rate of the cancer cells. By examining the expression of one or more of the identified markers or marker sets in a cancer, it is also possible to determine which therapeutic agent or combination of agents is less likely to reduce the growth rate of cancer cells. By examining the expression of one or more of the identified markers or marker sets, it is therefore possible to eliminate ineffective or inappropriate therapeutic agents. These determinations can be made on a patient by patient basis or on an agent by agent basis. Thus, one can determine whether or not a particular therapeutic regimen is likely to benefit a particular patient or type of patient, and/or whether a particular regimen should be started, continued, discontinued, altered or avoided. In some embodiments, a marker has a DNA, an RNA and/or protein characteristic, e.g., composition or amount, e.g., in a sample comprising tumor cells, which is different than a normal DNA, RNA and/or protein, e.g., it is upregulated.

The present invention is directed to methods of identifying and/or selecting a patient, e.g., cancer patient, e.g., someone afflicted with a hematologic malignancy or a solid tumor, such as melanoma, esophageal cancer, bladder cancer, lung cancer, pancreatic cancer or breast cancer, who is expected to demonstrate a favorable outcome upon administration of a therapeutic regimen, e.g., a therapeutic regimen comprising an NAE inhibitor, such as a 1-substituted methyl sulfamate treatment, an EGFR inhibitor, such as erlotinib, or a pan-kinase inhibitor, such as sorafenib. Additionally provided are methods of identifying a patient who is expected to have an unfavorable outcome upon administration of such a therapeutic regimen. These methods typically include measuring, determining, receiving, storing or transmitting information about the characteristic, e.g., composition or amount of one or more marker gene(s) in a patient's tumor (e.g., a patient's cancer cells, e.g., hematological cancer cells or solid tumor cells), and in a further embodiment, identifying or advising whether result from the sample corresponds to a favorable outcome of a treatment regimen, e.g., using an NAE inhibitor, such as a 1-substituted methyl sulfamate treatment regimen, using an EGFR inhibitor, such as an erlotinib treatment regimen or using a pan-kinase inhibitor, such as sorafenib treatment regimen.

Additionally provided methods include therapeutic methods which further include the step of beginning, continuing, or commencing a therapy accordingly where the characteristic, e.g., composition or amount of a patient's marker gene or markers in a marker gene set indicates that the patient is expected to demonstrate a favorable outcome with the therapy, e.g., using an NAE inhibitor, such as a 1-substituted methyl sulfamate therapeutic regimen, using an EGFR inhibitor, such as an erlotinib treatment regimen or using a pan-kinase inhibitor, such as a sorafenib treatment regimen. In addition, the methods include therapeutic methods which further include the step of stopping, discontinuing, altering or halting a therapy accordingly where the presence of a mutation in a marker gene or the characteristic, e.g., composition or amount of a patient's marker indicates that the patient is expected to demonstrate an unfavorable outcome with the treatment, e.g., with the NAE inhibitor, such as a 1-substituted methyl sulfamate treatment regimen, with an EGFR inhibitor, such as an erlotinib treatment regimen or with a pan-kinase inhibitor, such as a sorafenib treatment regimen, e.g., as compared to a patient identified as having a favorable outcome receiving the same therapeutic regimen. In another aspect, methods are provided for analysis of a patient not yet being treated with a therapy, e.g., an NAE inhibitor, such as a 1-substituted methyl sulfamate therapy, an EGFR inhibitor, such as erlotinib therapy or a pan-kinase inhibitor, such as sorafenib therapy and identification and prediction of treatment outcome based upon the characteristic, e.g., composition or amount of one or more of a patient's marker gene or marker genes described herein. Such methods can include not being treated with the therapy, e.g., NAE inhibitor, such as a 1-substituted methyl sulfamate therapy, EGFR inhibitor, such as erlotinib therapy or pan-kinase inhibitor, such as sorafenib therapy. Such methods can include being treated with therapy, e.g., NAE inhibitor, such as a 1-substituted methyl sulfamate therapy, EGFR inhibitor, such as erlotinib therapy or pan-kinase inhibitor, such as sorafenib therapy, in combination with one more additional therapies. Such methods can include being treated with an alternative therapy to an NAE inhibitor, such as a 1-substituted methyl sulfamate, EGFR inhibitor, such as erlotinib therapy or pan-kinase inhibitor, such as sorafenib therapy, or being treated with a more aggressive dosing and/or administration regimen of a therapy, e.g., E1 enzyme inhibitor, such as an NAE inhibitor, an EGFR inhibitor, such as erlotinib or a pan-kinase inhibitor, such as sorafenib, e.g., as compared to the dosing and/or administration regimen of a patient identified as having a favorable outcome to standard NAE inhibitor, such as a 1-substituted methyl sulfamate therapy, standard EGFR inhibitor, such as erlotinib therapy, or standard pan-kinase inhibitor, such as sorafenib therapy. Thus, the provided methods of the invention can eliminate ineffective or inappropriate use of therapy, e.g., NAE inhibitor, such as 1-substituted methyl sulfamate therapy, EGFR inhibitor, such as erlotinib therapy, or pan-kinase inhibitor, such as sorafenib therapy.

Additionally provided are marker sets which can be used to develop a diagnostic test or a readable array useful for identifying patients who will be responsive or non-responsive to NAE inhibitor therapy, EGFR inhibitor therapy or pan-kinase inhibitor therapy. Probes or peptides identified in a marker set of the invention can be included in a diagnostic or prognostic test to select a therapy, e.g., NAE inhibitor therapy, EGFR inhibitor therapy or pan-kinase inhibitor therapy or a test which is used to determine continuation of therapy, e.g., NAE inhibitor, EGFR inhibitor therapy or pan-kinase inhibitor therapy.

Additional methods include methods to determine the activity of an agent, the efficacy of an agent, or identify new therapeutic agents or combinations. Such methods include methods to identify an agent as useful, e.g., as an NAE inhibitor, such as a 1-substituted methyl sulfamate, for treating a cancer, e.g., a hematological cancer (e.g., multiple myeloma, leukemias, lymphoma, etc) or solid tumor cancer (e.g., melanoma, esophageal cancer or bladder cancer), based on its ability to affect the characteristic, e.g., composition or amount of a marker or markers of the invention. Other methods include methods to identify an agent as useful, e.g., as an EGFR inhibitor, such as erlotinib, for treating a cancer, e.g., lung cancer, such as non-small cell lung cancer (NSCLC), adenocarcinoma of the lung, or lung metastases in the brain, pancreatic cancer or breast cancer, based on its ability to affect the characteristic, e.g., composition or amount of a marker or markers of the invention. Other methods include methods to identify an agent as useful, e.g., as a pan-kinase inhibitor, such as sorafenib, for treating a cancer, e.g., kidney cancer, liver cancer or thyroid cancer, based on its ability to affect the characteristic, e.g., composition or amount of a marker or markers of the invention. For example, an inhibitor which decreases or increases the characteristic, e.g., composition or amount of a marker or markers provided herein in a manner that indicates favorable outcome of a patient having cancer would be a candidate agent for the cancer. Alternatively, an agent which is able to decrease the viability of a tumor cell comprising a marker indicative of an unfavorable outcome would be a candidate agent for the cancer.

The present invention is also directed to methods of treating a cancer patient, with a therapeutic regimen, e.g., with an NAE inhibitor, such as a 1-substituted methyl sulfamate therapy regimen, with an EGFR inhibitor, such as an erlotinib treatment regimen or a with a pan-kinase inhibitor, such as sorafenib (e.g., alone, or in combination with an additional agent such as a chemotherapeutic agent, e.g., a glucocorticoid agent, a proteasome inhibitor, an alkylating agent, a kinase inhibitor or a topoisomerase inhibitor), which includes the step of selecting for treatment a patient whose marker characteristic, e.g., composition or amount indicates that the patient is expected to have a favorable outcome with the therapeutic regimen, and treating the patient with the therapy, e.g., NAE inhibition, such as a 1-substituted methyl sulfamate therapy, EGFR inhibition, such as erlotinib therapy or pan-kinase inhibition, such as sorafenib therapy. In some embodiments, the method can include the step of selecting a patient whose marker characteristic, e.g., composition or amount or amounts indicates that the patient is expected have a favorable outcome and administering a therapy other than an NAE inhibitor therapy, other than an EGFR inhibitor therapy or other than pan-kinase therapy that demonstrates similar expected survival times as the NAE inhibitor, such as a 1-substituted methyl sulfamate therapy, as the EGFR inhibitor, such as erlotinib therapy or as the pan-kinase inhibitor, such as sorafenib therapy, respectively.

Additional methods of treating a cancer patient include selecting patients that are unlikely to experience a favorable outcome upon treatment with a cancer therapy (e.g., NAE inhibitor, such as a 1-substituted methyl sulfamate therapy, EGFR inhibitor, such as an erlotinib therapy or pan-kinase inhibitor, such as sorafenib therapy). Such methods can further include one or more of: administering a higher dose or increased dosing schedule of a therapy, e.g., NAE inhibitor, such as a 1-substituted methyl sulfamate, EGFR inhibitor, such as erlotinib or pan-kinase inhibitor, such as sorafenib as compared to the dose or dosing schedule of a patient identified as having a favorable outcome with standard therapy; administering a cancer therapy other than an NAE inhibitor, such as a 1-substituted methyl sulfamate therapy, an EGFR inhibitor, such as erlotinib therapy or pan-kinase inhibitor, such as sorafenib therapy; administering an NAE inhibitor, such as a 1-substituted methyl sulfamate agent, an EGFR inhibitor, such as erlotinib or pan-kinase inhibitor, such as sorafenib in combination with an additional agent. Further provided are methods for selection of a patient having aggressive disease which is expected to demonstrate more rapid time to progression and death.

Additional methods include a method to evaluate whether to treat or pay for the treatment of cancer by reviewing the outcome of a cancer therapy and making a decision or advising on whether payment should be made. In some embodiments, the method evaluates hematological cancer (e.g., multiple myeloma, leukemias, lymphoma, etc.) or solid tumor cancer (e.g., melanoma, esophageal cancer or bladder cancer) by reviewing the amount of a patient's marker or markers for indication of outcome to a cancer therapy, e.g., an NAE inhibitor, such as a 1-substituted methyl sulfamate therapy regimen. In other embodiments, the method evaluates the treatment of cancer, e.g., lung cancer, such as non-small cell lung cancer (NSCLC), adenocarcinoma of the lung, or lung metastases in the brain, pancreatic cancer or breast cancer by reviewing the amount of a patient's marker or markers for indication of outcome to a cancer therapy, e.g., an EGFR inhibitor, such as an erlotinib therapy regimen. In other embodiments, the method evaluates the treatment of cancer, e.g., kidney cancer, liver cancer or thyroid cancer by reviewing the amount of a patient's marker or markers for indication of outcome to a cancer therapy, e.g., a pan-kinase inhibitor, such as an sorafenib therapy regimen.

In another aspect, the invention provides a method to build predictive models of outcome of therapy. In some embodiments, the method comprises one or more steps selected from the group consisting of reviewing feature, e.g., marker, characteristics, e.g., expression data; using the correlation between the characteristic and responses to an agent to select features for training and testing; splitting the features into training and testing subsets and optionally, repeating the splitting step; consensus gene weighting, e.g., using forward searching, to find a core Partial Least Squares Regression (PLSR) model, and selecting markers based on pathway participation to focus the marker gene set.

The entire contents of all publications, patent applications, patents and other references mentioned herein are incorporated by reference.

Other features and advantages of the invention will be apparent from the following detailed description, drawings and from the claims.

DRAWINGS

FIG. 1. A. General structure of 1-substituted methyl sulfamate. $G^1$ is —O— or —CH$_2$—; $G^2$ is —H or —OH; $G^3$ is —H or —OH; $G^4$ is —NH—, —O— or a covalent bond; and $G^5$ is substituted heteroaryl; B. Structure of MLN4924.

Figure 2:
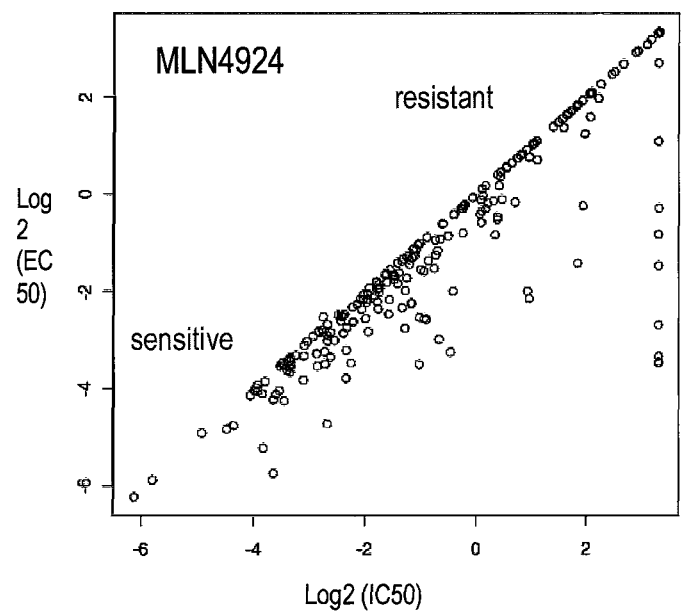

FIG. 2. Response of a cell line panel to MLN4924. Each point represents one cell line.

FIG. 3. Forward searching for a core gene set for MLN4924 PLSR model. A. AUC analysis, B. Pearson correlation. Solid line: Starting from 5 most important genes from consensus weighting in the full PLSR model, and adding one gene at a time; dotted line: one random case of selecting the same number of genes from the full PLSR model.

FIG. 4. Forward searching for a core gene set for Erlotinib PLSR model. A. AUC analysis, B. Pearson correlation. Solid line: Starting from 5 most important genes from consensus weighting in the full PLSR model, and adding one gene at a time; dotted line: one random case of selecting the same number of genes from the full PLSR model.

Figures 5A, 5B:
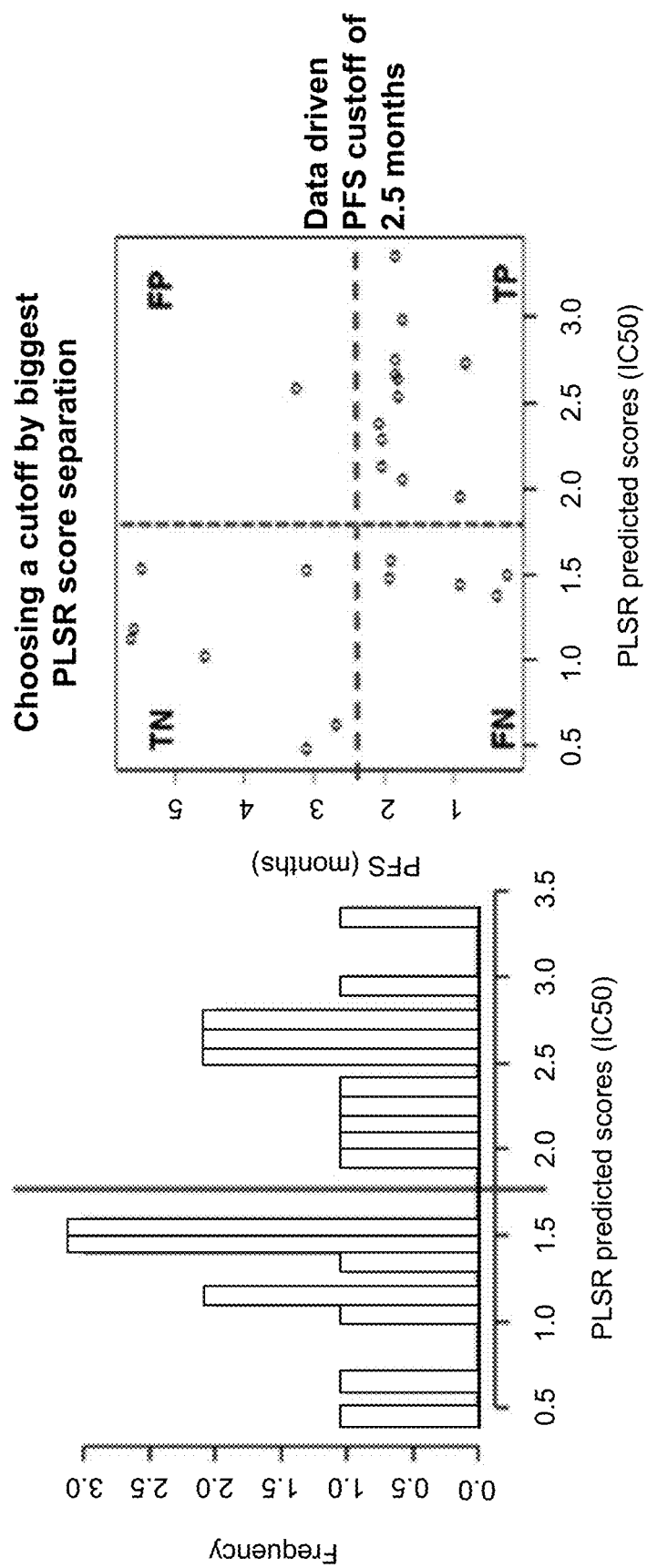

FIG. 5. FIG. 5A, Distribution of the core PLSR model-predicted erlotinib responses with a cutoff line drawn at the point of separation between outcomes; FIG. 5B, comparison of predicted outcomes with observed outcomes; the cutoffs divide the patient samples into True Negative (TN), False Negative (FN), True Positive (TP) or False Positive (FP). In this graph, the PLSR-predicted scores yielded 76% accuracy.

Figures 6A, 6B:
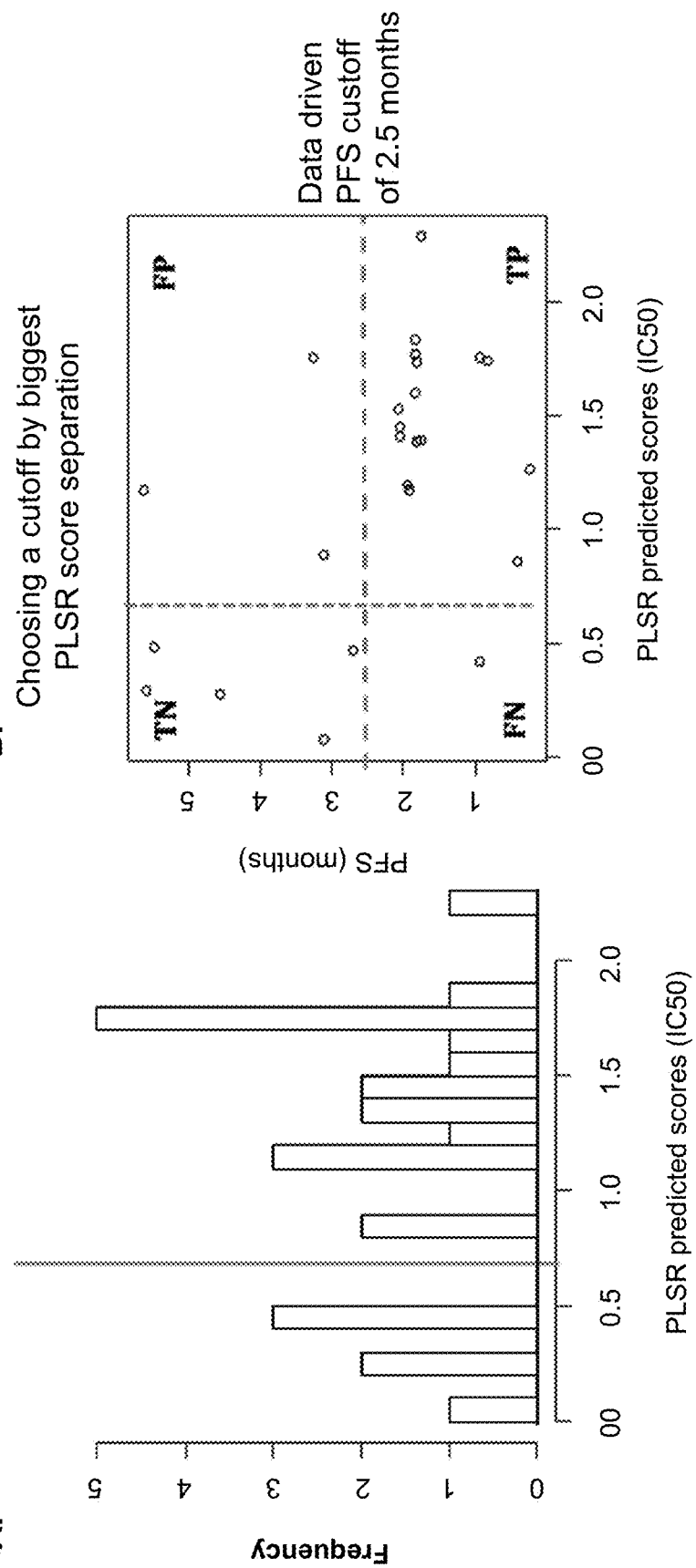

FIGS. 6A and B. Same comparisons as in FIGS. 5A and B, except using the erlotinib pathway-based PLSR model. In FIG. 6B, the accuracy is 84%.

FIG. 7. Prediction of progression-free survival in erlotinib- and sorafenib-treated patients. FIG. 7A, prediction of erlotinib-treated patients based on the erlotinib 51 gene pathway-based PLSR model; FIG. 7B, prediction of sorafenib-treated patients based on the sorafenib 113 gene pathway-based PLSR model; 7C, prediction of sorafenib-treated patients based on the erlotinib PLSR model; 7D, prediction of erlotinib-treated patients based on the sorafenib PLSR model.

FIG. 8. Comparison of the pathway-based PLSR models with overall survival outcome. Solid line, drug sensitive patients; dotted line, drug resistant patients; p is p-value; HR is hazard ratio. FIG. 8A, prediction of erlotinib-treated patients based on the erlotinib PLSR model; FIG. 8B, prediction of sorafenib-treated patients based on the sorafenib PLSR model; FIG. 8C, prediction of sorafenib-treated patients based on the erlotinib PLSR model; FIG. 8D, prediction of erlotinib-treated patients based on the sorafenib PLSR model; FIG. 8E, prediction of erlotinib-treated patients based on KRAS mutation.

Figure 9:
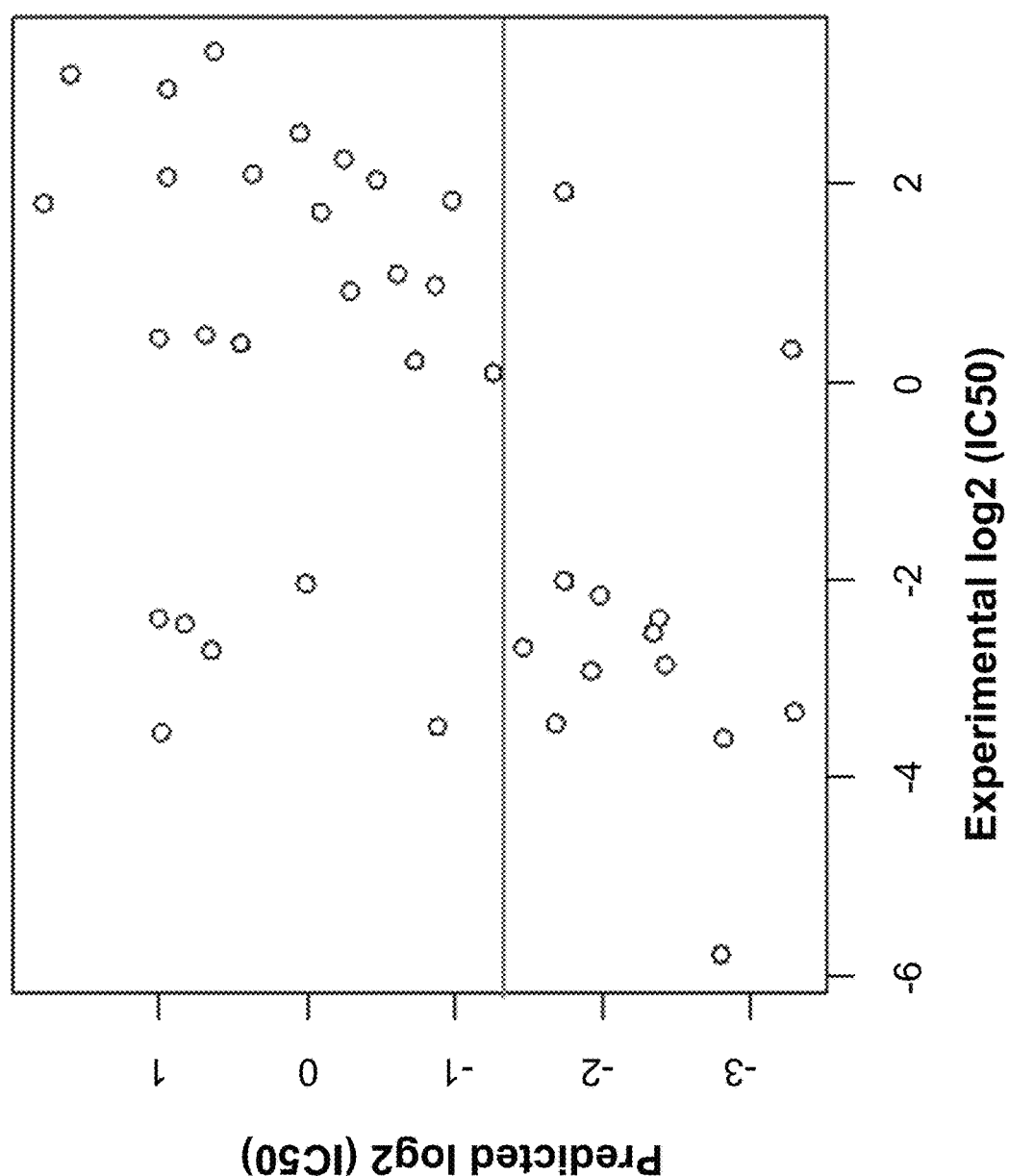

FIG. 9. Comparison of $\log_2(IC50)$ values from predicted outcome of cell line panel using MLN4924 65 gene pathway-based model vs experimental outcome of cell lines treated with MLN4924, plotted to find the cutoff to separate sensitive and resistant samples for prediction of outcome on melanoma explants.

Figure 10A:
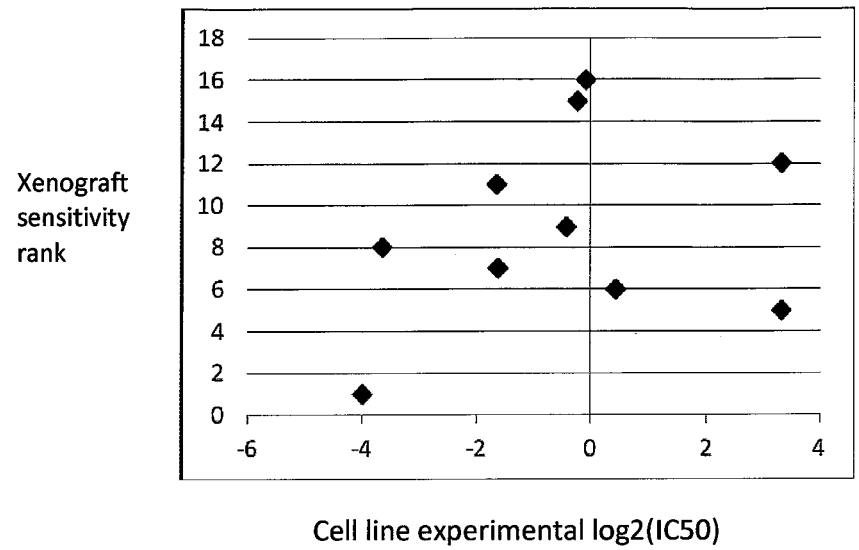
Figure 10B:
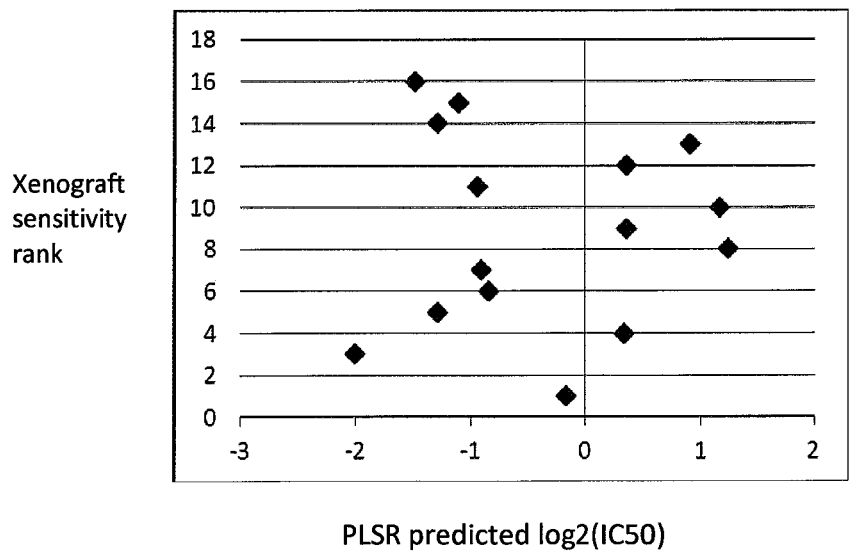

FIG. 10. Comparison of outcomes of MLN4924 treatment of tumor xenografts with inhibition in cell culture and with PLSR model prediction. FIG. 10A, comparison of xenograft with cell culture; FIG. 10B, comparison of xenograft with PLSR model.

DETAILED DESCRIPTION

One of the continued problems with therapy in cancer patients is individual differences in response to therapies. While advances in development of successful cancer therapies progress, only a subset of patients respond to any particular therapy. It would be beneficial to identify particular cancer patients who are particularly responsive to particular cancer therapies, cancer patients who would benefit from particular cancer inhibition therapies; or cancer patients who have a predisposition to be non-responsive to therapy, thus to effectively manage the disease. Targeted designed therapy may provide more focused, successful patient therapy overall. It would therefore be beneficial to provide for the diagnosis, staging, prognosis, and monitoring of cancer patients, including, e.g., hematological cancer patients (e.g., multiple myeloma, leukemias, lymphoma, etc.) or solid tumor cancer (e.g., melanoma, esophageal cancer, bladder cancer, lung cancer, breast cancer or pancreatic cancer) who would benefit from particular cancer inhibition therapies as well as those who would benefit from a more aggressive and/or alternative cancer inhibition therapy, e.g., alternative to a cancer therapy or therapies the patient has received, thus resulting in appropriate preventative measures.

The present invention is based, in part, on a method for selecting marker genes and building marker gene sets and in part on a method for using the marker genes and marker gene sets to predict response to therapy, e.g., NAE inhibition therapy, EGFR inhibition therapy or pan-kinase inhibition therapy.

In one aspect, the invention provides a method for determining whether to treat a patient having cancer with a NEDD8-activating enzyme (NAE) inhibitor, the method comprising the steps of: determining a quantitative measure of the gene expression levels for a marker gene set comprising at least two markers identified in Table 1 in a cancer cell sample obtained from the patient; using a partial least squares regression (PLSR)-based algorithm to generate a predictive outcome score based on the gene expression levels of the marker gene set; comparing the predictive outcome score to a cutoff value; and determining whether to treat the patient with the NAE inhibitor based on the comparison of the predictive outcome score with the cutoff value. In some embodiments, the method further comprises determining to treat the patient if the comparison predicts sensitivity of the cancer cell sample to the NAE inhibitor. In some embodiments, the method further comprises determining not to treat the patient if the comparison predicts resistance of the cancer cell sample to the NAE inhibitor. In some embodiments, the method further comprises determining to use a stronger than standard dose regimen of the NAE inhibitor or adding an additional therapeutic agent in combination with the NAE inhibitor if the comparison does not predict high sensitivity or high resistance of the cancer cell sample to the NAE inhibitor. In some embodiments, the method is performed in vitro.

In another aspect, the invention provides a method for identifying a patient having cancer as a candidate for treating with a NEDD8-activating enzyme (NAE) inhibitor, the method comprising the steps of: determining a quantitative measure of the gene expression levels for a marker gene set comprising markers selected from the group consisting of markers 1, 2, 3 and 4 identified in Table 1 in a cancer cell sample obtained from the patient; using a partial least squares regression (PLSR)-based algorithm to generate a predictive outcome score based on the gene expression levels of the marker gene set; comparing the predictive outcome score to a cutoff value; and identifying the patient as a candidate for treatment with the NAE inhibitor if the comparison indicates sensitivity of the cancer cell sample to the NAE inhibitor.

In another aspect, the invention provides a method for treating a patient having cancer, the method comprising the steps of determining a quantitative measure of the gene expression levels for a marker gene set comprising markers selected from the group consisting of markers 1, 2, 3 and 4 identified in Table 1 in a cancer cell sample obtained from the patient; using a partial least squares regression (PLSR)-based algorithm to generate a predictive outcome score based on the gene expression levels of the marker gene set; comparing the predictive outcome score to a cutoff value; and treating the subject with an NAE inhibitor if the comparison indicates sensitivity of the cancer cell sample to the NAE inhibitor.

In another aspect, the invention provides a method for identifying a patient having cancer as a candidate for treating with an NAE inhibitor, the method comprising the steps of: determining a quantitative measure of the gene expression levels for a marker gene set comprising markers 1-3 and 5-45 identified in Table 1 in a tumor sample obtained from the patient; generating a predictive outcome score based on the gene expression levels of the marker gene set; and comparing the predictive outcome score to a cutoff value; and predicting the patient's sensitivity or resistance to the NAE inhibitor. In some embodiments, the marker gene set further comprises marker 46, marker 47 or both marker 46 and marker 47. In some embodiments, the marker gene set further comprises markers 4 and 46-69 identified in Table 1.

In another aspect, the invention provides a method for treating cancer with an NAE inhibitor in a subject in need thereof, the method comprising the steps of: determining a quantitative measure of the gene expression levels for a marker gene set comprising markers 1-3 and 5-45 identified in Table 1; generating a predictive outcome score based on the gene expression levels of the marker gene set; comparing the predictive outcome score to a cutoff value; and treating the subject with an NAE inhibitor if the comparison indicates sensitivity to the NAE inhibitor. In some embodiments, the marker gene set further comprises marker 46, marker 47 or both marker 46 and marker 47. In some embodiments, the marker gene set further comprises markers 4 and 46-69 identified in Table 1.

In some embodiments, the marker gene set comprises markers 1 and 2. In some embodiments, the marker gene set comprises markers 1, 2, 3 and 4. In some embodiments, the marker gene set comprises markers selected from the group consisting of markers 1, 2, 3 and 4 identified in Table 1. In some embodiments, the marker gene set further comprises marker 46, marker 47 or both marker 46 and marker 47. In some embodiments, the marker gene set further comprises markers in a pathway selected from the group consisting of TGFbeta-SMAD signaling pathway, adhesion receptor-induced signaling pathway, c-myc transcription factor pathway and c-myb transcription factor pathway. In an embodiment, the marker gene set consists of markers 1-3 and 5-45 of Table 1. In some embodiments, the marker gene set consists of the markers 1-69 of Table 1. In some embodiments, the marker gene set comprises the markers 1-44, 46-48, 50, 51, 53-66, 68 and 69 identified in Table 1.

In some embodiments, the cancer cell is from a hematological cancer or a solid tumor cancer. In some embodiments, the solid tumor cancer is selected from the group consisting of skin cancer, breast cancer, colon cancer, lung cancer, pancreatic cancer, esophageal cancer, bladder cancer, and head and neck cancer. In some embodiments, the skin cancer is melanoma. In some embodiments, the hematological cancer is acute myelogenous leukemia. In some embodiments, the tumor is a hematological tumor or a solid tumor. In some embodiments, the hematological tumor is selected from the group consisting of multiple myeloma, leukemia, and lymphoma. In some embodiments, the solid tumor is selected from the group consisting of melanoma, esophageal cancer, bladder cancer, lung cancer, pancreatic cancer colorectal cancer, gastric cancer, breast cancer, ovarian cancer, cervical cancer or prostate cancer.

In some embodiments, the cutoff value is a separation cutoff value. In some embodiments, the predictive outcome score is expressed in terms of $\log_2(IC50)$ of the NAE inhibitor. In some embodiments, the $\log_2(IC50)$ has a cutoff value range of −3 to 1.0. In some embodiments, a predictive outcome score below the cutoff value indicates sensitivity to the NAE inhibitor. In an embodiment, the cutoff value is −1.45.

In some embodiments, a predictive outcome score that indicates sensitivity to the NAE inhibitor identifies the patient as a candidate for treatment with the NAE inhibitor. In some embodiments, a predictive outcome score that indicates resistance to the NAE inhibitor identifies a patient as not being a candidate for treatment with the NAE inhibitor. In some embodiments, the predictive outcome score is a separation cutoff value.

In some embodiments, the NAE inhibitor is a 1-substituted methyl sulfamate. In some embodiments, the 1-substituted methyl sulfamate is (((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulphamate).

In some embodiments, the method is performed in vitro.

In some embodiments, the marker gene expression level is determined by measuring the amount of nucleic acid of the marker genes in the marker set. In some nucleic acid embodiments the nucleic acid can be selected from the group consisting of SEQ ID NOs: 1 through 69, and splice variants thereof. In other nucleic acid embodiments, the nucleic acid is selected from the group consisting of SEQ ID NOs: 117 through 185 and fragments thereof.

In some embodiments, the marker gene expression level is determined by measuring the amount of polypeptide of the marker genes in the marker set. In some polypeptide embodiments, the polypeptide is a polypeptide or isoform thereof encoded by a nucleic acid selected from the group consisting of SEQ ID NOs: 1 through 69, and splice variant thereof.

In one aspect, the invention provides a kit comprising reagents for assessing the expression levels of a marker gene set comprising markers 1 and 2 identified in Table 1, and instructions for use. In some embodiments, the kit further comprises a reagent for assessing the expression level of marker 3. In some embodiments, the kit further comprises a reagent for assessing the expression level of marker 4. In some embodiments, the kit further comprises a reagent for assessing the level of marker 46 or marker 47 or reagents for assessing the levels of markers 46 and 47. In some embodiments, the kit further comprises reagents for assessing the expression levels of markers 5-44, 48, 50, 51, 53-66, 68 and 69 identified in Table 1. In some embodiments, the kit further comprises reagents for assessing markers 4 and 46-69 identified in Table 1. In some embodiments, the kit comprises reagents for assessing the expression levels of a marker gene set comprising markers 1-3 and 5-45 identified in Table 1, and instructions for use. The invention further provides for use of the kit in any of the claims 69 through 75 for treating cancer with an effective amount of an NAE inhibitor. In some embodiments, the kit is provided for use in vitro.

In one aspect, the invention provides a method for identifying a PLSR-based model to use for a gene expression profile that is predictive of the sensitivity of a subject to a therapeutic agent, the method comprising the steps of: dividing a gene expression dataset into a balanced split between a training dataset and a testing dataset; repeatedly using a PLSR algorithm to further divide the training dataset into sub-training and sub-testing sets by random splitting, thus training a PLSR model with the sub-training dataset; selecting top PLSR models that represent common features among the dataset; applying a consensus weighting method to identify core gene expression models most similar to the consensus; and analyzing biological pathway associations among the genes represented in the core models to identify biological pathways that are over-represented; and selecting one or more markers found in the over-represented pathways to yield a predictive marker gene set; thereby producing a PLSR-based model. In some embodiments, the consensus weighting method is a singular value decomposition based method. In some embodiments, the method further comprises at least one data reduction step. In some embodiments, the method further comprises a feature selection step.

Marker genes described herein whose characteristics are linked to outcome after NAE inhibitor, such as 1-substituted methyl sulfamate (e.g., MLN4924) treatment, are provided in Table 1. Marker genes described herein whose characteristics are linked to outcome after EGFR inhibitor, such as erlotinib treatment, are provided in Table 2. Marker genes described herein whose characteristics are linked to outcome after a pan-kinase inhibitor, such as sorafenib treatment, are provided in Table 3. Sequences of mRNA, probeset targets, i.e. sequences to which the probesets bind, corresponding to marker genes also are listed in Table 1, Table 2 and Table 3. A marker gene listed in Table 1, Table 2 and Table 3 can have isoforms which are either ubiquitous or have restricted expression. The Representative Nucleic acid SEQ ID NOs in Tables 1, 2 and 3 refer only to the mRNA encoding a representative isoform protein (e.g., longest or predominant isoform) which represents at least a precursor of such isoform and not necessarily the mature protein. These sequences are not intended to limit the marker gene identity to that isoform or precursor. The additional isoforms and mature proteins are readily retrievable and understandable to one of skill in the art by reviewing the information provided under the Entrez Gene (database maintained by the National Center for Biotechnology Information, Bethesda, Md.) identified by the ID number listed in Table 1, Table 2 or Table 3. The probeset target sequences in the Tables are the targets bound by probesets (identified by their probeset identifiers) used in the Affymetrix arrays of the Examples for measuring marker expression. Sequence targets of probesets on the Affymetrix arrays are readily available publicly (see website of AFFYMETRIX® Inc. Santa Clara Calif.). Such sequences may not necessarily be translated, but may cover an untranslated portion of the marker gene. Marker gene expression can be measured by many ways, for example, by quantifying a marker gene nucleic acid, a protein encoded by a marker gene nucleic acid or a probeset target sequence in a sample obtained from a subject, such as a tumor cell sample.

TABLE 1

| Marker Number | Marker Gene ID | Marker Gene Name | Entrez Gene ID | Representative Nucleic acid SEQ ID NO: | Probeset Identifier | Probeset target SEQ ID NO: |
|---|---|---|---|---|---|---|
| 1 | MYC | v-myc myelocytomatosis viral oncogene homolog (avian) | 4609 | 1 | 202431_s_at | 117 |
| 2 | MYB | v-myb myelocytomatosis viral oncogene homolog (avian) | 4602 | 2 | 204798_at | 118 |
| 3 | CGA | glycoprotein hormones, alpha polypeptide | 1081 | 3 | 204637_at | 119 |
| 4 | RGS10 | regulator of G-protein signaling 10 | 6001 | 4 | 204319_at | 120 |
| 5 | CAV1 | caveolin 1, caveolae protein, 22 kDa | 857 | 5 | 212097_at | 121 |
| 6 | CD55 | CD55 molecule, decay accelerating factor for complement (Cromer blood group) | 1604 | 6 | 1555950_a_at | 122 |
| 7 | CDH2 | cadherin 2, type 1, N-cadherin (neuronal) | 1000 | 7 | 203440_at | 123 |
| 8 | CFB | complement factor B | 629 | 8 | 202357_s_at | 124 |
| 9 | CLDN4 | claudin 4 | 1364 | 9 | 201428_at | 125 |
| 10 | COL4A1 | collagen, type IV, alpha 1 | 1282 | 10 | 211980_at | 126 |
| 11 | COL4A2 | collagen, type IV, alpha 2 | 1284 | 11 | 211964_at | 127 |
| 12 | CSDA | cold shock domain protein A | 8531 | 12 | 201161_s_at | 128 |
| 13 | DAB2 | Disabled homolog 2, mitogen-responsive phosphoprotein (*Drosophila*) | 1601 | 13 | 201280_s_at | 129 |
| 14 | ENC1 | ectodermal-neural cortex 1 (with BTB-like domain) | 8507 | 14 | 201341_at | 130 |
| 15 | F3 | coagulation factor III (thromboplastin, tissue factor) | 2152 | 15 | 204363_at | 131 |
| 16 | FN1 | fibronectin 1 | 2335 | 16 | 212464_s_at | 132 |
| 17 | GNG11 | guanine nucleotide binding protein (G protein), gamma 11 | 2791 | 17 | 204115_at | 133 |
| 18 | HSPG2 | heparan sulfate proteoglycan 2 | 3339 | 18 | 201655_s_at | 134 |
| 19 | ITGA2 | integrin, alpha 2 (CD49B, alpha 2 subunit of VLA-2 receptor) | 3673 | 19 | 227314_at | 135 |
| 20 | ITGA3 | integrin, alpha 3 (antigen CD49C, alpha 3 subunit of VLA-3 receptor) | 3675 | 20 | 201474_s_at | 136 |
| 21 | ITGAV | integrin, alpha V (vitronectin receptor, alpha polypeptide, antigen CD51) | 3685 | 21 | 202351_at | 137 |
| 22 | ITGB4 | integrin, beta 4 | 3691 | 22 | 204990_s_at | 138 |

TABLE 1-continued

Marker Gene Description for NAE Inhibitor Treatment

| Marker Number | Marker Gene ID | Marker Gene Name | Entrez Gene ID | Representative Nucleic acid SEQ ID NO: | Probeset Identifier | Probeset target SEQ ID NO: |
|---|---|---|---|---|---|---|
| 23 | ITGB5 | integrin, beta 5 | 3693 | 23 | 201125_s_at | 139 |
| 24 | KRT19 | keratin 19 | 3880 | 24 | 201650_at | 140 |
| 25 | LAMB1 | laminin, beta 1 | 3912 | 25 | 211651_s_at | 141 |
| 26 | LAMC1 | laminin, gamma 1 (formerly LAMB2) | 3915 | 26 | 200771_at | 142 |
| 27 | LGALS3 | lectin, galactoside-binding, soluble, 3; | 3958 | 27 | 208949_s_at | 143 |
| 28 | MMP2 | Matrix metallopeptidase 2 (gelatinase A, 72 kDa gelatinase, 72 kDa type IV collagenase) | 4313 | 28 | 201069_at | 144 |
| 29 | MSX2 | msh homeobox 2 | 4488 | 29 | 205555_s_at | 145 |
| 30 | MYLK | myosin light chain kinase | 4638 | 30 | 224823_at | 146 |
| 31 | NQO1 | NAD(P)H dehydrogenase, quinone 1 | 1728 | 31 | 210519_s_at | 147 |
| 32 | NRP1 | neuropilin 1 | 8829 | 32 | 212298_at | 148 |
| 33 | PLAT | plasminogen activator, tissue | 5327 | 33 | 201860_s_at | 149 |
| 34 | PPARG | peroxisome proliferator-activated receptor gamma | 5468 | 34 | 208510_s_at | 150 |
| 35 | PXN | paxillin | 5829 | 35 | 201087_at | 151 |
| 36 | SERPINE2 | serpin peptidase inhibitor, clade E (nexin, plasminogen activator inhibitor type 1)), member 2 | 5270 | 36 | 212190_at | 152 |
| 37 | SMAD7 | SMAD family member 7 | 4092 | 37 | 204790_at | 153 |
| 38 | SNAI2 | snail homolog 2 (Drosophila) | 6591 | 38 | 213139_at | 154 |
| 39 | TGFB2 | transforming growth factor, beta 2 | 7042 | 39 | 228121_at | 155 |
| 40 | THBD | thrombomodulin | 7056 | 40 | 203887_s_at | 156 |
| 41 | THBS1 | thrombospondin 1 | 7057 | 41 | 201109_s_at | 157 |
| 42 | TIMP2 | TIMP metallopeptidase inhibitor 2 | 7077 | 42 | 224560_at | 158 |
| 43 | TIMP3 | TIMP metallopeptidase inhibitor 3 | 7078 | 43 | 201147_s_at | 159 |
| 44 | TJP2 | tight junction protein 2 (zona occludens 2) | 9414 | 44 | 202085_at | 160 |
| 45 | VCAN | versican | 1462 | 45 | 221731_x_at | 161 |
| 46 | ABCC3 | ATP-binding cassette, sub-family C (CFTR/MRP), member 3 | 8714 | 46 | 208161_s_at | 162 |
| 47 | ABCG2 | ATP-binding cassette, sub-family G (WHITE), member 2 | 9429 | 47 | 209735_at | 163 |
| 48 | ASS1 | argininosuccinate synthase 1 | 445 | 48 | 207076_s_at | 164 |
| 49 | BAG2 | BCL2-associated athanogene 2 | 9532 | 49 | 209406_at | 165 |
| 50 | C1R | complement component 1, r subcomponent | 715 | 50 | 212067_s_at | 166 |
| 51 | C1S | complement component 1, s subcomponent | 716 | 51 | 208747_s_at | 167 |
| 52 | CD36 | CD36 molecule (thrombospondin receptor) | 948 | 52 | 228766_at | 168 |
| 53 | CTSB | cathepsin B | 1508 | 53 | 200839_s_at | 169 |
| 54 | DUSP4 | dual specificity phosphatase 4 | 1846 | 54 | 204015_s_at | 170 |
| 55 | DYNLT3 | dynein, light chain, Tctex-type 3 | 6990 | 55 | 203303_at | 171 |
| 56 | EDNRB | endothelin receptor type B | 1910 | 56 | 206701_x_at | 172 |
| 57 | EFNB2 | ephrin-B2 | 1948 | 57 | 202668_at | 173 |
| 58 | EPAS1 | endothelial PAS domain protein 1 | 2034 | 58 | 200878_at | 174 |
| 59 | FOLR1 | folate receptor 1 (adult) | 2348 | 59 | 204437_s_at | 175 |
| 60 | H1F0 | H1 histone family, member 0 | 3005 | 60 | 208886_at | 176 |
| 61 | HSPA2 | heat shock 70 kDa protein 2 | 3306 | 61 | 211538_s_at | 177 |
| 62 | HTATIP2 | HIV-1 Tat interactive protein 2 | 10553 | 62 | 209448_at | 178 |
| 63 | IRS2 | insulin receptor substrate 2 | 8660 | 63 | 209185_s_at | 179 |
| 64 | KCNN4 | potassium intermediate/small conductance calcium-activated channel, subfamily N, member 4 | 3783 | 64 | 204401_at | 180 |

TABLE 1-continued

Marker Gene Description for NAE Inhibitor Treatment

| Marker Number | Marker Gene ID | Marker Gene Name | Entrez Gene ID | Representative Nucleic acid SEQ ID NO: | Probeset Identifier | Probeset target SEQ ID NO: |
|---|---|---|---|---|---|---|
| 65 | LMNA | lamin A/C | 4000 | 65 | 203411_s_at | 181 |
| 66 | PTGES | prostaglandin E synthase | 9536 | 66 | 210367_s_at | 182 |
| 67 | PTPRM | protein tyrosine phosphatase, receptor type, M | 5797 | 67 | 1555579_s_at | 183 |
| 68 | RND3 | Rho family GTPase 3 | 390 | 68 | 212724_at | 184 |
| 69 | UPP1 | uridine phosphorylase 1 | 7378 | 69 | 203234_at | 185 |

TABLE 2

Marker Gene Description for EGFR Inhibitor Treatment

| Marker Number | Marker Gene ID | Marker Gene Name | Entrez Gene ID | Representative Nucleic acid SEQ ID NO: | Probeset Identifier | Probeset target SEQ ID NO: |
|---|---|---|---|---|---|---|
| 70 | AIM1 | absent in melanoma 1 | 202 | 70 | 212543_at | 186 |
| 71 | ALOX5 | arachidonate 5-lipoxygenase | 240 | 71 | 204446_s_at | 187 |
| 72 | ARHGDIB | Rho GDP dissociation inhibitor (GDI) beta | 397 | 72 | 1555812_a_at | 188 |
| 73 | BAMBI | BMP and activin membrane-bound inhibitor homolog (*Xenopus laevis*) | 25805 | 73 | 203304_at | 189 |
| 74 | BLNK | B-cell linker | 29760 | 74 | 207655_s_at | 190 |
| 75 | BMP4 | bone morphogenetic protein 4 | 652 | 75 | 211518_s_at | 191 |
| 76 | CASP1 | caspase 1, apoptosis-related cysteine peptidase (interleukin 1, beta, convertase) | 834 | 76 | 211368_s_at | 192 |
| 77 | CCL2 | chemokine (C-C motif) ligand 2 | 6347 | 77 | 216598_s_at | 193 |
| 78 | CDH3 | cadherin 3, type 1, P-cadherin (placental) | 1001 | 78 | 203256_at | 194 |
| 79 | COL1A2 | collagen, type I, alpha 2 | 1278 | 79 | 202403_s_at | 195 |
| 80 | DLL1 | delta-like 1 (*Drosophila*) | 28514 | 80 | 224215_s_at | 196 |
| 81 | EPS8 | epidermal growth factor receptor pathway substrate 8 | 2059 | 81 | 202609_at | 197 |
| 82 | ETV1 | ets variant 1 | 2115 | 82 | 221911_at | 198 |
| 83 | F2R | coagulation factor II (thrombin) receptor | 2149 | 83 | 203989_x_at | 199 |
| 84 | GJB2 | gap junction protein, beta 2, 26 kDa | 2706 | 84 | 223278_at | 200 |
| 85 | GJB3 | gap junction protein, beta 3, 31 kDa | 2707 | 85 | 205490_x_at | 201 |
| 86 | GNG11 | guanine nucleotide binding protein (G protein), gamma 11 | 2791 | 17 | 204115_at | 133 |
| 87 | IGFBP4 | insulin-like growth factor binding protein 4 | 3487 | 86 | 201508_at | 202 |
| 88 | IL1RN | interleukin 1 receptor antagonist | 3557 | 87 | 212657_s_at | 203 |
| 89 | ITGB6 | integrin, beta 6 | 3694 | 88 | 226535_at | 204 |
| 90 | JAG2 | jagged 2 | 3714 | 89 | 32137_at | 205 |
| 91 | JUP | junction plakoglobin | 3728 | 90 | 201015_s_at | 206 |
| 92 | KRT13 | keratin 13 | 3860 | 91 | 207935_s_at | 207 |
| 93 | KRT14 | keratin 14 | 3861 | 92 | 209351_at | 208 |
| 94 | KRT17 | keratin 17 | 3872 | 93 | 212236_x_at | 209 |
| 95 | KRT5 | keratin 5 | 3852 | 94 | 201820_at | 210 |
| 95 | L1CAM | L1 cell adhesion molecule | 3897 | 95 | 204584_at | 211 |
| 97 | LAMA3 | laminin, alpha 3 | 3909 | 96 | 203726_s_at | 212 |
| 98 | LAMC2 | laminin, gamma 2 | 3918 | 97 | 202267_at | 213 |
| 99 | LEF1 | lymphoid enhancer-binding factor 1 | 51176 | 98 | 221558_s_at | 214 |
| 100 | LGALS1 | lectin, galactoside-binding, soluble, 1 | 3956 | 99 | 201105_at | 215 |
| 101 | LIMK2 | LIM domain kinase 2 | 3985 | 100 | 202193_at | 216 |

TABLE 2-continued

Marker Gene Description for EGFR Inhibitor Treatment

| Marker Number | Marker Gene ID | Marker Gene Name | Entrez Gene ID | Representative Nucleic acid SEQ ID NO: | Probeset Identifier | Probeset target SEQ ID NO: |
|---|---|---|---|---|---|---|
| 102 | ME2 | malic enzyme 2, NAD(+)-dependent, mitochondrial | 4200 | 101 | 209397_at | 217 |
| 103 | MIR21 | microRNA 21 | 406991 | 102 | 224917_at | 218 |
| 104 | MUC4 | Mucin 4, cell surface associated | 4585 | 103 | 217109_at | 219 |
| 105 | NES | nestin | 10763 | 104 | 218678_at | 220 |
| 106 | NRG1 | neuregulin 1 | 3084 | 105 | 206343_s_at | 221 |
| 107 | NRP1 | neuropilin 1 | 8829 | 32 | 212298_at | 148 |
| 108 | PROM2 | prominin 2 | 150696 | 106 | 1552797_s_at | 222 |
| 109 | PTGES | prostaglandin E synthase | 9536 | 66 | 210367_s_at | 182 |
| 110 | PTGS1 | prostaglandin-endoperoxide synthase 1 (prostaglandin G/H synthase and cyclooxygenase) | 5742 | 107 | 215813_s_at | 223 |
| 111 | SDC2 | syndecan 2 | 6383 | 108 | 212154_at | 224 |
| 112 | SFN | stratifin | 2810 | 109 | 33322_i_at | 225 |
| 113 | SMAD4 | SMAD family member 4 | 4089 | 110 | 202527_s_at | 226 |
| 114 | SPATA13 | Spermatogenesis associated 13 | 221178 | 111 | 225564_at | 227 |
| 115 | TP63 | tumor protein p63 | 8626 | 112 | 209863_s_at | 228 |
| 116 | TUBA1A | tubulin, alpha 1a | 7846 | 113 | 209118_s_at | 229 |
| 117 | UBB | ubiquitin B | 7314 | 114 | 200633_at | 230 |
| 118 | VCAN | versican | 1462 | 45 | 221731_x_at | 161 |
| 119 | VIM | vimentin | 7431 | 115 | 201426_s_at | 231 |
| 120 | WASF1 | WAS protein family, member 1 | 8936 | 116 | 204165_at | 232 |

TABLE 3

Marker Gene Description for Pan-Kinase Inhibitor Treatment

| Marker Number | Marker Gene ID | Marker Gene Name | Entrez Gene ID | Representative Nucleic acid SEQ ID NO: | Probeset Identifier | Probeset target SEQ ID NO: |
|---|---|---|---|---|---|---|
| 121 | PDGFRA | Platelet-derived growth factor receptor alpha | 5156 | 233 | 203131_at | |
| 122 | JAM2 | Junctional adhesion molecule B | 58494 | 234 | 219213_at | |
| 123 | FGFR1 | Fibroblast growth factor receptor 1 | 2260 | 235 | 211535_s_at | |
| 124 | PTCH1 | Protein patched homolog 1 | 5727 | 236 | 209815_at | |
| 125 | HGF | Hepatocyte growth factor | 3082 | 237 | 210755_at | |
| 126 | SERPINF1 | Pigment epithelium-derived factor | 5176 | 238 | 202283_at | |
| 127 | CXCL12 | Stromal cell-derived factor 1 | 6387 | 239 | 203666_at | |
| 128 | KIF5C | Kinesin heavy chain isoform 5C | 3800 | 240 | 203130_s_at | |
| 129 | SMAD4 | Mothers against decapentaplegic homolog 4 | 4089 | 241 | 202527_s_at | |
| 130 | COL3A1 | Collagen alpha-1(III) chain | 1281 | 242 | 215076_s_at | |
| 131 | NEFH | Neurofilament heavy polypeptide | 4744 | 243 | 204412_s_at | |
| 132 | GNAO1 | Guanine nucleotide-binding protein G(o) subunit alpha | 2775 | 244 | 231951_at | |
| 133 | ITGA3 | Integrin alpha-3 | 3675 | 245 | 201474_s_at | |
| 134 | IGF1R | Insulin-like growth factor 1 receptor | 3480 | 246 | 225330_at | |
| 135 | MAP3K1 | Mitogen-activated protein kinase kinase kinase 1 | 4214 | 247 | 225927_at | |
| 136 | HLA-B | HLA class I histocompatibility antigen, B | 3106 | 248 | 209140_x_at | |
| 137 | MET | Hepatocyte growth factor receptor | 4233 | 249 | 203510_at | |
| 138 | TGFB2 | Transforming growth factor beta-2 | 7042 | 250 | 228121_at | |
| 139 | PTPRJ | Receptor-type tyrosine-protein phosphatase eta | 5795 | 251 | 227396_at | |

TABLE 3-continued

Marker Gene Description for Pan-Kinase Inhibitor Treatment

| Marker Number | Marker Gene ID | Marker Gene Name | Entrez Gene ID | Representative Nucleic acid SEQ ID NO: | Probeset Identifier | Probeset target SEQ ID NO: |
|---|---|---|---|---|---|---|
| 140 | CAV2 | Caveolin-2 | 858 | 252 | 203324_s_at | |
| 141 | EFNB2 | Ephrin-B2 | 1948 | 253 | 202668_at | |
| 142 | TUBA4A | Tubulin alpha-4A chain | 7277 | 254 | 212242_at | |
| 143 | CAV1 | Caveolin-1 | 857 | 255 | 212097_at | |
| 144 | LAMB3 | Laminin subunit beta-3 | 3914 | 256 | 209270_at | |
| 145 | TNFSF10 | Tumor necrosis factor ligand superfamily member 10 | 8743 | 257 | 202688_at | |
| 146 | LAMB1 | Laminin subunit beta-1 | 3912 | 258 | 211651_s_at | |
| 157 | LAMA3 | Laminin subunit alpha-3 | 3909 | 259 | 203726_s_at | |
| 148 | NR3C1 | Glucocorticoid receptor | 2908 | 260 | 201865_x_at | |
| 149 | CD47 | Leukocyte surface antigen CD47 | 961 | 261 | 211075_s_at | |
| 150 | CD59 | CD59 glycoprotein | 966 | 262 | 200983_x_at | |
| 151 | TGFA | Protransforming growth factor alpha | 7039 | 263 | 205016_at | |
| 152 | LAMC2 | Laminin subunit gamma-2 | 3918 | 264 | 202267_at | |
| 153 | CD274 | Programmed cell death 1 ligand 1 | 29126 | 265 | 227458_at | |
| 154 | HLA-A | HLA class I histocompatibility antigen, A | 3105 | 266 | 215313_x_at | |
| 155 | THBS1 | Thrombospondin-1 | 7057 | 267 | 201109_s_at | |
| 156 | CD55 | Complement decay-accelerating factor | 1604 | 268 | 1555950_a_at | |
| 157 | FLNB | Filamin-B | 2317 | 269 | 208614_s_at | |
| 158 | CFB | Complement factor B | 629 | 270 | 202357_s_at | |
| 159 | CFI | Complement factor I | 3426 | 271 | 203854_at | |
| 160 | ITGB6 | Integrin beta-6 | 3694 | 272 | 226535_at | |
| 161 | F11R | Junctional adhesion molecule A | 50848 | 273 | 223000_s_at | |
| 162 | IL6ST | Interleukin-6 receptor subunit beta | 3572 | 274 | 212195_at | |
| 163 | IGFBP3 | Insulin-like growth factor-binding protein 3 | 3486 | 275 | 210095_s_at | |
| 164 | FN1 | Fibronectin | 2335 | 276 | 212464_s_at | |
| 165 | MAP3K5 | Mitogen-activated protein kinase kinase 5 | 4217 | 277 | 203837_at | |
| 166 | CD74 | HLA class II histocompatibility antigen gamma chain | 972 | 278 | 209619_at | |
| 167 | EREG | Proepiregulin | 2069 | 279 | 205767_at | |
| 168 | HLA-C | HLA class I histocompatibility antigen, Cw | 3107 | 280 | 208812_x_at | |
| 169 | MACC1 | Metastasis-associated in colon cancer protein 1 | 346389 | 281 | 232151_at | |
| 170 | KRT7 | Keratin, type II cytoskeletal 7 | 3855 | 282 | 209016_s_at | |
| 171 | PSMB8 | Proteasome subunit beta type-8 | 5696 | 283 | 209040_s_at | |
| 172 | CEBPD | CCAAT/enhancer-binding protein delta | 1052 | 284 | 203973_s_at | |
| 173 | TACSTD2 | Tumor-associated calcium signal transducer 2 | 4070 | 285 | 202286_s_at | |
| 174 | RUNX2 | Runt-related transcription factor 2 | 860 | 286 | 232231_at | |
| 175 | KRT19 | Keratin, type I cytoskeletal 19 | 3880 | 287 | 201650_at | |
| 176 | LGALS3 | Galectin-3 | 3958 | 288 | 208949_s_at | |
| 177 | TNFRSF12A | Tumor necrosis factor receptor superfamily member 12A | 51330 | 289 | 218368_s_at | |
| 178 | C3 | Complement C3 | 718 | 290 | 217767_at | |
| 179 | PTHLH | Parathyroid hormone-related protein | 5744 | 291 | 211756_at | |
| 180 | ITGB4 | Integrin beta-4 | 3691 | 292 | 204990_s_at | |
| 181 | CDH2 | Cadherin-2 | 1000 | 293 | 203440_at | |
| 182 | COL4A2 | Collagen alpha-2(IV) chain | 1284 | 294 | 211964_at | |
| 183 | KRT17 | Keratin, type I cytoskeletal 17 | 3872 | 295 | 212236_x_at | |
| 184 | CXCL6 | C-X-C motif chemokine 6 | 6372 | 296 | 206336_at | |
| 185 | SDC4 | Syndecan-4 | 6385 | 297 | 202071_at | |
| 186 | IRS2 | Insulin receptor substrate 2 | 8660 | 298 | 209185_s_at | |
| 187 | AREG | Amphiregulin | 374 | 299 | 205239_at | |
| 188 | ITGA2 | Integrin alpha-2 | 3673 | 300 | 227314_at | |
| 189 | PPL | Periplakin | 5493 | 301 | 203407_at | |
| 190 | ITPR3 | Inositol 1,4,5-trisphosphate receptor type 3 | 3710 | 302 | 201189_s_at | |

TABLE 3-continued

Marker Gene Description for Pan-Kinase Inhibitor Treatment

| Marker Number | Marker Gene ID | Marker Gene Name | Entrez Gene ID | Representative Nucleic acid SEQ ID NO: | Probeset Identifier | Probeset target SEQ ID NO: |
|---|---|---|---|---|---|---|
| 191 | L1CAM | Neural cell adhesion molecule L1 | 3897 | 303 | 204584_at | |
| 192 | IL6 | Interleukin-6 | 3569 | 304 | 205207_at | |
| 193 | MMP7 | Matrilysin | 4316 | 305 | 204259_at | |
| 194 | FZD6 | Frizzled-6 | 8323 | 306 | 203987_at | |
| 195 | PPARG | Peroxisome proliferator-activated receptor gamma | 5468 | 307 | 208510_s_at | |
| 196 | CXCL1 | Growth-regulated alpha protein | 2919 | 308 | 204470_at | |
| 197 | PLAT | Tissue-type plasminogen activator | 5327 | 309 | 201860_s_at | |
| 198 | EFNA1 | Ephrin-A1 | 1942 | 310 | 202023_at | |
| 199 | CDH1 | Cadherin-1 | 999 | 311 | 201131_s_at | |
| 200 | CLDN1 | Claudin-1 | 9076 | 312 | 222549_at | |
| 201 | CLDN4 | Claudin-4 | 1364 | 313 | 201428_at | |
| 202 | CD24 | Signal transducer CD24 | 100133941 | 314 | 216379_x_at | |
| 203 | PTGS2 | Prostaglandin G/H synthase 2 | 5743 | 315 | 204748_at | |
| 204 | GJB3 | Gap junction beta-3 protein | 2707 | 316 | 205490_x_at | |
| 205 | IL18 | Interleukin-18 | 3606 | 317 | 206295_at | |
| 206 | FOSL2 | Fos-related antigen 2 | 2355 | 318 | 228188_at | |
| 207 | KLF5 | Krueppel-like factor 5 | 688 | 319 | 209212_s_at | |
| 208 | GNG11 | Guanine nucleotide-binding protein G(I)/G(S)/G(O) subunit gamma-11 | 2791 | 320 | 204115_at | |
| 209 | TPM1 | Tropomyosin alpha-1 chain | 7168 | 321 | 210986_s_at | |
| 210 | CYR61 | Protein CYR61 | 3491 | 322 | 210764_s_at | |
| 211 | SPINT1 | Kunitz-type protease inhibitor 1 | 6692 | 323 | 202826_at | |
| 212 | HBEGF | Heparin-binding EGF-like growth factor | 1839 | 324 | 203821_at | |
| 213 | TAP2 | Antigen peptide transporter 2 | 6891 | 325 | 225973_at | |
| 214 | JUP | Junction plakoglobin | 3728 | 326 | 201015_s_at | |
| 215 | COL4A1 | Collagen alpha-1(IV) chain | 1282 | 327 | 211980_at | |
| 216 | EGFR | Epidermal growth factor receptor | 1956 | 328 | 201983_s_at | |
| 217 | S100A6 | Protein S100-A6 | 6277 | 329 | 217728_at | |
| 218 | CXCL2 | C-X-C motif chemokine 2 | 2920 | 330 | 209774_x_at | |
| 219 | LEPR | Leptin receptor | 3953 | 331 | 209894_at | |
| 220 | LMNA | Prelamin-A/C | 4000 | 332 | 203411_s_at | |
| 221 | GJB2 | Gap junction beta-2 protein | 2706 | 333 | 223278_at | |
| 222 | IL1A | Interleukin-1 alpha | 3552 | 334 | 210118_s_at | |
| 223 | PTGES | Prostaglandin E synthase | 9536 | 335 | 210367_s_at | |
| 224 | PSMB9 | Proteasome subunit beta type-9 | 5698 | 336 | 204279_at | |
| 225 | KRT18 | Keratin, type I cytoskeletal 18 | 3875 | 337 | 201596_x_at | |
| 226 | PKP2 | Plakophilin-2 | 5318 | 338 | 207717_s_at | |
| 227 | ESRP2 | Epithelial splicing regulatory protein 2 | 80004 | 339 | 219395_at | |
| 228 | PLAU | Urokinase-type plasminogen activator | 5328 | 340 | 205479_s_at | |
| 229 | HES1 | Transcription factor HES-1 | 3280 | 341 | 203395_s_at | |
| 230 | ETS1 | Protein C-ets-1 | 2113 | 342 | 224833_at | |
| 231 | MUC4 | Mucin-4 | 4585 | 343 | 217109_at | |
| 232 | HSPG2 | Basement membrane-specific heparan sulfate proteoglycan core protein | 3339 | 344 | 201655_s_at | |
| 233 | IGFBP1 | Insulin-like growth factor-binding protein 1 | 3484 | 345 | 205302_at | |

Marker genes can be detected and their characteristics can be measured by contact with probesets identified in Table 1, Table 2 or Table 3. A marker gene can be detected and their characteristics can be measured by contact with a sequence selected from a group consisting of a sequence recognized by a probeset identified in Table 1, Table 2 or Table 3 or a complement of the sequence. Other detectors, such as molecules which bind nucleic acids or proteins such as the nucleic acids and proteins listed in Table 1, Table 2 or Table 3, can detect, identify and assist in the measurement of characteristics of the marker genes identified in Table 1, Table 2 or Table 3. In some embodiments, probesets other than the probesets listed in Tables 1, 2 and 3 can detect and measure the marker genes identified in Table 1, Table 2 or Table 3 and can be found on various arrays, such as an Affymetrix human gene expression array, e.g., HG133 or Human Gene 1.0 ST or U133 Plus 2.0 array (Affymetrix, Inc., Santa Clara, Calif.), an Illumina bead chip (Illumina, Inc., San Diego, Calif.) or an Agilent single channel array (Agilent Technologies, Santa Clara, Calif.).

Examples of marker genes whose characteristic, e.g., composition or expression can predict response to NAE inhibition therapy, such as 1-substituted methyl sulfamate therapy, e.g., MLN4924, include MYB, MYC, CGA and/or RGS10. In some embodiments, a marker gene set, e.g., a list of genes whose characteristics are measured to generate a score for comparison with a training set, and which can predict response to NAE inhibition therapy, such as 1-substituted methyl sulfamate therapy, e.g., MLN4924, can comprise one or more genes identified in Table 1 as marker number 1, marker numbers 1 and 2, marker numbers 2 and 3, marker numbers 3 and 4, marker numbers 1 and 4, marker numbers 1, 2 and 3, marker numbers 1, 2 and 4, marker numbers 1, 3 and 4, or marker numbers 1, 2, 3 and 4. In another embodiment, a marker gene set which can predict response to NAE inhibition therapy, such as 1-substituted methyl sulfamate therapy, e.g., MLN4924 comprises the markers identified in Table 1 as marker numbers 1 through 3 and 5 through 45. In some embodiments, a marker gene set which can predict response to NAE inhibition therapy, such as 1-substituted methyl sulfamate therapy, e.g., MLN4924 further comprises the markers identified in Table 1 as marker numbers 46 and/or 47 (ABCC3 and/or ABCG2). In another embodiment, a marker gene set which can predict response to NAE inhibition therapy, such as 1-substituted methyl sulfamate therapy, e.g., MLN4924 comprises the markers identified in Table 1 as marker numbers 1 through 44, 46 through 48, 50, 51, 53 through 66, 68 and 69, i.e., it does not comprise marker numbers 45 (VCAN), 49 (BAG2), 52 (CD36) or 67 (PTPRM). In another embodiment, a marker gene set which can predict response to NAE inhibition therapy, such as 1-substituted methyl sulfamate therapy, e.g., MLN4924 comprises the markers identified in Table 1 as marker numbers 1 through 69.

In some embodiments, the method can measure the gene expression of one or more of the markers of Table 1 by measuring the amount of one or more nucleic acids selected from the group consisting of SEQ ID NOs: 1 through 69, and splice variants thereof. In other embodiments, the method can measure the gene expression of one or more of the markers of Table 1 by measuring the amount of one or more polypeptide or isoform thereof encoded by a nucleic acid selected from the group consisting of SEQ ID NOs: 1 through 69, and splice variant thereof. In some embodiments, the method can measure the gene expression of one or more of the markers of Table 1 by measuring the amount of one or more nucleic acid selected from the group consisting of SEQ ID NOs: 117 through 185 and fragments thereof.

In some embodiments, the method can measure the gene expression of one or more of the markers of Table 2 by measuring the amount of one or more nucleic acids selected from the group consisting of SEQ ID NOs: 70 through 120, and splice variants thereof. In other embodiments, the method can measure the gene expression of one or more of the markers of Table 2 by measuring the amount of one or more polypeptide or isoform thereof encoded by a nucleic acid selected from the group consisting of SEQ ID NOs: 70 through 120, and splice variant thereof. In some embodiments, the method can measure the gene expression of one or more of the markers of Table 2 by measuring the amount of one or more nucleic acid selected from the group consisting of SEQ ID NOs: 186 through 232 and fragments thereof.

In some embodiments, the method can measure the gene expression of one or more of the markers of Table 3 by measuring the amount of one or more nucleic acids selected from the group consisting of SEQ ID NOs: 233 through 345, and splice variants thereof. In other embodiments, the method can measure the gene expression of one or more of the markers of Table 1 by measuring the amount of one or more polypeptide or isoform thereof encoded by a nucleic acid selected from the group consisting of SEQ ID NOs: 233 through 345, and splice variant thereof.

In some embodiments, outcome to treatment can be related to the activation of the pathways which are over-represented in the core PLSR model. In one embodiment, an unfavorable outcome to treatment with an NAE inhibitor, such as a 1-substituted methyl sulfamate is related to the activation of transforming growth factor (TGF) beta to mothers against decapentaplegic homolog (SMAD) signaling and adhesion receptor-induced signaling pathways. Activation of SMAD and beta-catenin, targets of the NEDD8-dependent protein degradation, can lead to an unfavorable outcome to treatment with an NAE inhibitor, such as a 1-substituted methyl sulfamate. Such inhibitors inhibit beta-catenin and SMAD degradation, thereby additionally stimulating signaling which can lead to an unfavorable outcome. In some embodiments, a favorable outcome to treatment with an NAE inhibitor, such as a 1-substituted methyl sulfamate, is related to the upregulation of transcription factors, e.g., c-myc (MYC) and c-myb (MYB), which are regulators of gene proliferation and related to cancer progression. This transcription factor upregulation can further lead to a favorable outcome by inhibiting the expression or activity of some of the genes identified as associated with an unfavorable outcome. Table 1 comprises some genes associated with these pathways. Other genes in these pathways can represent the pathway in a marker set for use as described herein and can be added to the marker set or substituted for markers in the Table 1.

A marker gene set, e.g., a list of genes whose characteristics are measured to generate a score for comparison with a training set, and which can predict response to EGFR inhibition therapy, such as erlotinib therapy, can comprise one or more of the genes identified in Table 2. In some embodiments, outcome to therapy with an EGFR inhibitor, such as erlotinib is related to upregulation of genes in the EGFR-related pathways, such as PGE2 pathways, cell adhesion chemokines and adhesion pathway, cross talk with MEK-ERK pathway or ErbB2-induced breast cancer cell invasion pathway. Table 2 comprises some genes associated with these pathways. Other genes in these pathways can represent the pathway in a marker set for use as described herein and can be added to the marker set or substituted for markers in the Table 2.

In some embodiments, outcome to therapy with a pan-kinase inhibitor, such as sorafenib, is related to upregulation of genes in the growth factor pathways. In Table 3, genes highly expressed in sorafenib-sensitive lines are markers 121 through 132. Genes highly expressed in sorafenib-resistant cell lines are markers 133 through 233. A selection of markers in growth factor pathways can form a core sorafenib predictive model. Examples of marker genes whose characteristic, e.g., composition or expression, can predict response to pan-kinase therapy, such as sorafenib, can comprise PDGFRA, FGFR1, HGF, IGF1R, MET, TGFB2, TGFA, IGFBP3, IRS2, EGFR, and IGFBP1.

The identification and/or measurement of the characteristics of the marker gene can be used to determine whether a favorable outcome can be expected by treatment of a tumor, e.g., with an NAE inhibitor, such as a 1-substituted methyl sulfamate therapy or whether an alternative therapy to and/or a more aggressive therapy with, e.g., an NAE inhibitor, such as a 1-substituted methyl sulfamate inhibitor may enhance expected survival time. For example, the compositions and methods provided herein can be used to determine whether a patient is expected to have a favorable outcome to an NAE inhibitor, such as a 1-substituted methyl sulfamate therapeutic agent or an NAE inhibitor, such as a 1-substituted methyl sulfamate dosing or administration regimen. Based on these identifications, the present invention provides, without limitation: 1) methods and compositions for determining whether an NAE inhibitor, such as a 1-substituted methyl sulfamate therapy regimen will or will not be effective to achieve a favorable outcome and/or manage the cancer; 2) methods and compositions for monitoring the effectiveness of an NAE inhibitor, such as a 1-substituted methyl sulfamate therapy (alone or in a combination of agents) and dosing and administrations used for the treatment of tumors; 3) methods and compositions for treatments of tumors comprising, e.g., NAE inhibitor, such as a 1-substituted methyl sulfamate inhibition therapy regimen; 4) methods and compositions for identifying specific therapeutic agents and combinations of therapeutic agents as well as dosing and administration regimens that are effective for the treatment of tumors in specific patients; and 5) methods and compositions for identifying disease management strategies.

The identification and/or measurement of the characteristics of the marker gene can be used to determine whether a favorable outcome can be expected by treatment of a tumor, e.g., with an EGFR inhibitor, such as erlotinib therapy or whether an alternative therapy to and/or a more aggressive therapy with, e.g., an EGFR inhibitor, such as erlotinib may enhance expected survival time. For example, the compositions and methods provided herein can be used to determine whether a patient is expected to have a favorable outcome to an EGFR inhibitor, such as erlotinib or an EGFR inhibitor, such as erlotinib dosing or administration regimen. Based on these identifications, the present invention provides, without limitation: 1) methods and compositions for determining whether an EGFR inhibitor, such as an erlotinib therapy regimen will or will not be effective to achieve a favorable outcome and/or manage the cancer; 2) methods and compositions for monitoring the effectiveness of an EGFR inhibitor, such as erlotinib therapy (alone or in a combination of agents) and dosing and administrations used for the treatment of tumors; 3) methods and compositions for treatments of tumors comprising, e.g., EGFR inhibitor, such as an erlotinib therapy regimen; 4) methods and compositions for identifying specific therapeutic agents and combinations of therapeutic agents as well as dosing and administration regimens that are effective for the treatment of tumors in specific patients; and 5) methods and compositions for identifying disease management strategies.

Ubiquitin and other ubiquitin-like molecules (ubls) are activated by a specific enzyme (an E1 enzyme) which catalyzes the formation of an acyl-adenylate intermediate with the C-terminal glycine of the ubl. The activated ubl is then transferred to a catalytic cysteine residue within the E1 enzyme through formation of a thioester bond intermediate. The E1-ubl intermediate and an E2 associate, resulting in a thioester exchange wherein the ubl is transferred to the active site cysteine of the E2. The ubl is then conjugated to the target protein, either directly or in conjunction with an E3 ligase, through isopeptide bond formation with the amino group of a lysine side chain in the target protein. The ubl named Neural precursor cell-Expressed Developmentally Downregulated 8 (NEDD8) is activated by the heterodimer NEDD8-activating enzyme (NAE, also known as APPBP1-UBA3, UBE1C (ubiquitin-activating enzyme E1C)) and is transferred to one of two E2 conjugating enzymes (ubiquitin carrier protein 12 (UBC12) and UBC17), ultimately resulting in ligation of NEDD8 to cullin proteins by the cullin-RING subtype of ubiquitin ligases. A function of neddylation is the activation of cullin-based ubiquitin ligases involved in the turnover of many cell cycle and cell signaling proteins, including p27 and I-κB. See Pan et al., *Oncogene* 23:1985-97 (2004). Inhibition of NAE can disrupt cullin-RING ligase-mediated protein turnover and can lead to apoptotic death in cells, e.g., tumor cells or cells of a pathogenic organism, e.g. a parasite. See Soucy et al. (2010) *Genes & Cancer* 1:708-716.

The term "E1 enzyme inhibitor" or "inhibitor of E1 enzyme" is used to signify a compound having a structure as defined herein, which is capable of interacting with an E1 enzyme and inhibiting its enzymatic activity. Inhibiting E1 enzymatic activity means reducing the ability of an E1 enzyme to activate ubiquitin like (ubl) conjugation to a substrate peptide or protein (e.g., neddylation). In some embodiments, an E1 enzyme inhibitor can inhibit more than one E1 enzyme. In other embodiments, an E1 enzyme inhibitor is specific for a particular E1 enzyme. In various embodiments, such reduction of E1 enzyme activity is at least about 50%, at least about 75%, at least about 90%, at least about 95%, or at least about 99%. In various embodiments, the concentration of E1 enzyme inhibitor required to reduce an E1 enzymatic activity is less than about 1 µM, less than about 500 nM, less than about 100 nM, less than about 50 nM, or less than about 10 nM.

As used herein, the term "NAE inhibitor" refers to an E1 enzyme inhibitor which inhibits the NAE heterodimer. Examples of NAE inhibitors include 1-substituted methyl sulfamates (see FIG. 1 A), including MLN4924 (see FIG. 1B). Langston S. et al. U.S. patent application Ser. No. 11/700,614, whose PCT application was published as WO07/092213, WO06084281 and WO2008/019124 (the entire contents of each of the foregoing published patent applications are hereby incorporated by reference), disclose compounds which are effective inhibitors of E1 activating enzymes, e.g., NAE. As explained in the cited publications, the NAE inhibitor may comprise a compound or a pharmaceutically acceptable salt thereof. Pharmaceutically acceptable salts may be derived from inorganic or organic acids and bases. For reviews of suitable salts, see, e.g., Berge et al, Pharm. Sci. 66:1-19 (1977) and Remington: The Science and Practice of Pharmacy, 20th Ed., ed. A. Gennaro, Lippincott Williams & Wilkins, 2000. Non-limiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. In some embodiments, NAE inhibitors do not inhibit, or are very poor at inhibiting, other (non-NAE) E1 enzymes. The compounds are useful for inhibiting NAE activity in vitro and in vivo and are useful for the treatment of disorders of cell proliferation, e.g., cancer, and other disorders associated with NAE activity, such as pathogenic infections and neurodegenerative disorders. One class of compounds described in Langston et al. are 4-substituted ((1S,2S,4R)-2-hydroxy-4-{7H-pyrrolo[2,3-d]pyrimidin-7-yl }cyclopentyl)methyl sulfamates.

Figure 1B:
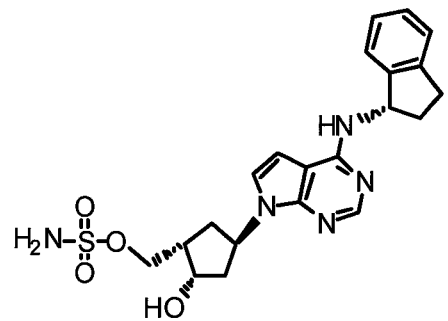

MLN4924 (((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulphamate; FIG. 1B) is an NAE-specific E1 inhibitor which disrupts cullin-RING ligase-mediated protein turnover leading to apoptotic death in human tumor cells by perturbation of cellular protein homeostasis (Soucy et al. (2009) *Nature* 458:732-736). The evaluation of MLN4924 in cellular and tumor xenograft studies has revealed two distinct mechanisms of action. The first is the induction of DNA re-replication, DNA damage and cell death through MLN4924-mediated dysregulation of the $CRL1^{SKP2}$ and $CRL4^{DDB1}$ substrate Cdt-1 (Milhollen et al. (2011) *Cancer Res.* 71:3042-3051). It has been shown that p53 status does not impact the induction of DNA re-replication but may make cells more prone to undergo apoptosis or senescence depending on the appropriate genetic background (Milhollen et al. (2011) supra, Lin et al. (2010) *Nature* 464:374-379 and Lin et al. (2010) *Cancer Res.* 70:10310-20). The second mechanism is the inhibition of NF-κB pathway activity in NF-κB dependent Diffuse Large B-Cell Lymphomas primarily through dysregulation of $CRL1^{\beta TRCP}$ mediated turnover of phosphorylated IκBα (Milhollen et al. (2010) *Blood* 116:1515-1523). In addition, preclinical models of Acute Myelogenous Leukemia (AML) are sensitive to MLN4924 inhibition in both cell lines and primary patient blasts through mechanisms related to Cdt-1 dysregulation, NF-κB inhibition and induction of reactive oxygen species (Swords et al. (2010) *Blood* 115:3796-3800).

As used herein, the term "EGFR inhibitor" refers to an inhibitor of the epidermal growth factor receptor, and can interrupt signaling through the receptor. An EGFR inhibitor can be a tyrosine kinase inhibitor, e.g., by inhibiting adenosine triphosphate (ATP) binding or hydrolysis by the EGFR. An EGFR inhibitor can block the binding of epidermal growth factor to the receptor. Examples of EGFR inhibitors which bind to the ATP binding site of the enzyme include N-(3-ethynylphenyl)-6,7-bis(2-methoxyethoxy) quinazolin-4-amine (i.e., erlotinib) and N-(3-chloro-4-fluoro-phenyl)-7-methoxy-6-(3-morpholin-4-ylpropoxy)quinazolin-4-amine (i.e., gefitinib).

As used herein, "MYC" refers to v-myc myelocytomatosis viral oncogene homolog (avian), Gene ID 4609, the gene associated with GenBank Accession No. NM_002467, SEQ ID NO:1 (open reading frame is nucleotides 526 to 1890 of SEQ ID NO:1, encoding GenPept Accession No. NP_002458). Probeset 202431_s_at targets SEQ ID NO:117 (nucleotides 1580 to 1997 of SEQ ID NO:1). Other names for MYC include bHLHe39, c-Myc and MRTL. MYC is a proto-oncogene transcription factor and plays a role in the cell cycle, transcription and apoptosis. It plays a role in a variety of cancers, including hematological cancers.

As used herein, "MYB" refers to v-myb myelocytomatosis viral oncogene homolog (avian), Gene ID 4602, a gene associated with eight isoforms, represented herein by the longest isoform, GenBank Accession No. NM_001130173, SEQ ID NO:2 (open reading frame is nucleotides 200 to 2485 of SEQ ID NO:2), encoding GenPept Accession No. NP_001123645. Probeset 204798_at targets SEQ ID NO:118 (nucleotides 3140 to 3642 of SEQ ID NO:2), which also can be found in the other MYB isoforms. Other names for MYB include c-myb and efg. MYB is a transcription factor in hematopoiesis and plays a role in a variety of cancers, including hematological cancers.

As used herein, "CGA" refers to glycoprotein hormones, alpha polypeptide, GENE ID 1081, the gene associated with GenBank Accession No. NM_000735, SEQ ID NO:3 (open reading frame is nucleotides 143 to 493 of SEQ ID NO:3), encoding GenPept Accession No. NP_000726. Probeset 204637_at targets SEQ ID NO:119 (nucleotides 127 to 649 of SEQ ID NO:3). Other names for CGA include CG-alpha, FSHA, GPHa, HCG, LHA or TSHA. CGA is the alpha subunit of chorionic gonadotropin, which is produced by the placenta early in pregnancy and can be produced by cancerous cells.

As used herein, "RGS10" refers to regulator of G-protein signaling 10, Gene ID 6001, a gene associated with two isoforms, represented herein by the shorter isoform, GenBank Accession No. NM_002925, SEQ ID NO:4 (open reading frame is nucleotides 64 to 567 of SEQ ID NO:4), encoding GenPept Accession No. NP_002916. Probeset 204319_at targets SEQ ID NO:120 (nucleotides 111 to 649 of SEQ ID NO:4). RGS10 can act as a GTPase activating protein and deactivate G protein subunits. RGS can regulate cell survival, including survival of tumor cells.

Compositions and methods are provided to measure characteristics of marker genes in hematological (e.g., multiple myeloma, leukemias, lymphoma, etc.) or solid (e.g., melanoma, esophageal cancer, lung cancer or bladder cancer) tumors to predict outcome, e.g., response to treatment, the likelihood of early disease relapse or survival upon treatment with an NAE inhibitor, e.g., a 1-substituted methyl sulfamate. Markers were identified based on expression profiles of tumor cells which exhibit sensitivity to treatment to MLN4924. Observed sensitivity generally is consistent among tumor cells tested by more than one method.

Compositions and methods are provided to measure characteristics of marker genes in lung cancer, pancreatic cancer or breast cancer tumors to predict outcome, e.g., response to treatment, the likelihood of early disease relapse or survival upon treatment with an EGFR inhibitor, e.g., a tyrosine kinase inhibitor. Markers were identified based on expression profiles of tumor cells which exhibit sensitivity to treatment to erlotinib.

Unless otherwise defined, all technical and scientific terms used herein have the meanings which are commonly understood by one of ordinary skill in the art to which this invention belongs. Generally, nomenclature utilized in connection with, and techniques of cell and tissue culture, molecular biology and protein and oligo- or polynucleotide chemistry and hybridization described herein are those known in the art. GenBank or GenPept accession numbers and useful nucleic acid and peptide sequences can be found at the website maintained by the National Center for Biotechnology Information, Bethesda, Md. The content of all database accession records (e.g., from HG133 array annotation files, Entrez, Gene, GenBank, RefSeq, COSMIC) cited throughout this application (including the Tables) are hereby incorporated by reference. The contents of files disclosing the HG-133A Probe Sequences and HG-133B Probe Sequences, both FASTA files dated Jun. 9, 2003 (see website of AFFYMETRIX®, Inc., Santa Clara, Calif.), also hereby are incorporated by reference. Standard techniques are used for recombinant DNA, oligonucleotide synthesis, protein purification, tissue culture and transformation and transfection (e.g., electroporation, lipofection, etc). Enzymatic reactions are performed according to manufacturer's specifications or as commonly accomplished in the art or as described herein. The foregoing techniques and procedures generally are performed according to methods known in the art, e.g., as described in various general and more specific references that are cited and discussed throughout the present specification. See e.g., Sambrook et al. (2000) *Molecular Cloning: A Laboratory Manual* ($3^{rd}$ ed., Cold Spring Harbor Laboratory Press, Cold Spring Harbor, N.Y.) or Harlow, E. and Lane, D. (1988) *Antibodies: A Laboratory Manual* (Cold Spring Harbor Laboratory Press, Cold Spring Harbor, N.Y.). The nomenclatures utilized in connection with, and the laboratory procedures and techniques of, analytical chemistry, synthetic organic chemistry, and medicinal and pharmaceutical chemistry described herein are known in the art. Standard techniques are used for chemical syntheses, chemical analyses, pharmaceutical preparation, formulation and delivery, and treatment of patients. Furthermore, unless otherwise required by context, singular terms shall include pluralities and plural terms shall include the singular. The articles "a" and "an" are used herein to refer to one or to more than one (i.e. at least one) of the grammatical object of the article. By way of example, "an element" means at least one element and can include more than one element. In the case of conflict, the present specification, including definitions, will control.

As used herein, a "favorable" outcome or prognosis refers to long term survival, long time-to-progression (TTP), long progression-free survival, and/or good response. Conversely, an "unfavorable" prognosis refers to short term survival, short time-to-progression (TTP), short progression-free survival and/or poor response.

As used herein, a "marker gene" as used herein, refers to a gene whose corresponding "marker" or "biomarker" material, e.g., nucleic acid and/or protein has a characteristic, e.g., composition or amount(s) whose analysis, e.g., detection, measurement, sequencing and/or quantification, provides information about outcome of treatment with an agent e.g., an NAE inhibitor, such as a 1-substituted methyl sulfamate or an EGFR inhibitor, such as erlotinib. For example, a marker includes a marker gene material, e.g., nucleic acid or protein, whose characteristic, e.g., composition or amount is indicative of a patient with a short term survival; alternatively a marker includes a marker gene material, e.g., nucleic acid or protein, which demonstrates a characteristic, e.g., composition or amount indicative of a long term survival patient. In another example, a marker includes a marker gene material, e.g., nucleic acid or protein, whose characteristic, e.g., composition or amount is indicative of a patient with a poor response to treatment; alternatively a marker includes a marker gene material, e.g., nucleic acid or protein, whose characteristic, e.g., composition or amount is indicative of a patient with a good response. In a further example, a marker includes a marker gene material, e.g., nucleic acid or protein, whose characteristic, e.g., composition or amount is indicative of a patient whose disease has a short time-to-progression (TTP) or progression-free survival upon treatment; alternatively a marker includes a marker gene material, e.g., nucleic acid or protein whose characteristic, e.g., composition or amount is indicative of a patient whose disease has a long TTP or progression-free survival upon treatment. Thus, as used herein, marker is intended to include each and every one of these possibilities, and further can include each single marker individually as a marker; or alternatively can include one or more, or all of the characteristics collectively when reference is made to "markers" or "marker sets."

A "marker set" or "marker gene set" is a group of markers, comprising two or more (e.g., about 2, 3, 4, 5, 10, 15, 20, 25, 30, 35, 40, 45, 50, 55, 60, 65, 70, 75, 100, 150, 200, 300 or 400) markers or marker genes of the invention.

A "marker nucleic acid" is a nucleic acid (e.g., genomic DNA, mRNA, cDNA) encoded by or corresponding to a marker gene of the invention. Such marker nucleic acids include without limitation, nucleic acid sequences recognized by probes and probesets, e.g., target sequences to which the probesets bind, sense and anti-sense strands of DNA, e.g., of genomic DNA (e.g., including any introns occurring therein), comprising the entire or a partial sequence, e.g., one or more of the exons of the genomic DNA, up to and including the open reading frame of any of the marker genes or the complement of such a sequence. The marker nucleic acids also include RNA comprising the entire or a partial sequence of any marker or the complement of such a sequence, wherein all thymidine residues are replaced with uridine residues, RNA generated by transcription of genomic DNA (i.e. prior to splicing), RNA generated by splicing of RNA transcribed from genomic DNA, As used herein, a "marker nucleic acid" may also include a cDNA made by reverse transcription of an RNA generated by transcription of genomic DNA (including spliced RNA). A marker nucleic acid also includes sequences which differ, due to degeneracy of the genetic code, from the nucleotide sequence of nucleic acids encoding a protein which corresponds to a marker of the invention, and thus encode the same protein. As used herein, the phrase "allelic variant" refers to a nucleotide sequence which occurs at a given locus or to a polypeptide encoded by the nucleotide sequence. Such naturally occurring allelic variations can typically result in 1-5% variance in the nucleotide sequence of a given gene. Alternative alleles can be identified by sequencing the gene of interest in a number of different individuals, e.g., in cells, e.g., germline cells, of individuals without cancer. This can be readily carried out by using hybridization probes to identify the same genetic locus in a variety of individuals. Detection of any and all such nucleotide variations and resulting amino acid polymorphisms or variations that are the result of naturally occurring allelic variation and that do not alter the functional activity of a wild type marker gene is intended to be within the scope of the wild type version of a marker described herein. A "marker protein" is a protein encoded by or corresponding to a marker, e.g., a nucleic acid, of the invention, e.g., generated by translation of RNA corresponding to a marker gene (i.e. including proteins both before and after cleavage of normally cleaved regions such as transmembrane signal sequences). The terms "protein" and "polypeptide' are used interchangeably. A protein of a marker specifically can be referred to by its name or amino acid sequence, but it is understood by those skilled in the art, that mutations, deletions and/or post-translational modifications can affect protein structure, appearance, cellular location and/or behavior. Unless indicated otherwise, such differences are not distinguished herein, and a marker described herein is intended to include any or all such varieties.

As used herein, a "characteristic" of a marker is its size, sequence, composition or amount. A characteristic can be correlated to prognosis or outcome. Information about a characteristic, of a marker can be obtained by analyzing, e.g., detecting, measuring, sequencing, and/or quantifying, either marker nucleic acid, e.g., DNA or RNA, or marker protein corresponding to the marker gene. The characteristic, e.g., composition (e.g., base or amino acid composition or peptide digest or gene fragment pattern) or amount (e.g., copy number and/or expression level), size (e.g., length or molecular weight), sequence (e.g., nucleic acid sequence or protein sequence), can provide information if it is present or absent, wild type or mutant, higher or lower than a baseline, threshold, cutoff, reference or normal amount of the marker material being analyzed. An informative expression level of a marker can be determined upon statistical correlation of the measured expression level and the outcome. The result of the statistical analysis of a characteristic can establish a threshold or range for selecting markers to use in the methods described herein. Alternatively, a marker, e.g., a marker gene that has differential characteristic, e.g., composition or amounts will exhibit ranges of amounts that are predictive of outcome. Still further, a set of markers may together be predictive if the combination of their characteristics, e.g., compositions or amounts, either meets or is above or below a pre-determined score for a marker gene set as determined by methods provided herein. Analysis of only one characteristic of a marker (e.g., nucleic acid or protein), of a marker gene can provide a result which leads to a prognosis, i.e., indicates outcome. Analysis of more than one characteristic of a marker or more than one marker material corresponding to a marker gene can provide a result which leads to a prognosis when the results of the more than one analyses are consistent with each other, i.e., the biologies of the results are not contradictory. Examples of consistent results from measurement of multiple characteristics of a marker or more than one marker material corresponding to a marker gene can be identification of a nonsense mutation or deletion in a DNA or RNA and a low amount or low molecular weight of encoded protein, or a more than normal copy number, e.g., more than two, of a gene and high expression of the mRNA or high activity of the encoded protein. A different example can occur when a protein is in a pathway with a feedback loop controlling its synthesis based on its activity level. In this example, a low amount or activity of protein can be associated with a high amount of its mRNA as a tissue, due to a marker gene mutation, thus is starved for the protein activity and repeatedly signals the production of the protein.

As used herein, "gene deletion" refers to an amount of DNA copy number less than 2 and "amplification" refers to an amount of DNA copy number greater than 2. A "diploid" amount refers to a copy number equal to 2. The term "diploid or amplification" can be interpreted as "not deletion" of a gene copy. In a marker whose alternative informative amount is gene deletion, amplification generally would not be seen. Conversely, the term "diploid or deletion" can be interpreted as "not amplification" of copy number. In a marker whose alternative informative amount is amplification, gene deletion generally would not be seen. For the sake of clarity, sequence deletion can occur within a gene as a result of marker gene mutation and can result in absence of transcribed protein or a shortened mRNA or protein. Such a deletion may not affect copy number.

The term "time-to-progression" (TTP) or "progression-free survival" (PFS) refer to the length of time after treatment with an agent, when a patient lives with the disease, e.g., stable disease brought by treatment, until the disease converts into an active, progressive disease. These terms refer to technically different time periods, but have high overlap and are used interchangeably herein to refer to a time, e.g., long or short, between treatment and relapse. On occasion, a treatment results in stable disease which is neither a good nor a poor response, e.g., MR, the disease merely does not get worse, e.g., become a progressive, i.e., active, disease, for a period of time. The period of time from time of treatment to time of progressive disease can be at least 2-6 weeks, at least 4-8 weeks, at least 2-4 months, at least 3-6 months or more than 6 months.

The terms "long term survival" and "short term survival" refer to the length of time after receiving a first dose of treatment that a patient, e.g., a cancer patient is predicted to live. A "long term survivor" refers to a patient expected have a slower rate of progression or later death from the tumor than those patients identified as short term survivors. "Enhanced survival" or "a slower rate of death" are estimated life span determinations based upon characteristic, e.g., size, sequence, composition or amount of one or more of markers described herein, e.g., as compared to a reference standard such that 70%, 80%, 90% or more of the population will be alive a sufficient time period after receiving a first dose of treatment. A "faster rate of death" or "shorter survival time" refer to estimated life span determinations based upon characteristic, e.g., size, sequence, composition or amount of one or more of markers described herein, e.g., as compared to a reference standard such that 50%, 40%, 30%, 20%, 10% or less of the population will not live a sufficient time period after receiving a first dose of treatment. In some embodiments, the sufficient time period is at least 6, 12, 18, 24 or 30 months measured from the first day of receiving a cancer therapy.

A disease, e.g., cancer, a tissue, e.g., a tumor or a cell, e.g., a cell line or a cell from a tumor, is "responsive" or "sensitive" to a therapeutic agent or there is a "good response" to a treatment if its rate of growth is inhibited as a result of contact with the therapeutic agent, compared to its growth in the absence of contact with the therapeutic agent. A disease, e.g., cancer, a tissue, e.g., a tumor or a cell, e.g., a cell line or a cell from a tumor, is "non-responsive" or "resistant" to a therapeutic agent or there is a "poor response" if its rate of growth is not inhibited, or inhibited to a very low degree, as a result of contact with the therapeutic agent when compared to its growth in the absence of contact with the therapeutic agent. Growth of a cancer can be measured in a variety of ways, for instance, the characteristic, e.g., size of a tumor or the expression of tumor markers appropriate for that tumor type may be measured. For example, the response definitions used to support the identification of markers associated with myeloma and its response to an NAE inhibitor, such as a 1-substituted methyl sulfamate therapy, the Southwestern Oncology Group (SWOG) criteria as described in Blade et al. (1998) *Br J Haematol.* 102:1115-23 can be used. These criteria define the type of response measured in myeloma and also the characterization of time to disease progression which is another important measure of a tumor's sensitivity to a therapeutic agent. For solid tumors, the Response Evaluation Criteria in Solid Tumors (RECIST) guidelines (Eisenhauer et al. (2009) *E. J. Canc.* 45:228-247) can be used to support the identification of markers associated with solid tumors and response of solid tumors to an NAE inhibitor or an EGFR inhibitor. International Working Groups convene periodically to set, update and publish response criteria for various types of cancers. Such published reports can be followed to support the identification of markers of the subject tumors and their response to NAE inhibitors or EGF inhibitors. Examples are criteria for Acute Myelogenous Leukemia (AML, Cheson et al. (2003) *J. Clin. Oncol.* 21:4642-4649), lymphomas, e.g., non-Hodgkin's and Hodgkin's lymphoma (Cheson et al. (2007) *J. Clin. Oncol.* 25:579-596). Criteria take into account analysis methods such as Positron Emission Tomography (PET), e.g., for identifying sites with measurable altered metabolic activity (e.g., at tumor sites) or to trace specific markers into tumors in vivo, immunohistochemistry, e.g., to identify tumor cells by detecting binding of antibodies to specific tumor markers, and flow cytometry, e.g., to characterize cell types by differential markers and fluorescent stains, in addition to traditional methods such as histology to identify cell composition (e.g., blast counts in a blood smear or a bone marrow biopsy, presence and number of mitotic figures) or tissue structure (e.g., disordered tissue architecture or cell infiltration of basement membrane). The quality of being responsive to an NAE inhibitor, such as a 1-substituted methyl sulfamate therapy or an EGFR inhibitor, such as erlotinib, can be a variable one, with different cancers exhibiting different levels of "responsiveness" to a given therapeutic agent, under different conditions. Still further, measures of responsiveness can be assessed using additional criteria beyond growth size of a tumor, including patient quality of life, degree of metastases, etc. In addition, clinical prognostic markers and variables can be assessed (e.g., M protein in myeloma, PSA levels in prostate cancer) in applicable situations.

"Treatment" shall mean the use of a therapy to prevent or inhibit disease, e.g., inhibit tumor growth, as well as to cause shrinkage of a tumor, and/or to provide longer survival times. Treatment is also intended to include prevention of metastasis of tumor. A disease, e.g., tumor, is "inhibited" or a patient is "treated" if at least one symptom (as determined by responsiveness/non-responsiveness, time to progression, or indicators known in the art and described herein) of the disease, e.g., cancer or tumor, is alleviated, terminated, slowed, minimized, or prevented. Any amelioration of any symptom, physical or otherwise, of a patient pursuant to treatment using a therapeutic regimen (e.g., NAE inhibitor, such as a 1-substituted methyl sulfamate regimen or EGFR inhibitor, such as erlotinib regimen) as further described herein, is within the scope of the invention.

As used herein, the term "agent" is defined broadly as anything that diseased cells or tissue, e.g., cancer cells, including tumor cells, may be exposed to in a therapeutic protocol. In the context of the present invention, such agents include, but are not limited to, NAE inhibitors, such as a 1-substituted methyl sulfamate agents, EGFR inhibitors, such as erlotinib, as well as chemotherapeutic agents as known in the art and described in further detail herein.

The term "probe" refers to any molecule which is capable of selectively binding to a specifically intended target molecule, for example a marker of the invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

A "normal" characteristic, e.g., size, sequence, composition or amount of a marker may refer to the characteristic, e.g., composition or amount in a "reference sample." A reference sample can be a matched normal, e.g., germline, sample from the same patient from whom the diseased tissue, e.g., tumor, is derived. A reference sample can be a sample from a healthy subject not having the disease. A reference value of a characteristic can be the average value, e.g., composition or amount of the characteristic of a wild type marker in several healthy subjects. A reference value of a characteristic, e.g., composition or amount, may be comprised of a level, e.g., baseline, e.g., composition or amount of one or more markers from a reference database, e.g., as normalized across an entire genome in an array. The normal amount of DNA copy number is 2 or diploid, with the exception of X-linked genes in males, where the normal DNA copy number is 1.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In an embodiment, the first region comprises a first portion and the second region comprises a second portion, whereby, when the first and second portions are arranged in an antiparallel fashion, at least about 50%, at least about 75%, at least about 90%, or at least about 95% or all of the nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue (i.e., by percent identity). By way of example, a region having the nucleotide sequence 5'-ATTGCC-3' and a region having the nucleotide sequence 5'-TATGGC-3' share homology with 50% identity. In one embodiment, the first region comprises a first portion and the second region comprises a second portion, whereby, at least about 50%, at least about 75%, at least about 90%, or at least about 95% of the nucleotide residue positions of each of the portions are occupied by the same nucleotide residue. In an embodiment of 100% identity, all nucleotide residue positions of each of the portions are occupied by the same nucleotide residue.

Unless otherwise specified herewithin, the terms "antibody" and "antibodies" broadly encompass naturally-occurring forms of antibodies, e.g., polyclonal antibodies (e.g., IgG, IgA, IgM, IgE) and monoclonal and recombinant antibodies such as single-chain antibodies, two-chain and multi-chain proteins, chimeric, CDR-grafted, human and humanized antibodies and multi-specific antibodies, as well as fragments and derivatives of all of the foregoing, which fragments (e.g., dAbs, scFv, Fab, F(ab)'$_2$, Fab') and derivatives have at least an antigenic binding site. Antibody derivatives may comprise a protein or chemical moiety conjugated to an antibody. The term "antibody" also includes synthetic and genetically engineered variants.

A "kit" is any article of manufacture (e.g., a package or container) comprising at least one reagent, e.g. a probe, for specifically detecting a marker or marker set of the invention. The article of manufacture may be promoted, distributed, sold or offered for sale as a unit for performing, e.g., in vitro, the methods of the present invention, e.g., on a sample having been obtained from a patient. The reagents included in such a kit can comprise probes/primers and/or antibodies for use in detecting or measuring marker expression. In addition, a kit of the present invention can contain instructions which describe a suitable detection assay. Such a kit can be conveniently used, e.g., in a clinical or a contract testing setting, to generate information, e.g., on expression levels, characteristic, e.g., composition of one or more marker, to be recorded, stored, transmitted or received to allow for diagnosis, evaluation or treatment of patients exhibiting symptoms of cancer. In some embodiments, the kit can be used for patients exhibiting the possible presence of a cancer capable of treatment with NAE inhibition therapy, including, e.g., hematological cancers e.g., myelomas (e.g., multiple myeloma), lymphomas (e.g., non-hodgkins lymphoma), leukemias (e.g., acute myelogenous leukemia), and solid tumors (e.g., tumors of skin, lung, breast, ovary, etc.). In other embodiments, the kit can be used for patients exhibiting the possible presence of a cancer capable of treatment with EGFR inhibition therapy, including lung cancer, breast cancer, pancreatic cancer and metastases of lung cancer in the brain.

The present methods and compositions can be used in diagnostics and therapeutics for a patient suffering from cancer. A cancer or tumor can be treated or diagnosed according to the present methods. "Cancer" or "tumor" is intended to include any neoplastic growth in a patient, including an initial tumor and any metastases. The cancer can be of the hematological or solid tumor type. Hematological tumors include tumors of hematological origin, including, e.g., myelomas (e.g., multiple myeloma), leukemias (e.g., Waldenstrom's syndrome, chronic lymphocytic leukemia, acute myelogenous leukemia, chronic myelogenous leukemia, other leukemias), lymphomas (e.g., B-cell lymphomas, non-Hodgkin's lymphoma, Hodgkin's disease) and myelodysplastic syndrome. Solid tumors can originate in organs, and include cancers such as in skin, lung, brain, breast, prostate, ovary, colon, kidney, pancreas, liver, esophagus, stomach, intestine, bladder, uterus, cervix, testis, adrenal gland, etc. As used herein, cancer cells, including tumor cells, refer to cells that divide at an abnormal (increased) rate or whose control of growth or survival is different than for cells in the same tissue where the cancer cell arises or lives. Cancer cells include, but are not limited to, cells in carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; cells in sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; cells in hematologic cancers, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large Bcell lymphoma, malignant lymphoma, plasmocytoma, reticulum cell sarcoma, or Hodgkins disease); and cells in tumors of the nervous system including glioma, meningoma, medulloblastoma, schwannoma or epidymoma.

Biomarker Modeling Framework

For drug response biomarkers, a recent FDA-led project (Shi et al. (2010) *Nat. Biotechnol.* 28:827-838) was conducted to evaluate methods of using gene expression data for predicting clinical endpoints (MAQCII: MicroArray Quality Control II). In the project, 36 independent teams analyzed six microarray data sets to generate predictive models for classifying a sample with one of 13 endpoints. Using independent testing data, the study found that most teams' gene expression-based predictive models perform very well on several endpoints, including estrogen receptor status and liver overall necrosis scores. However, all the teams made poor predictions on overall survival on multiple myeloma patients because an arbitrary cutoff (24 months) was preselected for grouping patients (to solve a classification problem). On the other hand, since both gene expression and overall survival data in the multiple myeloma case are continuous variables, one can also build a regression based prediction model (to solve a regression problem). In fact, the team who originally generated the multiple myeloma dataset adopted a uni-variance Cox regression approach to analyze the data, and was able to identify a signature gene set that can define a "high-risk" subgroup of ~14% patients (Zhan et al. (2006) *Blood* 2020-2028). Later validation of this signature highlighted the advantage of using a regression approach without predefining class memberships.

A Partial Least Squares Regression (PLSR) modeling approach is utilized herein because it can be applied to IC50 data, and it can effectively handle high number of independent variables with minimal demands on sample size. Additionally, a special splitting strategy can be implemented to capture consensus features in the training dataset, followed by a pathway-based filtering step to highly reduce the signature gene set without losing model performance. Recently, functional groups (such as pathways and networks) have been incorporated into gene expression-based predictive model building approaches to improve the model performance (reviewed at Nikolsky et al. (2011) Applied Statistics for Network Biology: Methods in Systems Biology, 415-442). In several comparative studies, performance of pathway descriptors was similar or exceeded gene signatures even on relatively small gene expression datasets. Furthermore, functional predictors may be less sensitive to molecular tumor heterogeneity, and therefore, can be more robust predictors (as different genes from the same pathway could be altered in different patients).

A typical biomarker modeling approach divides a dataset into training and testing subsets: train a model on a training subset, then test it on a testing subset. By repeating this process many times, one can generate a distribution on model performance on the testing subsets. A mean or median of this distribution is used to indicate the model performance. In one aspect, the biomarker modeling framework described herein can find the top performance model(s) that can represent the key features across the dataset. The top model(s) can have better performance than the mean or median of the distribution of random splits, therefore provide high prediction ability, e.g., of outcome of therapy. In one embodiment, a method to build predictive models focuses on using only gene expression data, e.g., from cell lines tested in in vitro screens of agent activity thereon or from samples of patients, e.g., humans, e.g., cancer patients, treated with a drug or agent. Gene expression data is readily obtainable by standard methods known in the art, described herein or online in public databases from published studies or deposited by investigators in public repositories. In other embodiments, a method to build predictive models can focus on using gene amplification data or gene mutation data, alone, or in combination with gene expression data.

In some embodiments, the method comprises reviewing characteristics, e.g., expression data, of potential markers in samples, e.g., cells from culture or samples from patients, e.g., tumor samples, with known response to an agent, e.g., sensitivity or resistance to the agent. In some embodiments, the method to build a biomarker modeling framework can comprise selecting data sets, e.g., a collection of features, or potential markers from the samples, e.g., cells or tumors, organized by a variety of ways, e.g., IC50, EC50, response, time-to-progression or progression-free survival, or overall survival upon treatment with an agent, for training and testing; splitting the features into training and testing, e.g., sep-testing, subsets; consensus gene weighting, e.g., using forward searching, to find a core Partial Least Squares Regression (PLSR) model, e.g., marker set, e.g., marker gene set; and selecting markers based on pathway participation to focus the marker set.

In one embodiment, prior to feature selection, the method can comprise at least one data reduction step. Data reduction can comprise one or more of steps selected from the group consisting of: normalizing the data, establishing an intensity threshold, and applying a variance threshold. A data normalization process for a gene expression array can be a robust multi-array (RMA) average, e.g., across the whole genome using a quantile-based approach, to stabilize a baseline of characteristics, e.g., the expression of each gene in each sample, e.g., cell line. A reason to normalize the data across the platform, e.g., array, is that a characteristic of an individual marker, e.g., gene, might be different under different conditions or different samples, but the entire platform, e.g., whole genome in an array, and its distribution should be similar to each other, since the majority of markers are not regulated in a condition. An intensity threshold can be 30%, 40%, 50%, 60%, of intensity, e.g., of the measurement of the characteristic, to minimize inclusion of features that may not really be present in the system and thus may be producing a weak background intensity. In one embodiment, the intensity threshold is 40%. A variance threshold, e.g., cutoff, can be 0.25, 0.5, 0.75, 1.0, 1.25, 1.5, 2.0, 2.5 or higher, to keep only features, e.g., marker genes, whose characteristics, e.g., expression, vary the most from sample to sample. In one embodiment, the variance threshold is 1.0. In one embodiment, prior to feature selection, the method comprises the data reduction steps of normalizing the data, establishing an intensity threshold, and applying a variance threshold.

The step of feature selection from the selected data set, e.g., a reduced data set, e.g., filtered features identified by probesets, includes determining the correlation between each probeset's expression result and responses of the samples to the agent, e.g., as $\log_2(IC50)$. Permutation is performed on each probeset by randomly assigning an agent response to samples, e.g., panel cell lines, and a raw p-value is calculated based on the permutation testing. Feature probesets are selected using a raw p-value cutoff, e.g., 0.001, 0.01, 0.05, or 0.1. In one embodiment, p-value cutoff is 0.01. The expression of some genes can be measured by more than one probeset in an array. In the case of genes represented by more than one probeset, the intensity of the result, e.g., expression measurement from each probeset for a gene is evaluated. The probeset yielding the highest intensity result for a gene's expression is selected as a representative probeset for the gene. That highest intensity probeset typically also is the highest variance probeset for that gene.

The features can be split into training and testing models by several methods, including randomly or in a balanced way. Random splitting of the full data set can limit the model, e.g., to the mean or median of the distribution, and can risk excluding some consistent features from the correlation. For example, a possibility after a random split is that most training samples are extremely resistant to an agent. Consequently, the resulting model may capture only features related to resistance, without capturing information on sensitivity to the agent. A balanced way of splitting can ensure that the model is representative of the entire set, i.e., comprises consistent or common features, e.g., from cell lines results with both high and low IC50 values, with similar frequency as in the entire training dataset. For example, the samples, e.g., cell lines, e.g., organized by IC50, can be divided into even portions and then a fixed proportion of cell lines, e.g., 10%, 20%, 30%, 40%, 50%, 60%, 70% 80% or 90%, is pulled randomly from each portion to be combined into the sep-testing group. Depending on the training dataset sample size and distribution of drug treatment response, the number of even portions can increase. For example, with a very large cell line panel, one can potentially increase number of even portions from three to ten or more, to better capture the features of the whole agent treatment distribution. The split, e.g., balanced split, can be repeated, e.g., at least 2 times, at least 10 times, at least 25 times, at least 50 times, at least 100 times, at least 125 times at least 150 times, at least 200 times, at least 250 times, at least 300 times, at least 400 times or more, to include different combinations of data. The ratio for apportioning samples, and thus data therefrom, into training and testing sets can vary by considering the number of samples, e.g., size of the cell line panel or number of patients, distribution of the observed agent responses, and cancer type information.

In one embodiment, the method further comprises further splitting the training subset into sub-training and sub-testing subsets. In this embodiment, the first split into training and testing sets can be performed by balanced splitting; and the sub-splitting, e.g., the repeated sub-splitting, into sub-testing and sub-training sets can be performed by random splitting. In an example of the eventual result of the splitting, e.g., when the balanced split divides the full data into 70% training and 30% sep-testing and then the training subset data is divided into 60% for sub-training and 40% for sub-testing, the sep-testing subset can contain 30% of the data (balanced), sub-training subset can contain 42% of the data and the sub-testing subset can contain 28% of the data (not necessarily balanced). The percentage of these subsets can vary. With a larger number of samples, e.g., a large cell line panel, a wider range of agent response, and fewer cancer types in the training dataset, one can potentially decrease the ratios of sub-testing and sep-testing groups to as low as 10% each (therefore sub-training ratio can increase to as high as 80%). Overall, the data can be split more than 1000, more than 10,000, or more than 100,000 times (multiplying the number of times the main data set is split and the number of times the training set is split). In one embodiment, there are about 200,000 splits, with PLSR training/testing on each split. In one embodiment, this splitting strategy is performed on large cell line panels, to avoid a potential drawback of yielding very small subsets.

In a further embodiment, the splitting of the training subset into sub-training and sub-testing subsets can include training a model on the sub-training subset and evaluating its performance on a sub-testing as well as sep-testing subsets. This training and testing evaluation on the subsets can be repeated, e.g., at least 10 times, at least 100 times, at least 250 times at least 500 times, at least 1000 times, at least 2000 times, at least 4000 times or more.

The training and testing can be performed using the PLSR method, which can handle a high number of independent variables with minimal demands on sample size (Lindgren et al. (1993) *J. Chemometrics* 7:45-59; Wold et al., *Chemometrics and Intelligent Laboratory Systems* 58:109-130; Jane et al (2006) *Cell* 124:1225-1239). PLSR finds fundamental relationship between observable variables and predicted variables by projecting them both to a new space. In other words, the PLSR method, there are continuous variables for both independent and dependent variables and both of the variable types are projected into a series of new orthogonal directions. In the new directions, independent and dependent variables have the maximum co-variance. PLSR works very well on a high number of independent variables, which fits very well with gene signature predictions. PLSR has minimal demands on sample size. Unlike many other regression based approaches, PLSR has no multicollinearity problem. The following is the basic algorithm of PLSR: if X is denoted as an n×p matrix of predictor variable and Y as a n×q matrix of response variable. PLS regression tries to find latent decompositions that, $$Y=TQ^T+F, \text{ and } X=TP^T+E,$$

where T is a n×k matrix that produces k linear combinations (scores), P (a p×k matrix) and Q (a q×k matrix) are matrices of coefficients (loadings), and E (a n×p matrix) and F (a n×q matrix) are matrices of random errors. To specify the latent component matrix T such that T=XW, PLS requires finding the columns of $W=(w_1, w_2, \ldots, w_k)$ from successive optimization problems. The criterion for the kth estimated direction vector $\hat{w}_k$ is formulated as $$\hat{w}_k = \operatorname{argmax}_w w^T X^T Y Y^T X w \text{ subject to: } w^T w = 1,$$
$$w^T S_{XX} \hat{w}_j = 0$$

for j=1, ..., k−1, where $S_{XX}$ is the sample covariance matrix of X. After estimating the latent components (T), loadings (Q) are estimated via ordinary least square for the model $Y=TQ^T+F$. $\beta^{PLS}$ is estimated by $\hat{\beta}^{PLS}=\hat{W}\hat{Q}^T$, where $\hat{W}$ and $\hat{Q}$ are estimates of W and Q, since $Y=XWQ^T+F=X\beta^{PLS}+F$. PLSR can be modeled within the publicly available R software package "PLS" (Comprehensive R Archive Network, available at the website maintained by The R Foundation for Statistical Computing, hosted by Vienna University of Economics and Business, Vienna, Austria). Other software is available for PLSR analysis, such as SPOTFIRE® Platform (TIBCO Software, Inc., Palo Alto, Calif.) and MATLAB® software (Mathworks, Inc. Natick, Mass.).

Another modeling method is Elastic net regression modeling (Zou and Hastie, (2005) *J. R. Statist. Soc. B* 67:301-320). Similar to PLSR, Elastic net projects both independent and dependent variables into orthogonal new directions to search for maximized relationship between these variables. Different from PLSR, Elastic net aims at maximizing correlation coefficient between independent and dependent variables (rather than maximizing covariance as in PLSR). In addition, Elastic net was mainly used to identify key features that may related to a drug's mechanism of action, but not to build predictive model for drug treatment response in the two recent studies (Garnett et al. (2012) *Nature* 483:570-577; Barretina et al. (2012) *Nature* 483:603-607).

The top models, e.g., from PLSR analysis, e.g., at least two models, at least 4 models, at least 6 models, at least 10 models, at least 25 models, at least 50 models, at least 75 models or at least 100 models, in this series of evaluations can be selected for further model building. In a further embodiment, the features of the top models are compared to determine the degree of overlap and discard overlapping models. If there is too much overlap of features among the top models, there is risk that the final model will lose representation of portions of the original data set, e.g., from an entire panel of cell lines. By minimizing overlap of top models, the modeling framework can be ensured to capture common features across the whole panel. The overlap can be tested on all possible model pairs. Overlapping models can be analyzed to generate a score of overlap. Models can be discarded based on the score relation to a cutoff value, e.g., 80% quantile, 85% quantile, 90% quantile, 95% quantile, 97% quantile or 99% quantile. In an example of a review of overlap, a model with pairwise scores of 0.3, 0.25 and 0.35 (a score of 1.0 is complete overlap) might be discarded while a model with pairwise scores of 0.27, 0.22 and 0.30 might be retained for the next steps.

Consensus weighting can reliably prioritize features, e.g., genes, based on the loadings of multiple PLSR models than a single model. This process is often referred to as rank aggregation in the related literature since the final relative importance of each gene (i.e. rank) is determined as a result of its aggregated ranks from multiple models or modalities. This process can be similarly conducted by using other available rank aggregation methods. Rank aggregation methods are largely grouped into three categories: the Condorcet method, averaging method, and evolutionary optimization method. The first group of methods use order statistics, where it is investigated if the relative of order between gene A and gene B is more likely to be kept in individual order lists than not. Then, each probable rank list is scored and the rank list with the highest score is selected as a final. Methods in the second category take a weighted average of gene weights computed from individual rank lists for a gene and use the weighted average as a final score for the gene. The weighting scheme can be ad hoc or heuristic, or data-driven by considering the overall distribution of feature, e.g., gene weights. An example of the data-driven case is the singular value decomposition (SVD)-based method. The third category covers methods that adopt computationally intensive optimization algorithms for finding an aggregated rank list. Evolutionary algorithms such as genetic algorithm or simulated annealing are often selected for optimizing a scoring function of each proposed rank list. Evolutionary algorithms mimic natural selection in the nature, attempting to seek the optimal or near best solution (in this case, aggregated rank list) by searching a number of potentially reasonable solutions.

In one embodiment, singular value decomposition (SVD) is employed for this process. SVD identifies the direction that is optimally correlated with the gene weights computed from an individual model and determines the final consensus weights by projecting the gene weights onto the optimal direction. The weight of each individual marker, e.g., the gene weight, is obtained from the "loading" number as described in the basic PLSR algorithm. A consensus weighting, e.g., using the SVD method, of features, e.g., genes whose expression level is correlated with outcome, e.g., IC50, can be forward, i.e., selecting the top values, e.g., the features, such as one or more than one gene whose expression is most closely related to outcome, or backward, i.e., discarding the bottom values, e.g., the features, such as one or more than one gene whose expression is least correlated with outcome. In a forward weighting method, the consensus begins with the highest weighted features, e.g., the top feature, the top 2 features, the top 3 features, the top 4 features, the top 5 features, the top 6 features, the top 8 features, the top 10 or more features, and adds one feature, e.g., gene, at a time. The process of adding features compares individual feature's weighting between the consensus weighting and each individual top model. Typically, since SVD captures the consistent trend or theme on the relative importance of each gene from individual lists of gene weights, the resulting consensus gene weights are better correlated with individual gene weights than any pair of individual gene weights are correlated with each other. The top model that shows the highest similarity to the consensus weightings can be selected as the representative model, the "core PLSR model", for later steps.

The core PLSR model can have about 100 to 1000, about 150 to 800, about 200 to 700, about 200 to 400, about 300 to 500, about 250 to 600, or about 400 to 700 markers, e.g., marker genes. This model is such that its sub-training subset trained model can successfully re-predict its sub-testing and sep-testing subsets. A way to check core PLSR model performance is by area under the receiving operator characteristic curve (AUC), a measure of discrimination when its threshold is varied, and Pearson correlation between the experimental and model predicted values for the samples, e.g., IC50 values, for samples, e.g., cell lines. The features, e.g., the marker genes, of the core PLSR model can be analyzed for biological pathway representation, e.g., canonical signaling pathways, which are over-represented. This pathway analysis, e.g., pathway enrichment analysis, can be performed by any of a number of computer programs, including METACORE™ software suite (GeneGo, Thomson Reuters, Carlsbad, Calif.) and IPA software (INGENUITY® Systems, Redwood City, Calif.). Over-represented pathways, e.g., signaling pathways, are identified from the features, e.g., marker genes, based on significance, e.g., a p-value cutoff, e.g., a p-value of less than 0.1, less than 0.075, less than 0.05, less than 0.025, less than 0.01, or less than 0.001 of the degree of association of markers, e.g., marker genes, in the core PLSR model, with the pathway. The higher the stringency of the cutoff, i.e., the lower the p-value, the fewer the markers selected from the pathways. The identification of the significantly over-represented pathways allows the selection of a subset of markers, e.g., marker genes, from the core PLSR model, which also are in the over-represented pathways. The markers from the core PLSR model which are not members of the over-represented pathways can be discarded from the final model. In one embodiment, all the markers that are not part of the pathways are discarded. The marker subset selection process results in a marker set which comprises about 20 markers, about 40 markers, about 50 markers, about 60 markers, about 75 markers, about 90 markers, about 40 to 70 markers, about 44 markers, about 51 markers, about 65 markers, or about 69 markers. The core PLSR model can then be re-trained and re-tested on the subset, e.g., the "pathway-based classifier", using the same sub-training, sub-testing, and sep-testing subsets as in the top model, e.g., to re-evaluate the subset's performance. The purpose of selecting this "pathway-based classifier" is to overlay a data-driven model built for a particular agent with canonical pathway information, to greatly reduce the size of the marker set at the same time as potentially enriching biological signals (as represented in canonical pathways). This pathway-based classifier, as a subset of the core PLSR model, reflects the common features of the entire training set. This approach is contrasted from methods which begin with pathways to merge genes into classifiers (Lee et al. (2008) PLoS Comput. Biol. 4:e1000217) before building models. The methods described herein use whole genome information to train a predictive model and find a core signature gene set and thus do not rely on pathway definition in selecting model genes. Additionally, signature genes could work collectively in over-represented pathways and multiple pathways may work together to define response to a therapeutic agent. As evaluated by AUC and correlation methods, such a "pathway-based classifier" may perform equally or sometimes slightly worse than a core PLSR model on the training dataset itself, but it can improve prediction performance on an independent testing dataset.

In one embodiment, the markers described herein, e.g., marker genes, can be identified by a method which comprises reducing the dataset size, selecting features from samples, training and testing features, e.g., by a combination of balanced and random splits, to identify top performing models, reducing the model number by removing overlaps, consensus weighting the features to find a core PLSR model most similar to the consensus, identifying over-representation of biological pathways among the features in the core PLSR model, and from the core features, selecting markers found in the over-represented pathways to yield a subset which retains common features of the entire training set. The markers can be used to predict outcome of treatment with a therapeutic agent on a new sample. The markers can be described herein, e.g., selected from the group of markers identified in Table 1, Table 2 and Table 3, or can be obtained from other datasets, including samples from other tissues, e.g. other tumor types, or samples from treatment with other therapeutic agents, e.g., other NAE inhibitors or EGFR inhibitors.

Use of Biomarkers to Predict Responsiveness to a Therapeutic Agent

Markers described herein or identified from the methods described above can be compared with characteristics of a sample, e.g., a new cell, tissue or diseased tissue, e.g., a tumor, e.g., from a patient, e.g., a cancer patient, e.g. a human, to predict outcome after treatment by a therapeutic agent, e.g., an NAE inhibitor or an EGFR inhibitor.

Markers, e.g., marker genes, are analyzed for a correlation between the characteristic, e.g., expression level and association with outcome, e.g., IC50, in the samples, e.g., cell lines or patient samples, used to identify the markers, e.g., through a PLSR method as described herein. This process can identify which markers are highly expressed in samples which were sensitive to the agent or associated with a favorable outcome and which markers are highly expressed in samples which were resistant to the agent or associated with an unfavorable outcome. The samples, e.g., cell lines, set aside from the model building splitting, e.g., the sep-testing subset, can be used to test the markers, e.g., as described herein, or marker set, e.g., a pathway-based classifier built from the method described above or a marker set comprising one or more markers selected from the group of markers identified in Table 1, Table 2 and Table 3. A correlation, e.g., represented by a score, is derived, e.g., by consensus weighting in a PLSR method, from the outcome predicted by the markers and the outcome observed in the sep-testing samples. A review of the correlation helps determine a separation between sensitive or favorable outcome samples and resistant or unfavorable outcome samples. That separation is chosen as a cutoff value to be used in prediction of new samples. The cutoff value is specific for the agent whose treatment data was used to build the model, or agents with a similar mechanism of action or which bind to the same target.

There are several ways to associate characteristics of a sample with outcome. For example, outcome results in cell numbers can be expressed as EC50 values (e.g., after measurement of cell numbers, the EC50 concentration can be calculated from the inflection point of a curve of percent of control (POC) against log of inhibitor concentration) or IC50 values (e.g., from the POC-log inhibitor plot, IC50 is the concentration at 50% maximal possible response). Outcome results in biochemical measures can be expressed as apoptosis (e.g., measurement of activation of caspase 3 plotted against log of inhibitor concentration, determined as the concentration for >5 fold induction), mitotic activity (e.g., determined by measuring the fold increase of phospho-histone 3) or metabolic activity (e.g., measuring the amount of fatty acid synthesis). Association of characteristics with outcome also can be based on clinical data, such as response, time-to-progression, progression-free survival or overall survival.

Since a cell line panel can contain a mixture of cancer types, correlations from the panel can reasonably represent a true cutoff, e.g., to predict a small number of samples. If there are a reasonable number of samples from patients, e.g., in a clinical trial, the cutoff might not represent a true cutoff, because the patients may have only a single type of cancer and its sample population may not be the same as the cell line panel. In that case, the cutoff from a cell line panel may still be used as a second best separation cutoff or used to check the new population-derived separation point, i.e., a new separation cutoff.

Characteristics of new samples, e.g., new test samples, e.g., cells, tissues, e.g., tumors, may have been measured on platforms that are not the same as the platform used to identify markers, e.g., as described herein. In that case, the markers can be compared to the features on the different platform to identify overlapping markers, e.g., marker genes. Once the overlapping markers are identified, the platform of the testing dataset is normalized against the platform of the training dataset, e.g., in a quantile-based normalization, to allow comparison of the characteristics, e.g., expression levels, between the samples used to identify the markers, e.g., the markers described herein and the samples for which outcome prediction is desired. Then, the model is re-trained and re-tested on the training dataset using the overlapping markers. This identifies markers that represent the markers described herein, or derived from methods described herein, e.g., a marker set, which are applicable to the dataset generated on the new platform.

To make the prediction, the information on the characteristics, e.g. expression level, of a marker, e.g., marker gene in each new, test sample is used as input for the PLSR model algorithm. This results in a predicted outcome score, expressed in the format of the outcome results described experimentally or clinically, such as described above. The outcome score is compared to the cutoff derived from separating sensitive and resistant samples. In the case of using IC50 values as measures of response to an agent, a low IC50 value (as well as a low PLSR predicted score) is associated with sensitivity to the agent, while a high IC50 value (as well as a high PLSR predicted score) is associated with resistance to the agent. A new sample whose score is above the cutoff value is associated with resistance or unfavorable outcome; a new sample whose score is below the cutoff value is associated with sensitivity or favorable outcome of treatment with the agent, e.g., an NAE inhibitor or EGFR inhibitor. Thus, a patient whose sample, e.g., tumor sample, generates a score associated with sensitivity would be predicted to benefit from treatment with the agent, e.g., an NAE inhibitor or an EGFR inhibitor. A patient whose sample, e.g., tumor sample, generates a score associated with resistance would be predicted not to benefit from treatment with the agent, e.g., an NAE inhibitor or EGFR inhibitor.

A separation cutoff for each inhibitor has a characteristic range, depending on the potency of the inhibitor. In the case of an outcome measure using IC50, such as $\log_2(IC50)$, the score is expressed as a log of the exponent, and can either positive or negative values. An example of a range of $\log_2(IC50)$ scores is be −3 (more potent) to +3 (less potent). In some embodiments, the $\log_2(IC50)$ separation cutoff score for an NAE inhibitor is in the range of −3 to 1 or −2.5 to 0.5. In some embodiments, the $\log_2(IC50)$ separation cutoff score of an EGFR inhibitor is in the range of 0.0 to 1.0. In some embodiments, the $\log_2(IC50)$ separation cutoff score of a pan-kinase inhibitor is in the range of 1.0 to 2.5.

In some embodiments, the $\log_2(IC50)$ separation cutoff score of MLN4924 is in the range of −1.6 to −1.3. In an embodiment, the $\log_2(IC50)$ separation cutoff score of MLN4924 is −1.45. In some embodiments, a subject will be treated with an NAE inhibitor if the $\log_2(IC50)$ of the sample is below −1.0. In some embodiments, a subject will be treated with an NAE inhibitor if the $\log_2(IC50)$ of the sample is below −0.5. In some embodiments, a subject will be treated with an NAE inhibitor if the $\log_2(IC50)$ of the sample is below 0.5. In some embodiments, a subject will not be treated with an NAE inhibitor if the $\log_2(IC50)$ of the sample is above 0.0. The lower the score used in the prediction will be more stringent and predict for the most sensitive subjects. Use of a low separation cutoff score in the clinic can increase the probability that patients identified to benefit from the inhibitor will successfully respond to treatment with the inhibitor. A higher score will be a less stringent prediction and use in the clinic will open the possibility of a range of responses by patients, with some who are predicted closer to the higher cutoff score not benefiting from treatment or having a less robust response. Use of a high separation cutoff score, such as a range of −1 to 0 in the case of $\log_2(IC50)$ of an NAE inhibitor, can identify patients who will not likely benefit from treatment or will need a stronger regimen with the inhibitor or a supplemental therapeutic agent in addition to the treatment regimen. Examples of separation cutoff scores can be found in the Examples and in the vertical lines of the FIGS. 5, 6 and 7 and in the horizontal line of FIG. 9.

In summary, items needed for one skilled in the art to make a prediction include: (A) A PLSR model, e.g., marker gene or marker gene set, e.g., markers identified in Table 1, Table 2 or Table 3 or obtained from the training dataset by the methods described herein; (B) A PLSR cutoff (or a table if there are multiple potential cutoffs) generated from the training dataset; (C) values of the characteristics measured for the marker gene or each marker gene in the set, e.g., gene expression results for the testing dataset, i.e., from the sample to be tested; and (D) a computer program, such as the R software package, which can perform a PLSR algorithm, calculate the score from the values in (C). One can evaluate whether the score generated by the computer program using the PLSR model is above or below the cutoff, thereby determining whether the patient whose sample was tested will have an unfavorable outcome or favorable outcome of treatment with an agent.

Samples and Feature Measurement

Described herein is the assessment of outcome for treatment of a tumor through measurement of the amount of pharmacogenomic markers. Also described are assessing the outcome by noninvasive, convenient or low-cost means. The invention provides methods for determining, assessing, advising or providing an appropriate therapy regimen for treating a tumor or managing disease in a patient. Monitoring a treatment using the kits and methods disclosed herein can identify the potential for unfavorable outcome and allow their prevention, and thus a savings in morbidity, mortality and treatment costs through adjustment in the therapeutic regimen, cessation of therapy or use of alternative therapy.

As used herein, the term "noninvasive" refers to a procedure which inflicts minimal harm to a subject. In the case of clinical applications, a noninvasive sampling procedure can be performed quickly, e.g., in a walk-in setting, typically without anaesthesia and/or without surgical implements or suturing. Examples of noninvasive samples include blood, serum, saliva, sputum, nipple aspirate, urine, buccal swabs, throat cultures, stool samples and cervical smears. Noninvasive diagnostic analyses include x-rays, magnetic resonance imaging, positron emission tomography, etc.

The term "sample" is intended to include a cell in culture or a cell line, a patient sample, e.g, tissue, cells, biopsy, biological fluids and isolates thereof, isolated from a subject, as well as tissues, cells and fluids present within a subject and can be obtained from a patient or a normal subject. A sample can be used for genotype or phenotype, e.g., histological, biochemical or elemental analysis. In hematological tumors of the bone marrow, e.g., myeloma tumors, primary analysis of the tumor can be performed on bone marrow samples. However, some tumor cells, (e.g., clonotypic tumor cells, circulating endothelial cells), are a percentage of the cell population in whole blood. These cells also can be mobilized into the blood during treatment of the patient with granulocyte-colony stimulating factor (G-CSF) in preparation for a bone marrow transplant, a standard treatment for hematological tumors, e.g., leukemias, lymphomas and myelomas. Examples of circulating tumor cells in multiple myeloma have been studied e.g., by Pilarski et al. (2000) Blood 95:1056-65 and Rigolin et al. (2006) Blood 107:2531-5. Thus, noninvasive samples, e.g., for in vitro measurement of markers to determine outcome of treatment, can include peripheral blood samples. Accordingly, cells within peripheral blood can be tested for marker amount. For patients with hematological tumors, a control, reference sample for normal characteristic, e.g., size, sequence, composition or amount can be obtained from skin or a buccal swab of the patient. For solid tumors, a typical tumor sample can be a biopsy of the tumor. Alternatively, a sample of tumor cells shed or scraped from the tumor site can be collected noninvasively, such as in blood, sputum, a nipple aspirate, urine, stool, cervical smear, etc. In some embodiments, a biopsy sample can be cultured as an in vitro explant, which is later used as a sample, or can be transferred to an immunocompromised animal model, e.g., as a xenograft, e.g., a primary tumor xenograft which is later used as a sample. For solid tumors, a control reference sample for normal characteristic, e.g., size, sequence, composition or amount can be obtained from blood of the patient.

Blood collection containers can comprise an anti-coagulant, e.g., heparin or ethylene-diaminetetraacetic acid (EDTA), sodium citrate or citrate solutions with additives to preserve blood integrity, such as dextrose or albumin or buffers, e.g., phosphate. If the amount of marker is being measured by measuring the level of its DNA in the sample, a DNA stabilizer, e.g., an agent that inhibits DNAse, can be added to the sample. If the amount of marker is being measured by measuring the level of its RNA in the sample, an RNA stabilizer, e.g., an agent that inhibits RNAse, can be added to the sample. If the amount of marker is being measured by measuring the level of its protein in the sample, a protein stabilizer, e.g., an agent that inhibits proteases, can be added to the sample. An example of a blood collection container is PAXGENE® tubes (PREANALYTIX, Valencia, Calif.), useful for RNA stabilization upon blood collection. Peripheral blood samples can be modified, e.g., fractionated, sorted or concentrated (e.g., to result in samples enriched with tumor or depleted of tumor (e.g., for a reference sample)). Examples of modified samples include clonotypic myeloma cells, which can be collected by e.g., negative selection, e.g., separation of white blood cells from red blood cells (e.g., differential centrifugation through a dense sugar or polymer solution (e.g., FICOLL® solution (Amersham Biosciences division of GE healthcare, Piscataway, N.J.) or HISTOPAQUE®-1077 solution, Sigma-Aldrich Biotechnology LP and Sigma-Aldrich Co., St. Louis, Mo.)) and/or positive selection by binding B cells to a selection agent (e.g., a reagent which binds to a tumor cell or myeloid progenitor marker, such as CD34, CD38, CD138, or CD133, for direct isolation (e.g., the application of a magnetic field to solutions of cells comprising magnetic beads (e.g., from Miltenyi Biotec, Auburn, Calif.) which bind to the B cell markers) or fluorescent-activated cell sorting).

Alternatively, a sample of a cell line, e.g., a tumor cell line, e.g., OCI-Ly3, OCI-Ly10 cell (Alizadeh et al. (2000) Nature 403:503-511), a RPMI 6666 cell, a SUP-B15 cell, a KG-1 cell, a CCRF-SB cell, an 8ES cell, a Kasumi-1 cell, a Kasumi-3 cell, a BDCM cell, an HL-60 cell, a Mo-B cell, a JM1 cell, a GA-10 cell or a B-cell lymphoma (e.g., BC-3) or a cell line or a collection of tumor cell lines (see e.g., McDermott et al. (2007) PNAS 104:19936-19941 or ONCOPANEL™ anti-cancer tumor cell profiling screen (Ricerca Biosciences, Bothell, Wash.)) can be assayed. A skilled artisan readily can select and obtain the appropriate cells (e.g., from American Type Culture Collection (ATCC®), Manassas, Va.) that are used in the present method. If the compositions or methods are being used to predict outcome of treatment in a patient or monitor the effectiveness of a therapeutic protocol, then a tissue or blood sample having been obtained from the patient being treated is a useful source of cells or marker gene or gene products for an assay.

The sample, e.g., tumor, e.g., biopsy or bone marrow, blood or modified blood, or other noninvasive cell sample (e.g., comprising tumor cells) and/or the reference, e.g., matched control (e.g., germline), sample can be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

The characteristic of a marker of the invention in a sample (e.g., a bone marrow sample, a tumor biopsy or a reference sample) from a test subject may be assessed by any of a wide variety of well known methods for detecting or measuring the characteristic, e.g., of a nucleic acid (e.g., RNA, mRNA, genomic DNA, or cDNA) and/or translated protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods. These methods include gene array/chip technology, RT-PCR, TAQMAN® gene expression assays (Applied Biosystems, Foster City, Calif.), e.g., under GLP approved laboratory conditions, in situ hybridization, immunohistochemistry, immunoblotting, FISH (flourescence in situ hybridization), FACS analyses, northern blot, southern blot, INFINIUM® DNA analysis Bead Chips (Illumina, Inc., San Diego, Calif.), quantitative PCR, bacterial artificial chromosome arrays, single nucleotide polymorphism (SNP) arrays (Affymetrix, Santa Clara, Calif.) or cytogenetic analyses. The detection methods of the invention can thus be used to detect RNA, mRNA, protein, cDNA, or genomic DNA, for example, in a sample in vitro as well as in vivo. Furthermore, in vivo techniques for detection of a polypeptide or nucleic acid corresponding to a marker of the invention include introducing into a subject a labeled probe to detect the biomarker, e.g., a nucleic acid complementary to the transcript of a biomarker or a labeled antibody, Fc receptor or antigen directed against the polypeptide, e.g., wild type or mutant marker. For example, the antibody can be labeled with a radioactive isotope whose presence and location in a subject can be detected by standard imaging techniques. These assays can be conducted in a variety of ways. A skilled artisan can select from these or other appropriate and available methods based on the nature of the marker(s), tissue sample and mutation in question. Some methods are described in more detail in later sections. Different methods or combinations of methods could be appropriate in different cases or, for instance in different types of tumors or patient populations.

In an embodiment, mRNA corresponding to the marker can be analyzed both by in situ and by in vitro formats in a sample using methods known in the art. An example of a method for measuring expression level is included in the Examples. Many expression detection methods use isolated RNA. For in vitro methods, any RNA isolation technique that does not select against the isolation of mRNA can be utilized for the purification of RNA from tumor cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155). RNA can be isolated using standard procedures (see e.g., Chomczynski and Sacchi (1987) *Anal. Biochem.* 162:156-159), solutions (e.g., trizol, TRI REAGENT® (Molecular Research Center, Inc., Cincinnati, Ohio; see U.S. Pat. No. 5,346,994) or kits (e.g., a QIAGEN® Group RNEASY® isolation kit (Valencia, Calif.) or LEUKOLOCK™ Total RNA Isolation System, Ambion division of Applied Biosystems, Austin, Tex.).

Additional steps may be employed to remove DNA from RNA samples. Cell lysis can be accomplished with a non-ionic detergent, followed by microcentrifugation to remove the nuclei and hence the bulk of the cellular DNA. DNA subsequently can be isolated from the nuclei for DNA analysis. In one embodiment, RNA is extracted from cells of the various types of interest using guanidinium thiocyanate lysis followed by CsCl centrifugation to separate the RNA from DNA (Chirgwin et al. (1979) *Biochemistry* 18:5294-99). Poly(A)+RNA is selected by selection with oligo-dT cellulose (see Sambrook et al. (1989) *Molecular Cloning—A Laboratory Manual* (2nd ed.), Cold Spring Harbor Laboratory, Cold Spring Harbor, N.Y.). Alternatively, separation of RNA from DNA can be accomplished by organic extraction, for example, with hot phenol or phenol/chloroform/isoamyl alcohol. If desired, RNAse inhibitors may be added to the lysis buffer. Likewise, for certain cell types, it may be desirable to add a protein denaturation/digestion step to the protocol. For many applications, it is desirable to enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or SEPHADEX® medium (see Ausubel et al. (1994) *Current Protocols In Molecular Biology*, vol. 2, Current Protocols Publishing, New York). Once bound, poly(A)+mRNA is eluted from the affinity column using 2 mM EDTA/0.1% SDS.

In another embodiment, a mutation in a marker can be identified by sequencing a nucleic acid, e.g., a DNA, RNA, cDNA or a protein correlated with the marker gene. There are several sequencing methods known in the art to sequence nucleic acids. A primer can be designed to bind to a region comprising a potential mutation site or can be designed to complement the mutated sequence rather than the wild type sequence. Primer pairs can be designed to bracket a region comprising a potential mutation in a marker gene. A primer or primer pair can be used for sequencing one or both strands of DNA corresponding to the marker gene. A primer can be used in conjunction with a probe to amplify a region of interest prior to sequencing to boost sequence amounts, e.g., for detection of a mutation in a marker gene. Examples of regions which can be sequenced include an entire gene, transcripts of the gene and a fragment of the gene or the transcript, e.g., one or more of exons or untranslated regions. Examples of mutations to target for primer selection and sequence or composition analysis can be found in public databases which collect mutation information, such as COSMIC and dbGaP.

Sequencing methods are known to one skilled in the art. Examples of methods include the Sanger method, the SEQUENOM™ method and Next Generation Sequencing (NGS) methods. The Sanger method, comprising using electrophoresis, e.g., capillary electrophoresis to separate primer-elongated labeled DNA fragments, can be automated for high-throughput applications. The primer extension sequencing can be performed after PCR amplification of regions of interest. Software can assist with sequence base calling and with mutation identification. SEQUENOM™ MASSARRAY® sequencing analysis (San Diego, Calif.) is a mass-spectrometry method which compares actual mass to expected mass of particular fragments of interest to identify mutations. NGS technology (also called "massively parallel sequencing" and "second generation sequencing") in general provides for much higher throughput than previous methods and uses a variety of approaches (reviewed in Zhang et al. (2011) *J. Genet. Genomics* 38:95-109 and Shendure and Hanlee (2008) *Nature Biotech.* 26:1135-1145). NGS methods can identify low frequency mutations in a marker in a sample. Some NGS methods (see, e.g., GS-FLX Genome Sequencer (Roche Applied Science, Branford, Conn.), Genome analyzer (Illumina, Inc. San Diego, Calif.) SOLID™ analyzer (Applied Biosystems, Carlsbad, Calif.), Polonator G.007 (Dover Systems, Salem, N.H.), HELISCOPE™ (Helicos Biosciences Corp., Cambridge, Mass.)) use cyclic array sequencing, with or without clonal amplification of PCR products spatially separated in a flow cell and various schemes to detect the labeled modified nucleotide that is incorporated by the sequencing enzyme (e.g., polymerase or ligase). In one NGS method, primer pairs can be used in PCR reactions to amplify regions of interest. Amplified regions can be ligated into a concatenated product. Clonal libraries are generated in the flow cell from the PCR or ligated products and further amplified ("bridge" or "cluster" PCR) for single-end sequencing as the polymerase adds a labeled, reversibly terminated base that is imaged in one of four channels, depending on the identity of the labeled base and then removed for the next cycle. Software can aid in the comparison to genomic sequences to identify mutations.

Composition or amounts of proteins and nucleic acids can be determined by many ways known in the art, such as by treating them in ways that cleave, degrade or digest them and then analyzing the components. Mass spectrometry, electrophoresis and chromatography can separate and define components for comparison. Mutations which cause deletions or insertions can be identified by size or charge differences in these methods. Protein digestion or restriction enzyme nucleic acid digestion can reveal different fragment patterns after some mutations. Antibodies that recognize particular marker proteins or mutant amino acids in their structural contexts can identify, detect and quantify the marker proteins or mutations in samples.

In an embodiment, DNA, e.g., genomic DNA corresponding to the wild type or mutated marker can be analyzed both by in situ and by in vitro formats in a sample using methods known in the art. DNA can be directly isolated from the sample or isolated after isolating another cellular component, e.g., RNA or protein. Kits are available for DNA isolation, e.g., QIAAMP® DNA Micro Kit (Qiagen, Valencia, Calif.). DNA also can be amplified using such kits.

In vitro techniques for detection of a polypeptide corresponding to a marker of the invention include enzyme linked immunosorbent assays (ELISAs), Western blots, protein array, immunoprecipitations and immunofluorescence. In such examples, expression of a marker is assessed using an antibody (e.g., a radio-labeled, chromophore-labeled, fluorophore-labeled, or enzyme-labeled antibody), an antibody derivative (e.g., an antibody conjugated with a substrate or with the protein or ligand of a protein-ligand pair (e.g., biotin-streptavidin)), or an antibody fragment (e.g., a single-chain antibody, an isolated antibody hypervariable domain, etc.) which binds specifically with a marker protein or fragment thereof, e.g., a protein or fragment comprising a region which can be mutated or a portion comprising a mutated sequence, or a mutated residue in its structural context, including a marker protein which has undergone all or a portion of its normal post-translational modification. An antibody can detect a protein with an amino acid sequence selected from the group consisting of the amino acid sequences identified in Table 1, Table 2 and Table 3. Residues listed as mutated in public databases such as COSMIC of dbGaP can be prepared in immunogenic compositions for generation of antibodies that will specifically recognize and bind to the mutant residues. Another method can employ pairs of antibodies, wherein one of the pair would bind a marker protein upstream, i.e. N-terminal to the region of expected mutation, e.g., nonsense or deletion and the other of the pair would bind the protein downstream. Wild type protein would bind both antibodies of the pair, but a protein with a nonsense or deletion mutation would bind only the N-terminal antibody of the pair. An assay such as a sandwich ELISA assay could detect a loss of quantity of the wild type protein in the tumor sample, e.g., in comparison to the reference sample, or a standard ELISA would comparison of the levels of binding of the antibodies to infer that a mutation is present in a tumor sample.

Indirect methods for determining the amount or functionality of a protein marker also include measurement of the activity of the protein. For example, a sample, or a protein isolated from the sample or expressed from nucleic acid isolated, cloned or amplified from the sample can be assessed for marker protein activity. For example activity of a marker in a signaling pathway can be measured by its ability to associate with binding partners, e.g., in a cell-free assay or in a cell-based assay.

In one embodiment, expression of a marker is assessed by preparing mRNA/cDNA (i.e., a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide. Expression of one or more markers likewise can be detected using quantitative PCR to assess the level of expression of the marker(s). An example of the use of measuring mRNA levels is that an inactivating mutation in a marker gene can result in an altered level of mRNA in a cell. The level can be upregulated due to feedback signaling protein production in view of nonfunctional or absent protein or downregulated due to instability of an altered mRNA sequence. Alternatively, any of the many known methods of detecting mutations or variants (e.g. single nucleotide polymorphisms, deletions, etc., discussed above) of a marker of the invention may be used to detect occurrence of a mutation in a marker gene in a patient.

An example of direct measurement is quantification of transcripts. As used herein, the level or amount of expression refers to the absolute amount of expression of an mRNA encoded by the marker or the absolute amount of expression of the protein encoded by the marker. As an alternative to making determinations based on the absolute expression amount of selected markers, determinations may be based on normalized expression amounts. Expression amount can be normalized across the genome in the array as described above, by comparison to a smaller group of control gene expression or by normalized expression of the marker in multiple samples. Such normalization allows one to compare the expression level in one sample, to another sample, e.g., between samples from different times or different subjects. Further, after normalization, the expression level can be provided as a relative expression level. Correcting the absolute expression level of a marker can occur by comparing its expression to the expression of a control marker that is not a marker, e.g., in a housekeeping role that is constitutively expressed. Suitable markers for normalization also include housekeeping genes, such as the actin gene or beta-2 microglobulin. Reference markers for data normalization purposes include markers which are ubiquitously expressed and/or whose expression is not regulated by oncogenes. Constitutively expressed genes are known in the art and can be identified and selected according to the relevant tissue and/or situation of the patient and the analysis methods. An alternative method to determine the baseline of expression of a marker or marker set, the amount of the marker or markers in a marker set is determined for at least 1, or 2, 3, 4, 5, or more samples, e.g., 7, 10, 15, 20 or 50 or more samples in order to establish a baseline, e.g., the mean amount or level of each of the markers. The amount of the marker or markers in a marker set determined for the test sample (e.g., absolute level of expression) is then divided by the baseline value obtained for that marker or markers in the marker set. This provides a relative amount and aids in identifying abnormal levels of marker expression or protein activity. The baseline of a genomic DNA sample, e.g., diploid copy number, can be determined by measuring amounts in cells from subjects without a tumor or in non-tumor cells from the patient.

Probes based on the sequence of a nucleic acid molecule of the invention can be used to detect transcripts or genomic sequences corresponding to one or more markers of the invention. The probe can comprise a label group attached thereto, e.g., a radioisotope, a fluorescent compound, an enzyme, or an enzyme co-factor. Such probes can be used as part of a diagnostic test kit for identifying cells or tissues which express the protein, such as by measuring levels of a nucleic acid molecule encoding the protein in a sample of cells from a subject, e.g., detecting mRNA levels or determining whether a gene encoding the protein has been mutated or deleted.

In addition to the nucleotide sequences described in the database records described herein, it will be appreciated by those skilled in the art that DNA sequence polymorphisms that lead to changes in the amino acid sequence can exist within a population (e.g., the human population). Such genetic polymorphisms can exist among individuals within a population due to naturally occurring allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

Primers or nucleic acid probes comprise a nucleotide sequence complementary to a specific a marker or a mutated region thereof and are of sufficient length to selectively hybridize with a marker gene or nucleic acid associated with a marker gene. Primers and probes can be used to aid in the isolation and sequencing of marker nucleic acids. The length of a nucleic acid probe or primer can be at least 10 nucleotides, at least 12 nucleotides, at least 15 nucleotides, at least 17 nucleotides, at least 20 nucleotides, at least 22 nucleotides, at least 25 nucleotides, at least 30 nucleotides or at least 40 nucleotides. The probe or primer can comprise consecutive nucleotides of a marker gene sequence or a complement thereof. In one embodiment, the primer or nucleic acid probe, e.g., a substantially purified oligonucleotide, comprises a region having a nucleotide sequence which hybridizes under stringent conditions to about 6, 8, 10, 12, 15, 20, 25, 30, 40, 50, 60, 75, 100, 150, 200 or more consecutive nucleotides or to the entire length of a marker nucleic acid. In another embodiment, the primer or nucleic acid probe is capable of hybridizing to a marker nucleic acid comprising a nucleotide sequence of a sequence identified in Table 1, Table 2 or Table 3, or a complement of any of the sequences. For example, a primer or nucleic acid probe comprising a nucleotide sequence of at least about 15 consecutive nucleotides, at least about 25 nucleotides, at least about 30 nucleotides or having from about 15 to about 20 nucleotides of a sequence identified in Table 1, Table 2 or Table 3, or a complement of any of the sequences are provided by the invention. Primers or nucleic acid probes having a sequence of more than about 30 nucleotides are also within the scope of the invention. In another embodiment, a primer or nucleic acid probe can have a sequence at least 70%, at least 75%, 80% or 85%, or at least, 90%, 95% or 97% identical to the nucleotide sequence of any sequence of a sequence identified in Table 1, Table 2 or Table 3, or a complement of any of the sequences. Nucleic acid analogs can be used as binding sites for hybridization. An example of a suitable nucleic acid analogue is peptide nucleic acid (see, e.g., Egholm et al., *Nature* 363:566 568 (1993); U.S. Pat. No. 5,539,083).

Primers or nucleic acid probes can be selected using an algorithm that takes into account binding energies, base composition, sequence complexity, cross-hybridization binding energies, and secondary structure (see Friend et al., International Patent Publication WO 01/05935, published Jan. 25, 2001; Hughes et al., *Nat. Biotech.* 19:342-7 (2001). Useful primers or nucleic acid probes of the invention bind sequences which are unique for each transcript, e.g., target mutated regions and can be used in PCR for amplifying, detecting and sequencing only that particular nucleic acid, e.g., transcript or mutated transcript. Examples of mutations of genes are described in reference articles cited herein and in public databases described herein. Computer programs that are well known in the art are useful in the design of primers with the required specificity and optimal amplification properties, such as Oligo version 5.0 (National Biosciences, Plymouth, Minn.). While perfectly complementary nucleic acid probes and primers can be used for detecting the markers described herein and mutants, polymorphisms or alleles thereof, departures from complete complementarity are contemplated where such departures do not prevent the molecule from specifically hybridizing to the target region. For example, an oligonucleotide primer may have a non-complementary fragment at its 5' end, with the remainder of the primer being complementary to the target region. Alternatively, non-complementary nucleotides may be interspersed into the nucleic acid probe or primer as long as the resulting probe or primer is still capable of specifically hybridizing to the target region.

Markers can be studied in combination with another measure of treatment outcome, e.g., biochemical markers (e.g., M protein, proteinuria) or histology markers (e.g., blast count, number of mitotic figures per unit area). Markers can be measured from samples obtained at different periods, e.g., before or after beginning treatment with an agent. A Fisher exact test (p-value=$\Sigma P(X=x)$ from x=1 to the number of situations, e.g., mutations, tested that show sensitivity to NAE or EGFR inhibition) for testing significance of data of small sample sizes, whether different characteristics of a marker gene are associated in the same direction with outcome or whether there is an association between a characteristic of a marker or markers in a marker set and biochemical markers or histology markers. The observed change from baseline at the last (or other) time point could be analyzed using a paired t-test.

A difference in amount from one timepoint to the next or from the tumor sample to the normal sample can indicate prognosis of treatment outcome. A baseline level can be determined by measuring expression at 1, 2, 3, 4, or more times prior to treatment, e.g., at time zero, one day, three days, one week and/or two weeks or more before treatment. Alternatively, a baseline level can be determined from a number of subjects, e.g., normal subjects or patients with the same health status or disorder, who do not undergo or have not yet undergone the treatment, as discussed above. Alternatively, one can use expression values deposited with the Gene Expression Omnibus (GEO) program at the National Center for Biotechnology Information (NCBI, Bethesda, Md.). For example, datasets of myeloma mRNA expression amounts sampled prior to proteasome inhibition therapy include GEO Accession number GSE9782, also analyzed in Mulligan, et al. (2006) *Blood* 109:3177-88 and GSE6477, also analyzed by Cling et al. (2007) *Cancer Res.* 67:292-9. To test the effect of the treatment on the tumor, the expression of the marker can be measured at any time or multiple times after some treatment, e.g., after 1 day, 2 days, 3 days, 5 days, 1 week, 2 weeks, 3 weeks, 4 weeks, 1 month, 2 months, 3 months and/or 6 or more months of treatment. For example, the amount of a marker can be measured once after some treatment, or at multiple intervals, e.g., 1-week, 2-week, 4-week or 2-month, 3-month or longer intervals during treatment. Conversely, to determine onset of progressive disease after stopping the administration of a therapeutic regimen, the amount of the marker can be measured at any time or multiple times after, e.g., 1 day, 2 days, 3 days, 5 days, 1 week, 2 weeks, 3 weeks, 4 weeks, 1 month, 2 months, 3 months and/or 6 or more months after the last treatment. One of skill in the art would determine the timepoint or timepoints to assess the amount of the marker depending on various factors, e.g., the pharmacokinetics of the treatment, the treatment duration, pharmacodynamics of the treatment, age of the patient, the nature of the disorder or mechanism of action of the treatment. A trend in the direction of unfavorable outcome upon scoring samples obtained from different times during NAE inhibition therapy or EGFR inhibition therapy indicates a decrease in response of the tumor to the therapy, e.g., increase in resistance, and another treatment protocol should be initiated to treat the patient. A trend toward a favorable outcome indicates usefulness of the therapeutic regimen or continued benefit of the therapy, so the treatment could continue.

Any marker, e.g., marker gene or combination of marker, e.g., marker genes of the invention, or mutations thereof as well as any known markers in combination with the markers, e.g., marker genes of the invention, may be used in the compositions, kits, and methods of the present invention. In general, markers are selected for as great as possible variance of the characteristic, e.g., size, sequence, composition or amount of the marker in samples comprising tumor cells. Although this variance can be as small as the limit of detection of the method for assessing the amount of the marker, in another embodiment, the difference can be at least greater than the standard error of the assessment method. In the case of RNA or protein amount, a difference can be at least 1.5-, 2-, 3-, 4-, 5-, 6-, 7-, 8-, 9-, 10-, 15-, 20-, 25-, 100-, 500-, 1000-fold or greater. "Low" RNA or protein amount can be that expression relative to the baseline is low. In the case of amount of DNA, e.g., copy number, the amount is 0, 1, 2, 3, 4, 5, 6, or more copies. A deletion causes the copy number to be 0 or 1; an amplification causes the copy number to be greater than 2. The difference can be qualified by a confidence level, e.g., $p<0.05$, $p<0.02$, $p<0.01$ or lower p-value.

Measurement of more than one marker, e.g., a set of 2, 3, 4, 5, 6, 7, 8, 9, 10, 12, 15, 20, 25, 30, 35, 40, 45, 50, 55, 60, 65, 70, 75 or more markers can provide an expression profile or a trend indicative of treatment outcome. In some embodiments, the marker set comprises no more than 2, 3, 4, 5, 6, 7, 8, 9, 10, 12, 15, 20, or 25 markers. In some embodiments, the marker set includes a plurality of marker genes, or a plurality of marker material corresponding to one or more marker genes (e.g., nucleic acid and protein, genomic DNA and mRNA, or various combinations of markers described herein). Analysis of treatment outcome through assessing the amount of markers in a set can be accompanied by a statistical method, e.g., a PLSR method as described herein which accounts for variables which can affect the contribution of the amount of a marker in the set to the class or trend of treatment outcome, e.g., the signal-to-noise ratio of the measurement or hybridization efficiency for each marker. A composition for analyzing a marker set, e.g., a set of 2, 3, 4, 5, 6, 7, 8, 9, 10, 12, 15, 20, 25, 30, 35, 40, 45, 50, 55, 60, 65, 70, 75 or more markers, can comprise a primer, probe or primers to analyze at least one marker nucleic acid described herein, e.g., a nucleic acid sequence identified in Table 1, Table 2 or Table 3, or a complement of any of the sequences. Compositions for analyzing selected marker sets can be assembled from the markers provided herein or selected from among markers using methods provided herein and analogous methods known in the art. A way to qualify a new marker for use in an assay of the invention is to correlate the relationship to outcome by calculating the coefficient of determination $r2$, after solving for r, the Pearson product moment correlation coefficient and/or preparing a least squares plot, using standard statistical methods. A correlation can analyze DNA copy number versus the level of expression of marker, e.g., a marker gene. A gene product can be selected as a marker if the result of the correlation ($r2$, e.g., the linear slope of the data in this analysis), is at least 0.1-0.2, at least 0.3-0.5, or at least 0.6-0.8 or more. Markers can vary with a positive correlation to response, TTP or survival (i.e., change expression levels in the same manner as copy number, e.g., decrease when copy number is decreased). Markers which vary with a negative correlation to copy number (i.e., change expression levels in the opposite manner as copy number levels, e.g., increase when copy number is decreased) provide inconsistent determination of outcome.

Another way to qualify a new marker for use in the assay would be to assay the expression of large numbers of markers in a number of subjects before and after treatment with a test agent. The expression results allow identification of the markers which show large changes in a given direction after treatment relative to the pre-treatment samples. One can build a repeated-measures linear regression model to identify the genes that show statistically significant changes or differences. To then rank these significant genes, one can calculate the area under the change from e.g., baseline vs time curve. This can result in a list of genes that would show the largest statistically significant changes. Then several markers can be combined together in a set by using such methods as principle component analysis, clustering methods (e.g., k-means, hierarchical), multivariate analysis of variance (MANOVA), or linear regression techniques. To use such a gene (or group of genes) as a marker, genes which show 2-, 2.5-, 3-, 3.5-, 4-, 4.5-, 5-, 7-, 10-fold, or more differences of expression from baseline would be included in the marker set. An expression profile, e.g., a composite of the expression level differences from baseline or reference of the aggregate marker set would indicate at trend, e.g., if a majority of markers show a particular result, e.g., a significant difference from baseline or reference, e.g., 60%, 70%, 80%, 90%, 95% or more markers; or more markers, e.g., 10% more, 20% more, 30% more, 40% more, show a significant result in one direction than the other direction.

In embodiments when the compositions, kits, and methods of the invention are used for characterizing treatment outcome in a patient, the marker or set of markers of the invention is selected such that a significant result is obtained in at least about 20%, at least about 40%, 60%, 70%, 80%, 85% or 90% or in substantially all patients treated with the test agent. The marker or set of markers of the invention can be selected such that a positive predictive value (PPV) of greater than about 10% is obtained for the general population and additional confidence in a marker can be inferred when the PPV is coupled with an assay specificity greater than 80%.

Therapeutic Agents

The markers and marker sets of the present invention assess the likelihood of favorable outcome of therapy (e.g., sensitivity to a therapeutic agent) in patients, e.g., cancer patients, e.g., patients having a hematological cancer (e.g., multiple myeloma, leukemias, lymphoma, etc) or solid tumor cancer (e.g., melanoma, esophageal cancer, bladder cancer, lung cancer, such as non-small cell lung cancer (NSCLC), adenocarcinoma of the lung, or lung metastases in the brain, pancreatic cancer or breast cancer), based on its ability to affect the characteristic, e.g., composition or amount of a marker or markers of the invention. Using this prediction, cancer therapies can be evaluated to design a therapy regimen best suitable for patients in either category.

In particular, the methods can be used to predict patient sensitivity to NAE inhibitors or EGFR inhibitors as described in earlier sections. The agents tested in the present methods can be a single agent or a combination of agents. The methods of the invention include combination of NAE inhibition therapy or EGFR inhibition therapy with proteasome inhibition therapy and/or other or additional agents, e.g., selected from the group consisting of chemotherapeutic agents. For example, the present methods can be used to determine whether a single chemotherapeutic agent, such as an NAE inhibitor (e.g., MLN4924) or an EGFR inhibitor, such as erlotinib, can be used to treat a cancer or whether a one or more agents should be used in combination with the NAE inhibitor (e.g., MLN4924) or EGFR inhibitor, e.g., erlotinib. Useful combinations can include agents that have different mechanisms of action, e.g., the use of an antimitotic agent in combination with an alkylating agent and an NAE inhibitor.

As used herein, the term "proteasome inhibitor" refers to any substance which directly inhibits enzymatic activity of the 20S or 26S proteasome in vitro or in vivo. In some embodiments, the proteasome inhibitor is a peptidyl boronic acid. Examples of peptidyl boronic acid proteasome inhibitors suitable for use in the methods of the invention are disclosed in Adams et al., U.S. Pat. No. 5,780,454 (1998), U.S. Pat. No. 6,066,730 (2000), U.S. Pat. No. 6,083,903 (2000); U.S. Pat. No. 6,297,217 (2001), U.S. Pat. No. 6,465,433 (2002), U.S. Pat. No. 6,548,668 (2003), U.S. Pat. No. 6,617,317 (2003), and U.S. Pat. No. 6,747,150 (2004), each of which is hereby incorporated by reference in its entirety, including all compounds and formulae disclosed therein. In some embodiments, the peptidyl boronic acid proteasome inhibitor is selected from the group consisting of: N (4 morpholine)carbonyl-β-(1-naphthyl)-L-alanine-L-leucine boronic acid; N (8 quinoline)sulfonyl-β-(1-naphthyl)-L-alanine-L-alanine-L-leucine boronic acid; N (pyrazine)carbonyl-L-phenylalanine-L-leucine boronic acid, and N (4 morpholine)¬ carbonyl-[O-(2-pyridylmethyl)]-L-tyrosine-L-leucine boronic acid. In a particular embodiment, the proteasome inhibitor is N (pyrazine)carbonyl-L-phenylalanine-L-leucine boronic acid (bortezomib; VELCADE®; formerly known as MLN341 or PS-341). Publications describe the use of the disclosed boronic ester and boronic acid compounds to reduce the rate of muscle protein degradation, to reduce the activity of NF-kB in a cell, to reduce the rate of degradation of p53 protein in a cell, to inhibit cyclin degradation in a cell, to inhibit the growth of a cancer cell, and to inhibit NF-kB dependent cell adhesion. Bortezomib specifically and selectively inhibits the proteasome by binding tightly (Ki=0.6 nM) to one of the enzyme's active sites. Bortezomib is selectively cytotoxic, and has a novel pattern of cytotoxicity in National Cancer Institute (NCI) in vitro and in vivo assays (Adams J, et al. Cancer Res (1999) 59:2615-22).

Additionally, proteasome inhibitors include peptide aldehyde proteasome inhibitors (Stein et al., U.S. Pat. No. 5,693,617 (1997); Siman et al., international patent publication WO 91/13904; Iqbal et al., J. Med. Chem. 38:2276-2277 (1995); and Iinuma et al., international patent publication WO 05/105826, each of which is hereby incorporated by reference in its entirety), peptidyl epoxy ketone proteasome inhibitors (Crews et al., U.S. Pat. No. 6,831,099; Smyth et al., international patent publication WO 05/111008; Bennett et al., international patent publication WO 06/045066; Spaltenstein et al. Tetrahedron Lett. 37:1343 (1996); Meng, Proc. Natl. Acad. Sci. 96: 10403 (1999); and Meng, Cancer Res. 59: 2798 (1999)), alpha-ketoamide proteasome inhibitors (Chatterjee and Mallamo, U.S. Pat. No. 6,310,057 (2001) and U.S. Pat. No. 6,096,778 (2000); and Wang et al., U.S. Pat. No. 6,075,150 (2000) and U.S. Pat. No. 6,781,000 (2004)), peptidyl vinyl ester proteasome inhibitors (Marastoni et al., J. Med. Chem. 48:5038 (2005), and peptidyl vinyl sulfone and 2-keto-1,3,4-oxadiazole proteasome inhibitors, such as those disclosed in Rydzewski et al., J. Med. Chem. 49:2953 (2006); and Bogyo et al., Proc. Natl. Acad. Sci. 94:6629 (1997)), azapeptoids and (Bouget et al., Bioorg. Med. Chem. 11:4881 (2003); Baudy-Floc'h et al., international patent publication WO 05/030707; and Bonnemains et al., international patent publication WO 03/018557), efrapeptin oligopeptides (Papathanassiu, international patent publication WO 05/115431), lactacystin and salinosporamide and analogs thereof (Fenteany et al., U.S. Pat. No. 5,756,764 (1998), U.S. Pat. No. 6,147,223 (2000), U.S. Pat. No. 6,335,358 (2002), and U.S. Pat. No. 6,645,999 (2003); Fenteany et al., Proc. Natl. Acad. Sci. USA (1994) 91:3358; Fenical et al., international patent publication WO 05/003137; Palladino et al., international patent publication WO 05/002572; Stadler et al., international patent publication WO 04/071382; Xiao and Patel, U.S. patent publication 2005/023162; and Corey, international patent publication WO 05/099687).

Additional therapeutic agents for use in combination with an NAE inhibitor (e.g., MLN4924) or EGFR inhibitor, e.g., erlotinib in the methods of the invention comprise a known class of therapeutic agents comprising glucocorticoid steroids. Glucocorticoid therapy generally comprises at least one glucocorticoid agent (e.g., dexamethasone). In certain applications of the invention, the agent used in methods of the invention is a glucocorticoid agent. One example of a glucocorticoid utilized in the treatment of multiple myeloma patients as well as other cancer therapies is dexamethasone. Additional glucocorticoids utilized in treatment of hematological and combination therapy in solid tumors include hydrocortisone, predisolone, prednisone, and triamcinolone.

Other therapeutic agents for use in combination with NAE inhibitors or EGFR inhibitors include examples of a variety of chemotherapeutic agents. A "chemotherapeutic agent" is intended to include chemical reagents which inhibit the growth of proliferating cells or tissues wherein the growth of such cells or tissues is undesirable. Chemotherapeutic agents such as anti-metabolic agents, e.g., Ara AC, 5-FU, gemcitabine and methotrexate, antimitotic agents, e.g., taxane, vinblastine and vincristine, alkylating agents, e.g., melphanlan, Carmustine (BCNU) and nitrogen mustard, Topoisomerase II inhibitors, e.g., VW-26, topotecan and Bleomycin, strand-breaking agents, e.g., doxorubicin and Mitoxantrone (DHAD), cross-linking agents, e.g., cisplatin and carboplatin (CBDCA), radiation and ultraviolet light and are well known in the art (see e.g., Gilman A. G., et al. The Pharmacological Basis of Therapeutics, 8th Ed., Sec 12:1202-1263 (1990)), and are typically used to treat neoplastic diseases. Examples of chemotherapeutic agents generally employed in chemotherapy treatments are listed below in Table 4.

TABLE 4

| | Chemotherapeutic Agents | |
|---|---|---|
| CLASS | TYPE OF AGENT | NONPROPRIETARY NAMES (OTHER NAMES) |
| Alkylating | Nitrogen Mustards | Mechlorethamine (HN$_2$) |
| | | Cyclophosphamide |
| | | Ifosfamide |
| | | Melphalan (L-sarcolysin) |
| | | Chlorambucil |
| | Ethylenimines And Methylmelamines | Hexamethylmelamine Thiotepa |
| | Alkyl Sulfonates | Busulfan |
| Alkylating | Nitrosoureas | Carmustine (BCNU) |
| | | Lomustine (CCNU) |
| | | Semustine (methyl-CCNU) |
| | | Streptozocin (streptozotocin) |
| Alkylating | Triazenes | Decarbazine (DTIC; dimethyltriazenoimi-dazolecarboxamide) |
| | Alkylator | cis-diamminedichloroplatinum II (CDDP) |
| Antimetabolites | Folic Acid Analogs | Methotrexate (amethopterin) |
| | Pyrimidine Analogs | Fluorouracil ('5-fluorouracil; 5-FU) |
| | | Floxuridine (fluorode-oxyuridine; FUdR) |
| | | Cytarabine (cytosine arabinoside) |
| | Purine Analogs and Related Inhibitors | Mercaptopuine (6-mercaptopurine; 6-MP) |
| | | Thioguanine (6-thioguanine; TG) |
| | | Pentostatin (2' - deoxycoformycin) |
| Natural Products | Vinca Alkaloids | Vinblastin (VLB) |
| | | Vincristine |
| | Topoisomerase Inhibitors | Etoposide |
| | | Teniposide |
| | | Camptothecin |
| | | Topotecan |
| | | 9-amino-campotothecin CPT-11 |
| | Antibiotics | Dactinomycin (actinomycin D) |
| | | Adriamycin |
| | | Daunorubicin (daunomycin; rubindomycin) |
| | | Doxorubicin |
| | | Bleomycin |
| | | Plicamycin (mithramycin) |
| | | Mitomycin (mitomycin C) |
| | | TAXOL |
| | | Taxotere |
| | Enzymes | L-Asparaginase |
| | Biological Response Modifiers | Interfon alfa |
| | | Interleukin 2 |
| Natural Products | Platinum Coordination Complexes | cis-diamminedichloroplatinum II (CDDP) |
| | | Carboplatin |
| | Anthracendione | Mitoxantrone |
| | Substituted Urea | Hydroxyurea |
| Miscellaneous Agents | Methyl Hydraxzine Derivative | Procarbazine (N-methylhydrazine,(MIH) |
| | Adrenocortical Suppressant | Mitotane (o,p'-DDD) |
| | | Aminoglutethimide |
| Hormones and Antagonists | Progestins | Hydroxyprogesterone caproate |
| | | Medroxyprogesterone acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| | Antiandrogen | Flutamide |
| | Gonadotropin-releasing Hormone analog | Leuprolide |

The agents disclosed herein may be administered by any route, including intradermally, subcutaneously, orally, intraarterially or intravenously. In one embodiment, administration will be by the intravenous route. Parenteral administration can be provided in a bolus or by infusion.

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. Treatments may be administered daily or more frequently depending upon a number of factors, including the overall health of a patient, and the formulation and route of administration of the selected compound(s).

Detection Methods

A general principle of prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay. One example of such an embodiment includes use of an array or chip which contains a predictive marker or marker set anchored for expression analysis of the sample.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite. One skilled in the art will know many other suitable carriers for binding antibody or antigen, and will be able to adapt such support for use with the present invention. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In an embodiment, the probe, when it is the unanchored assay component, can be labeled for the purpose of detection and readout of the assay, either directly or indirectly, with detectable labels discussed herein and which are well-known to one skilled in the art. The term "labeled", with regard to the probe (e.g., nucleic acid or antibody), is intended to encompass direct labeling of the probe by coupling (i.e., physically linking) a detectable substance to the probe, as well as indirect labeling of the probe by reactivity with another reagent that is directly labeled. An example of indirect labeling includes detection of a primary antibody using a fluorescently labeled secondary antibody. It is also possible to directly detect marker/probe complex formation without further manipulation or labeling of either component (marker or probe), for example by utilizing the technique of fluorescence energy transfer (FET, see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). As used herein, "BIA" or "surface plasmon resonance" is a technology for studying biospecific interactions in real time, without labeling any of the interactants (e.g., BIACORE™). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P. (1993) *Trends Biochem Sci.* 18:284-7). Standard chromatographic techniques also can be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H. (1998) *J. Mol. Recognit.* 11:141-8; Hage, D. S., and Tweed, S. A. (1997) *J. Chromatogr. B. Biomed. Sci. Appl.* 699:499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In some embodiments, non-denaturing gel matrix materials and conditions in the absence of reducing agent are used in order to maintain the binding interaction during the electrophoretic process. Appropriate conditions to the particular assay and components thereof will be well known to one skilled in the art.

The isolated mRNA can be used in hybridization or amplification assays that include, but are not limited to, Southern or Northern analyses, polymerase chain reaction and TAQMAN® gene expression assays (Applied Biosystems, Foster City, Calif.) and probe arrays. One diagnostic method for the detection of mRNA levels involves contacting the isolated mRNA with a nucleic acid molecule (probe) that can hybridize to the mRNA encoded by the gene being detected. Nucleic acids comprising mutations of marker genes can be used as probes or primers. The nucleic acid probes or primers of the invention can be single stranded DNA (e.g., an oligonucleotide), double stranded DNA (e.g., double stranded oligonucleotide) or RNA. Primers of the invention refer to nucleic acids which hybridize to a nucleic acid sequence which is adjacent to the region of interest and is extended or which covers the region of interest. A nucleic acid probe can be, for example, a full-length cDNA, or a portion thereof, such as an oligonucleotide of at least 7, 15, 20, 25, 30, 50, 75, 100, 125, 150, 175, 200, 250 or 500 or more consecutive nucleotides of the marker and sufficient to specifically hybridize under stringent conditions to a mRNA or genomic DNA encoding a marker of the present invention. The exact length of the nucleic acid probe will depend on many factors that are routinely considered and practiced by the skilled artisan. Nucleic acid probes of the invention may be prepared by chemical synthesis using any suitable methodology known in the art, may be produced by recombinant technology, or may be derived from a sample, for example, by restriction digestion. Other suitable probes for use in the diagnostic assays of the invention are described herein. The probe can comprise a label group attached thereto, e.g., a radioisotope, a fluorescent compound, an enzyme, an enzyme co-factor, a hapten, a sequence tag, a protein or an antibody. The nucleic acids can be modified at the base moiety, at the sugar moiety, or at the phosphate backbone. An example of a nucleic acid label is incorporated using SUPER™ Modified Base Technology (Nanogen, Bothell, Wash., see U.S. Pat. No. 7,045,610). The level of expression can be measured as general nucleic acid levels, e.g., after measuring the amplified DNA levels (e.g. using a DNA intercalating dye, e.g., the SYBR green dye (Qiagen Inc., Valencia, Calif.) or as specific nucleic acids, e.g., using a probe based design, with the probes labeled. TAQMAN® assay formats can use the probe-based design to increase specificity and signal-to-noise ratio.

Such primers or probes can be used as part of a diagnostic test kit for identifying cells or tissues which express the protein, such as by measuring amounts of a nucleic acid molecule transcribed in a sample of cells from a subject, e.g., detecting transcript, mRNA levels or determining whether a gene encoding the protein has been mutated or deleted. Hybridization of an RNA or a cDNA with the nucleic acid probe can indicate that the marker in question is being expressed. The invention further encompasses detecting nucleic acid molecules that differ, due to degeneracy of the genetic code, from the nucleotide sequence of nucleic acids encoding a marker protein (e.g., protein having a sequence identified in Table 1, Table 2 or Table 3), and thus encode the same protein. It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. Such natural allelic variations can typically result in 1-5% variance in the nucleotide sequence of a given gene. Alternative alleles can be identified by sequencing the gene of interest in a number of different individuals, e.g., normal samples from individuals. This can be readily carried out by using hybridization probes to identify the same genetic locus in a variety of individuals. Detecting any and all such nucleotide variations and resulting amino acid polymorphisms or variations that are the result of natural allelic variation and that do not alter the functional activity are intended to be within the scope of the invention. In addition, it will be appreciated that DNA polymorphisms that affect RNA expression levels can also exist that may affect the overall expression level of that gene (e.g., by affecting regulation or degradation).

As used herein, the term "hybridizes" is intended to describe conditions for hybridization and washing under which nucleotide sequences that are significantly identical or homologous to each other remain hybridized to each other. In some embodiments, the conditions are such that sequences at least about 70%, at least about 80%, at least about 85%, 90% or 95% identical to each other remain hybridized to each other for subsequent amplification and/or detection. Stringent conditions vary according to the length of the involved nucleotide sequence but are known to those skilled in the art and can be found or determined based on teachings in *Current Protocols in Molecular Biology*, Ausubel et al., eds., John Wiley & Sons, Inc. (1995), sections 2, 4 and 6. Additional stringent conditions and formulas for determining such conditions can be found in *Molecular Cloning: A Laboratory Manual*, Sambrook et al., Cold Spring Harbor Press, Cold Spring Harbor, N.Y. (1989), chapters 7, 9 and 11. A non-limiting example of stringent hybridization conditions for hybrids that are at least 10 basepairs in length includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A non-limiting example of highly stringent hybridization conditions for such hybrids includes hybridization in 1×SSC, at about 65-70° C. (or hybridization in 1×SSC plus 50% formamide at about 42-50° C.) followed by one or more washes in 0.3×SSC, at about 65-70° C. A non-limiting example of reduced stringency hybridization conditions for such hybrids includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. Another example of stringent hybridization conditions are hybridization in 6× sodium chloride/sodium citrate (SSC) at about 45° C., followed by one or more washes in 0.2×SSC, 0.1% SDS at 50-65° C. A further example of stringent hybridization buffer is hybridization in 1 M NaCl, 50 mM 2-(N-morpholino)ethanesulfonic acid (MES) buffer (pH 6.5), 0.5% sodium sarcosine and 30% formamide. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}$[Na$^+$])+0.41(% G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, polyvinylpyrrolidone (PVP) and the like. When using nylon membranes, in particular, an additional non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991-1995, (or alternatively 0.2×SSC, 1% SDS). A primer or nucleic acid probe can be used alone in a detection method, or a primer can be used together with at least one other primer or nucleic acid probe in a detection method. Primers can also be used to amplify at least a portion of a nucleic acid. Nucleic acid probes of the invention refer to nucleic acids which hybridize to the region of interest and which are not further extended. For example, a nucleic acid probe is a nucleic acid which specifically hybridizes to a mutant region of a biomarker, and which by hybridization or absence of hybridization to the DNA of a patient or the type of hybrid formed can be indicative of the presence or identity of the mutation of the biomarker or the amount of marker activity.

In one format, the RNA is immobilized on a solid surface and contacted with a probe, for example by running the isolated RNA on an agarose gel and transferring the RNA from the gel to a membrane, such as nitrocellulose. In an alternative format, the nucleic acid probe(s) are immobilized on a solid surface and the RNA is contacted with the probe(s), for example, in an AFFYMETRIX® gene chip array or a SNP chip (Santa Clara, Calif.) or customized array using a marker set comprising at least one marker indicative of treatment outcome. A skilled artisan can readily adapt known RNA and DNA detection methods for use in detecting the amount of the markers of the present invention. For example, the high density microarray or branched DNA assay can benefit from a higher concentration of tumor cell in the sample, such as a sample which had been modified to isolate tumor cells as described in earlier sections. In a related embodiment, a mixture of transcribed polynucleotides obtained from the sample is contacted with a substrate having fixed thereto a polynucleotide complementary to or homologous with at least a portion (e.g., at least 7, 10, 15, 20, 25, 30, 40, 50, 100, 500, or more nucleotide residues) of a marker nucleic acid. If polynucleotides complementary to or homologous with the marker are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). In an embodiment when a method of assessing marker expression is used which involves hybridization of one nucleic acid with another, the hybridization can be performed under stringent hybridization conditions.

An alternative method for determining the amount of RNA corresponding to a marker of the present invention in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to about 30 nucleotides in length and flank a region from about 50 to about 200 nucleotides in length. Under appropriate conditions and with appropriate reagents, such primers permit the amplification of a nucleic acid molecule comprising the nucleotide sequence flanked by the primers.

For in situ methods, RNA does not need to be isolated from the cells prior to detection. In such methods, a cell or tissue sample is prepared/processed using known histological methods. The sample is then immobilized on a support, typically a glass slide, and then contacted with a probe that can hybridize to RNA that encodes the marker.

In another embodiment of the present invention, a polypeptide corresponding to a marker, e.g., a polypeptide encoded by a nucleotide sequence associated with the marker genes identified in Tables 1, 2 or 3, is detected. In some embodiments, an agent for detecting a polypeptide of the invention is an antibody capable of binding to a polypeptide corresponding to a marker of the invention. In related embodiments, the antibody has a detectable label. Antibodies can be; polyclonal, or monoclonal. An intact antibody, or a fragment thereof (e.g., Fab or F(ab')$_2$) can be used.

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether B cells express a marker of the present invention.

Another method for determining the level of a polypeptide corresponding to a marker is mass spectrometry. For example, intact proteins or peptides, e.g., tryptic peptides can be analyzed from a sample, e.g., a blood sample, a lymph sample or other sample, containing one or more polypeptide markers. The method can further include treating the sample to lower the amounts of abundant proteins, e.g., serum albumin, to increase the sensitivity of the method. For example, liquid chromatography can be used to fractionate the sample so portions of the sample can be analyzed separately by mass spectrometry. The steps can be performed in separate systems or in a combined liquid chromatography/mass spectrometry system (LC/MS, see for example, Liao, et al. (2004) *Arthritis Rheum.* 50:3792-3803). The mass spectrometry system also can be in tandem (MS/MS) mode. The charge state distribution of the protein or peptide mixture can be acquired over one or multiple scans and analyzed by statistical methods, e.g. using the retention time and mass-to-charge ratio (m/z) in the LC/MS system, to identify proteins expressed at statistically significant levels differentially in samples from patients responsive or non-responsive to NAE inhibition therapy. Examples of mass spectrometers which can be used are an ion trap system (ThermoFinnigan, San Jose, Calif.) or a quadrupole time-of-flight mass spectrometer (Applied Biosystems, Foster City, Calif.). The method can further include the step of peptide mass fingerprinting, e.g. in a matrix-assisted laser desorption ionization with time-of-flight (MALDI-TOF) mass spectrometry method. The method can further include the step of sequencing one or more of the tryptic peptides. Results of this method can be used to identify proteins from primary sequence databases, e.g., maintained by the National Center for Biotechnology Information, Bethesda, Md., or the Swiss Institute for Bioinformatics, Geneva, Switzerland, and based on mass spectrometry tryptic peptide m/z base peaks.

Electronic Apparatus Readable Arrays

Electronic apparatus, including readable arrays comprising at least one predictive marker of the present invention is also contemplated for use in conjunction with the methods of the invention. As used herein, "electronic apparatus readable media" refers to any suitable medium for storing, holding or containing data or information that can be read and accessed directly by an electronic apparatus. As used herein, the term "electronic apparatus" is intended to include any suitable computing or processing apparatus or other device configured or adapted for storing data or information. Examples of electronic apparatus suitable for use with the present invention and monitoring of the recorded information include stand-alone computing apparatus; networks, including a local area network (LAN), a wide area network (WAN) Internet, Intranet, and Extranet; electronic appliances such as personal digital assistants (PDAs), cellular phone, pager and the like; and local and distributed processing systems. As used herein, "recorded" refers to a process for storing or encoding information on the electronic apparatus readable medium. Those skilled in the art can readily adopt any of the presently known methods for recording information on known media to generate manufactures comprising the markers of the present invention.

For example, microarray systems are well known and used in the art for assessment of samples, whether by assessment gene expression (e.g., DNA detection, RNA detection, protein detection), or metabolite production, for example. Microarrays for use according to the invention include one or more probes of predictive marker(s) of the invention characteristic of response and/or non-response to a therapeutic regimen as described herein. In one embodiment, the microarray comprises one or more probes corresponding to one or more of markers selected from the group consisting of markers which demonstrate increased expression in short term survivors, and genes which demonstrate increased expression in long term survivors in patients. A number of different microarray configurations and methods for their production are known to those of skill in the art and are disclosed, for example, in U.S. Pat. Nos. 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770,456; 5,770,722; 5,837,832; 5,856,101; 5,874,219; 5,885,837; 5,919,523; 5,981,185; 6,022,963; 6,077,674; 6,156,501; 6,261,776; 6,346,413; 6,440,677; 6,451,536; 6,576,424; 6,6104,82; 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; Shena, et al. (1998), *Tibtech* 16:301; Duggan et al. (1999) *Nat. Genet.* 21:10; Bowtell et al. (1999) *Nat. Genet.* 21:25; Lipshutz et al. (1999) *Nature Genet.* 21:20-24, 1999; Blanchard, et al. (1996) *Biosensors and Bioelectronics,* 11:687-90; Maskos, et al., (1993) *Nucleic Acids Res.* 21:4663-69; Hughes, et al. (2001) *Nat. Biotechol.* 19:342, 2001; each of which are herein incorporated by reference. A tissue microarray can be used for protein identification (see Hans et al. (2004) *Blood* 103:275-282). A phage-epitope microarray can be used to identify one or more proteins in a sample based on whether the protein or proteins induce auto-antibodies in the patient (Bradford et al. (2006) *Urol. Oncol.* 24:237-242).

A microarray thus comprises one or more probes corresponding to one or more markers identified herein, e.g., those indicative of treatment outcome, e.g., to identify, detect or quantify nucleic acid corresponding to marker genes. The microarray can comprise probes corresponding to, for example, at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 85, or at least 100, biomarkers and/or mutations thereof indicative of treatment outcome. The microarray can comprise probes corresponding to one or more biomarkers as set forth herein. Still further, the microarray may comprise complete marker sets as set forth herein and which may be selected and compiled according to the methods set forth herein. The microarray can be used to assay expression of one or more predictive markers or predictive marker sets in the array. In one example, the array can be used to assay more than one predictive marker or marker set expression in a sample to ascertain an expression profile of markers in the array. In this manner, the entire marker set can be simultaneously assayed for expression. This allows an expression profile to be developed showing a battery of markers specifically expressed in one or more samples. Still further, this allows an expression profile to be developed, e.g., correlated for a score to assess treatment outcome.

The array is also useful for ascertaining differential expression patterns of one or more markers in normal and abnormal (e.g., sample, e.g., tumor) cells. This provides a battery of markers that could serve as a tool for ease of identification of treatment outcome of patients. Further, the array is useful for ascertaining expression of reference markers for reference expression levels. In another example, the array can be used to monitor the time course of expression of one or more markers in the array.

In addition to such qualitative determination, the invention allows the quantification of marker expression. Thus, predictive markers can be grouped on the basis of marker sets or outcome indications by the amount of the marker in the sample. This is useful, for example, in ascertaining the outcome of the sample by virtue of scoring the amounts according to the methods provided herein.

The array is also useful for ascertaining the effect of the expression of a marker on the expression of other predictive markers in the same cell or in different cells. This provides, for example, a selection of alternate molecular targets for therapeutic intervention if patient is predicted to have an unfavorable outcome.

Reagents and Kits

The invention also encompasses kits for detecting the presence of a polypeptide or nucleic acid corresponding to a marker of the invention in a sample (e.g. a bone marrow sample, tumor biopsy or a reference sample). Such kits can be used to assess treatment outcome, e.g., determine if a subject can have a favorable outcome, e.g., after NAE inhibitor or EGFR inhibitor treatment. For example, the kit can comprise a labeled compound or agent capable of detecting a genomic DNA segment, a polypeptide or a transcribed RNA corresponding to a marker of the invention or a mutation of a marker gene in a sample and means for determining the amount of the genomic DNA segment, the polypeptide or RNA in the sample. Suitable reagents for binding with a marker protein include antibodies, antibody derivatives, antibody fragments, and the like. Suitable reagents for binding with a marker nucleic acid (e.g., a genomic DNA, an mRNA, a spliced mRNA, a cDNA, or the like) include complementary nucleic acids. The kit can also contain a control or reference sample or a series of control or reference samples which can be assayed and compared to the test sample. For example, the kit may have a positive control sample, e.g., including one or more markers or mutations described herein, or reference markers, e.g. housekeeping markers to standardize the assay among samples or timepoints or reference genomes, e.g., form subjects without tumor e.g., to establish diploid copy number baseline or reference expression level of a marker. By way of example, the kit may comprise fluids (e.g., buffer) suitable for annealing complementary nucleic acids or for binding an antibody with a protein with which it specifically binds and one or more sample compartments. The kit of the invention may optionally comprise additional components useful for performing the methods of the invention, e.g., a sample collection vessel, e.g., a tube, and optionally, means for optimizing the amount of marker detected, for example if there may be time or adverse storage and handling conditions between the time of sampling and the time of analysis. For example, the kit can contain means for increasing the number of tumor cells in the sample, as described above, a buffering agent, a preservative, a stabilizing agent or additional reagents for preparation of cellular material or probes for use in the methods provided; and detectable label, alone or conjugated to or incorporated within the provided probe(s). In one exemplary embodiment, a kit comprising a sample collection vessel can comprise e.g., a tube comprising anti-coagulant and/or stabilizer, as described above, or known to those skilled in the art. The kit can further comprise components necessary for detecting the detectable label (e.g., an enzyme or a substrate). For marker sets, the kit can comprise a marker set array or chip for use in detecting the biomarkers. Kits also can include instructions for interpreting the results obtained using the kit. For example, a kit can include information of cutoff values, e.g., to compare the score of a test sample with the samples used to develop the model or marker set. For example, a cutoff value for NAE inhibitor, e.g., MLN4924 treatment prediction is −1.45; a cutoff value for EGFR inhibitor, e.g., erlotinib treatment prediction is 0.5. The kit can contain reagents for detecting one or more biomarkers, e.g., 2, 3, 4, 5, or more biomarkers described herein.

In one embodiment, the kit comprises a probe to detect at least one biomarker, e.g., a marker indicative of treatment outcome (e.g., upon NAE inhibitor or EGFR inhibitor treatment). In an exemplary embodiment, the kit comprises a nucleic acid probe to detect a marker gene selected from the group consisting of genes identified in Table 1, Table 2 or Table 3, marker nucleic acid sequences listed in Table 1, Table 2 or Table 3, a marker nucleic acid identified from a model built by the methods described herein, and a complement of any of the foregoing. In another embodiment, the kit comprises reagents to bind, detect or measure the probeset target sequences identified in Table 1, Table 2 or Table 3. In some embodiments, the kit comprises a probe to detect a marker selected from the group consisting of MYC, MYB, CGA, and RSG10. In an embodiment, a kit comprises probes to detect a marker set comprising two or more markers from the group consisting of MYC, MYB, CGA, and RSG10. For kits comprising nucleic acid probes, e.g., oligonucleotide-based kits, the kit can comprise, for example: one or more nucleic acid reagents such as an oligonucleotide (labeled or non-labeled) which hybridizes to a nucleic acid sequence corresponding to a marker of the invention, optionally fixed to a substrate; labeled oligonucleotides not bound with a substrate, a pair of PCR primers, useful for amplifying a nucleic acid molecule corresponding to a marker of the invention, molecular beacon probes, a marker set comprising oligonucleotides which hybridize to at least two nucleic acid sequences corresponding to markers of the invention, and the like. The kit can contain an RNA-stabilizing agent.

For kits comprising protein probes, e.g., antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label. The kit can contain a protein stabilizing agent. The kit can contain reagents to reduce the amount of non-specific binding of non-biomarker material from the sample to the probe. Examples of reagents include nonioinic detergents, non-specific protein containing solutions, such as those containing albumin or casein, or other substances known to those skilled in the art.

An isolated polypeptide corresponding to a predictive marker of the invention, or a fragment or mutant thereof, can be used as an immunogen to generate antibodies using standard techniques for polyclonal and monoclonal antibody preparation. For example, an immunogen typically is used to prepare antibodies by immunizing a suitable (i.e., immunocompetent) subject such as a rabbit, goat, mouse, or other mammal or vertebrate. In still a further aspect, the invention provides monoclonal antibodies or antigen binding fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 8, 10, 12, 15, 20 or 25 amino acid residues of an amino acid sequence of the present invention, an amino acid sequence which is at least 95%, 96%, 97%, 98% or 99% identical to an amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. The monoclonal antibodies can be human, humanized, chimeric and/or non-human antibodies. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Methods for making human antibodies are known in the art. One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals can be made using XENOMOUSE™ technology or by using a "minilocus" approach. Methods for making XENOMICE™ are described in U.S. Pat. Nos. 6,162,963, 6,150,584, 6,114,598 and 6,075,181, which are incorporated herein by reference. Methods for making transgenic animals using the "minilocus" approach are described in U.S. Pat. Nos. 5,545,807, 5,545,806 and 5,625,825; also see International Publication No. WO93/12227, which are each incorporated herein by reference.

Antibodies include immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a sample, which naturally contains the polypeptide. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341:544-546 (1989)), which consists of a VH domain; (vii) a single domain functional heavy chain antibody, which consists of a VHH domain (known as a nanobody) see e.g., Cortez-Retamozo, et al., Cancer Res. 64: 2853-2857 (2004), and references cited therein; and (vii) an isolated complementarity determining region (CDR), e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. Science 242:423-426 (1988); and Huston et al. Proc. Natl. Acad. Sci. USA 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antibody fragments, such as Fv, F(ab)$_2$ and Fab may be prepared by cleavage of the intact protein, e.g. by protease or chemical cleavage. The invention provides polyclonal and monoclonal antibodies. Synthetic and genetically engineered variants (See U.S. Pat. No. 6,331,415) of any of the foregoing are also contemplated by the present invention. Polyclonal and monoclonal antibodies can be produced by a variety of techniques, including conventional murine monoclonal antibody methodology e.g., the standard somatic cell hybridization technique of Kohler and Milstein, Nature 256: 495 (1975) the human B cell hybridoma technique (see Kozbor et al., 1983, Immunol. Today 4:72), the EBV-hybridoma technique (see Cole et al., pp. 77-96 In Monoclonal Antibodies and Cancer Therapy, Alan R. Liss, Inc., 1985) or trioma techniques. See generally, Harlow, E. and Lane, D. (1988) Antibodies: A Laboratory Manual, Cold Spring Harbor Laboratory Press, Cold Spring Harbor, N.Y.; and Current Protocols in Immunology, Coligan et al. ed., John Wiley & Sons, New York, 1994. For diagnostic applications, the antibodies can be monoclonal antibodies, e.g., generated in mouse, rat, or rabbit. Additionally, for use in in vivo applications the antibodies of the present invention can be human or humanized antibodies. Hybridoma cells producing a monoclonal antibody of the invention are detected by screening the hybridoma culture supernatants for antibodies that bind the polypeptide of interest, e.g., using a standard ELISA assay.

If desired, the antibody molecules can be harvested or isolated from the subject (e.g., from the blood or serum of the subject) and further purified by well-known techniques, such as protein A chromatography to obtain the IgG fraction. Alternatively, antibodies specific for a protein or polypeptide of the invention can be selected or (e.g., partially purified) or purified by, e.g., affinity chromatography to obtain substantially purified and purified antibody. By a substantially purified antibody composition is meant, in this context, that the antibody sample contains at most only 30% (by dry weight) of contaminating antibodies directed against epitopes other than those of the desired protein or polypeptide of the invention, and at most 20%, at most 10%, or at most 5% (by dry weight) of the sample is contaminating antibodies. A purified antibody composition means that at least 99% of the antibodies in the composition are directed against the desired protein or polypeptide of the invention.

An antibody directed against a polypeptide corresponding to a marker of the invention (e.g., a monoclonal antibody) can be used to detect the marker (e.g., in a cellular sample) in order to evaluate the level and pattern of expression of the marker. The antibodies can also be used diagnostically to monitor protein levels in tissues or body fluids (e.g. in a blood sample) as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Accordingly, in one aspect, the invention provides substantially purified antibodies or fragments thereof, and non-human antibodies or fragments thereof, which antibodies or fragments specifically bind to a polypeptide comprising an amino acid sequence encoded by a marker identified herein. The substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence which is encoded by a nucleic acid molecule of a predictive marker of the invention. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

The substantially purified antibodies or fragments thereof may specifically bind to a signal peptide, a secreted sequence, an extracellular domain, a transmembrane or a cytoplasmic domain or cytoplasmic loop of a polypeptide of the invention. The substantially purified antibodies or fragments thereof, the non-human antibodies or fragments thereof, and/or the monoclonal antibodies or fragments thereof, of the invention specifically bind to a secreted sequence or an extracellular domain of the amino acid sequences of the present invention.

The invention also provides a kit containing an antibody of the invention conjugated to a detectable substance, and instructions for use. Still another aspect of the invention is a diagnostic composition comprising a probe of the invention and a pharmaceutically acceptable carrier. In one embodiment, the diagnostic composition contains an antibody of the invention, a detectable moiety, and a pharmaceutically acceptable carrier.

Use of Information

In one method, information, e.g., about the patient's marker(s) characteristic, e.g., size, sequence, composition or amount (e.g., the result of evaluating a marker or marker set described herein), or about whether a patient is expected to have a favorable outcome, is provided (e.g., communicated, e.g., electronically communicated) to a third party, e.g., a hospital, clinic, a government entity, reimbursing party or insurance company (e.g., a life insurance company). For example, choice of medical procedure, payment for a medical procedure, payment by a reimbursing party, or cost for a service or insurance can be function of the information. E.g., the third party receives the information, makes a determination based at least in part on the information, and optionally communicates the information or makes a choice of procedure, payment, level of payment, coverage, etc. based on the information. In the method, informative expression level of a marker or a marker set selected from or derived from Table 1, Table 2 or Table 3 and/or derived from a method as described herein is determined.

In one embodiment, a premium for insurance (e.g., life or medical) is evaluated as a function of information about one or more marker expression levels, e.g., a marker or marker set, e.g., a level of expression associated with treatment outcome (e.g., the informative amount). For example, premiums can be increased (e.g., by a certain percentage) if the marker genes of a patient or a patient's marker set described herein have different characteristic, e.g., size, sequence, composition or amount between an insured candidate (or a candidate seeking insurance coverage) and cutoff value, a training set, a reference value (e.g., a non-afflicted person) or a reference sample, e.g., matched control. Premiums can also be scaled depending on the result of evaluating a marker or marker set described herein. For example, premiums can be assessed to distribute risk, e.g., as a function of marker, e.g., the result of evaluating a marker or marker set described herein. In another example, premiums are assessed as a function of actuarial data that is obtained from samples or patients that have known treatment outcomes.

Information about marker characteristic, e.g., size, sequence, composition or amount, e.g., the result of evaluating a marker or marker set described herein (e.g., the score), can be used, e.g., in an underwriting process for life insurance. The information can be incorporated into a profile about a subject. Other information in the profile can include, for example, date of birth, gender, marital status, banking information, credit information, children, and so forth. An insurance policy can be recommended as a function of the information on marker characteristic, e.g., size, sequence, composition or amount, e.g., the result of evaluating a marker or marker set described herein, along with one or more other items of information in the profile. An insurance premium or risk assessment can also be evaluated as function of the marker or marker set information. In one implementation, points are assigned on the basis of expected treatment outcome.

In one embodiment, information about marker characteristic, e.g., size, sequence, composition or amount, e.g., the result of evaluating a marker or marker set described herein, is analyzed by a function that determines whether to authorize the transfer of funds to pay for a service or treatment provided to a subject (or make another decision referred to herein). For example, the results of analyzing a characteristic, e.g., size, sequence, composition or amount of a marker or marker set described herein may indicate that a subject is expected to have a favorable outcome, suggesting that a treatment course is needed, thereby triggering an result that indicates or causes authorization to pay for a service or treatment provided to a subject. In one example, informative characteristic, e.g., size, sequence, composition or amount of a marker or a marker set selected from or derived from Table 1 and/or described herein is determined and payment is authorized if the informative amount identifies a favorable outcome. For example, an entity, e.g., a hospital, care giver, government entity, or an insurance company or other entity which pays for, or reimburses medical expenses, can use the result of a method described herein to determine whether a party, e.g., a party other than the subject patient, will pay for services (e.g., a particular therapy) or treatment provided to the patient. For example, a first entity, e.g., an insurance company, can use the outcome of a method described herein to determine whether to provide financial payment to, or on behalf of, a patient, e.g., whether to reimburse a third party, e.g., a vendor of goods or services, a hospital, physician, or other care-giver, for a service or treatment provided to a patient. For example, a first entity, e.g., an insurance company, can use the outcome of a method described herein to determine whether to continue, discontinue, enroll an individual in an insurance plan or program, e.g., a health insurance or life insurance plan or program.

In one aspect, the disclosure features a method of providing data. The method includes providing data described herein, e.g., generated by a method described herein, to provide a record, e.g., a record described herein, for determining if a payment will be provided. In some embodiments, the data is provided by computer, compact disc, telephone, facsimile, email, or letter. In some embodiments, the data is provided by a first party to a second party. In some embodiments, the first party is selected from the subject, a healthcare provider, a treating physician, a health maintenance organization (HMO), a hospital, a governmental entity, or an entity which sells or supplies the drug. In some embodiments, the second party is a third party payor, an insurance company, employer, employer sponsored health plan, HMO, or governmental entity. In some embodiments, the first party is selected from the subject, a healthcare provider, a treating physician, an HMO, a hospital, an insurance company, or an entity which sells or supplies the drug and the second party is a governmental entity. In some embodiments, the first party is selected from the subject, a healthcare provider, a treating physician, an HMO, a hospital, an insurance company, or an entity which sells or supplies the drug and the second party is an insurance company.

In another aspect, the disclosure features a record (e.g., computer readable record) which includes a list and value of characteristic, e.g., size, sequence, composition or amount for the marker or marker set for a patient. In some embodiments, the record includes more than one value for each marker.

The present invention will now be illustrated by the following Examples, which are not intended to be limiting in any way.

EXAMPLES

Example 1

Cell Line Panel Expression Analysis

A panel of cell lines was used to support clinical development and identify potential biomarkers of tumor sensitivity or resistance. A large cancer cell line panel N=240 (Ricerca Biosciences, Inc., Bothell, Wash.; O'Day et al. (2010) Fourth AACR International Conference on Molecular Diagnostics in Cancer Therapeutic Development)) was used for these studies. The expression of genes in each cell line of the panel was measured on the Human Genome U133 Plus 2.0 Array (Affymetrix, Santa Clara Calif.). To generate the gene expression data, RNA isolation, hybridization, and wash conditions were the same as indicated in the Affymetrix gene expression manuals. Arrays were washed and stained according to standard Affymetrix protocols using an Affymetrix Fluidics Workstation, and scanned using an Affymetrix GeneArray scanner. The gene expression intensities (.CEL files) were captured by the Affymetrix GeneChip Operating Software (GCOS). This gene expression data set was used for training both the MLN4924 treatment model and the erlotinib treatment model.

Example 2

Treatment of the Cell Line Panel with MLN4924

The cell lines in the panel of Example 1 were treated with MLN4924 and cell viability data (IC50, EC50, and POC—Percentage of Control) were generated. MLN4924 was added in half-log dilutions for 10 concentrations and treated for 72 hours. High-content cell screening by fluorescence microscopy included image analysis to generate several types of data. Results included EC50 values (after measurement of cell numbers, the EC50 concentration was calculated from the inflection point of a curve of percent of control (POC) against log of MLN4924 concentration), IC50 values (from the POC-log MLN4924 plot, IC50 is the concentration at 50% maximal possible response), apoptosis (measurement of activation of caspase 3 plotted against log of MLN4924 concentration, determined as the concentration for >5 fold induction), and mitotic activity (determined by measuring the fold increase of phospho-histone 3). A comparison of EC50 to IC50 (FIG. 2) allowed assignment of cell lines to sensitive, insensitive or resistant. Final identification of a cell line as sensitive or resistant was based on the EC50 values. The cutoff for sensitivity is a median EC50 of less than the median value of all POC's recorded in the panel (<0.36), borderline sensitivity was associated with median EC50 of 0.36 to 1.67 and insensitive or resistant cell lines were identified by EC50 greater than the $3^{rd}$ quartile of all POC's in the panel (>1.67).

Example 3

Building a Predictive Model for MLN4924

Data reduction. First, the cell line gene expression data underwent robust multi-array average (RMA) normalization to establish the baseline of the gene expression data. Next, an intensity cutoff of 40% of the whole genome was applied to the data to remove genes that may not present in the system. Then, a variance cutoff of 1 was applied to keep only genes whose intensities varied the most in the cancer cell line panel.

Feature selection. The correlation between each of the remaining, filtered, probeset's expression and drug responses as $log_2(IC50)$ was evaluated. Permutation was performed on each probeset by randomly assigning drug response to panel cell lines, and a raw p-value was calculated based on the permutation testing. Feature probesets were selected using a raw p-value cutoff of 0.01. Then, representative probesets were selected for each gene (the highest intensity probeset for each gene, which is normally the highest variance probeset for that gene as well). 369 genes were selected for PLSR model training and testing.

Splitting the Data and Identifying top non-overlapping models. For modeling training/testing, the cell lines were divided into sub-training (42%), sub-testing (28%), and sep-testing (30%). After thousands (200,000) of rounds on splits in this way, the top models were selected by checking multiple features on both sub-testing and sep-testing results: 1. Top models should have top performance on sub-testing on both AUC and correlation measures; 2. Among all splits, correlated cases were preferred on sub-testing between AUC and correlation; 3. Sep-testing (from the balanced split) should have much narrower performance distribution vs sub-testing on both AUC and correlation measures; 4. Top model performance in sep-testing should be at least similar to that in sub-testing; 5. Top models collectively should have relatively high performance among all splits. Overall, this specially designed split strategy helped to identify consensus information among top performing models.

After identifying the top 5 models using the above criteria, the overlapping on cell lines was checked between each pair of top models. This is because that the modeling framework is designed to capture common features across the whole panel, by finding non-overlapping top models that are consistent to each other on signature genes' contribution. To check the overlap, first there was a permutation on splits, to generate an overlapping score distribution. A 90% quantile on pairwise overlapping of models was selected as a non-overlapping cutoff. As can be seen in the Table 5 below, models 28 and 55 significantly overlapped with other top models.

TABLE 5

Comparison of top models of MLN4924 treatment for evaluation of overlap

| Model | 18 | 28 | 49 | 55 | 89 |
|---|---|---|---|---|---|
| 18 | 1 | 0.308271 | 0.270073 | 0.359375 | 0.270073 |
| 28 | 0.308271 | 1 | 0.270073 | 0.26087 | 0.270073 |
| 49 | 0.270073 | 0.270073 | 1 | 0.318182 | 0.279412 |
| 55 | 0.359375 | 0.26087 | 0.318182 | 1 | 0.225352 |
| 89 | 0.270073 | 0.270073 | 0.279412 | 0.225352 | 1 |

Finding consensus gene weights and selecting a core signature gene set. After identifying top models from the specially designed split strategy above, the following steps were used to find a core set of genes: 1. Removal of top models 28 and 55 that were overlapping to each other (sharing significantly common cell lines in sub-training sets); 2. Consensus weighting was performed on the remaining top models using Singular value decomposition (SVD); 3. Starting from highest weighted genes and adding one gene at a time, a forward search was undertaken to find the core signature set.

Figure 3A:
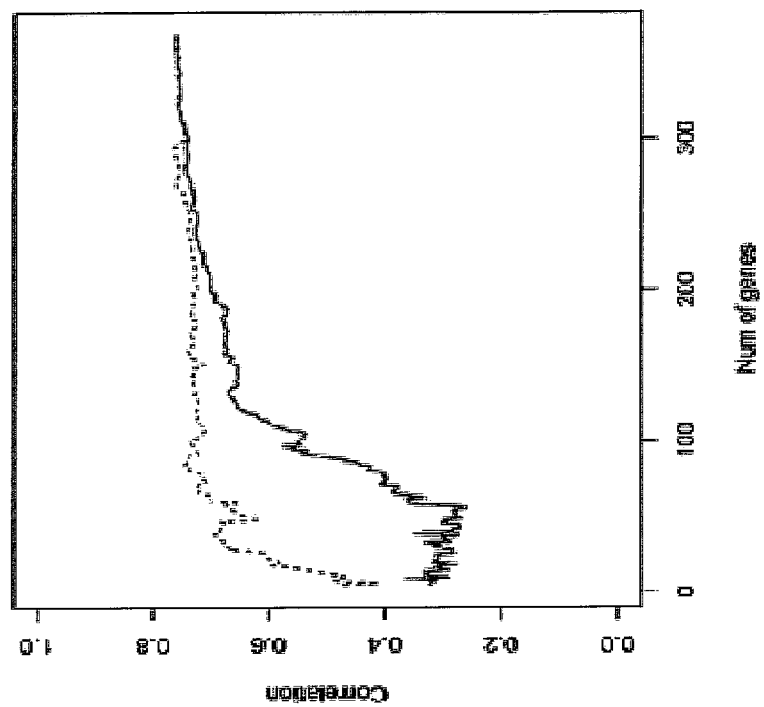
Figure 3B:
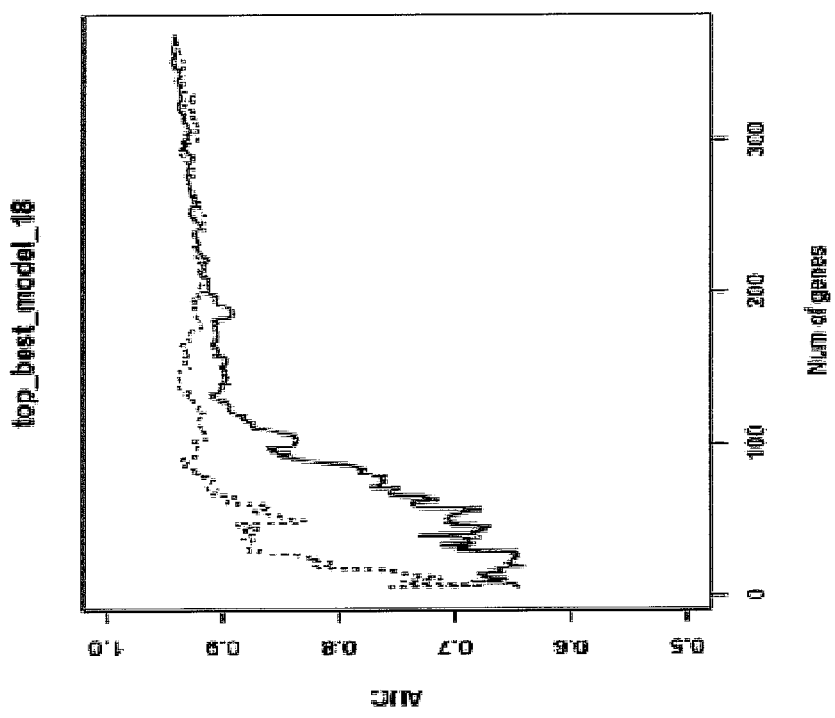

A review compared individual gene weighting between the consensus weighting and each individual top model, together with all pairwise comparisons between individual top models. Although these top models represented a non-overlapping separation of training subsets, the genes' contributions to the model were still highly correlated among top models. The consensus weightings identified from SVD approach showed higher correlation to each individual top model. The individual top model (model 18) that showed the highest similarity to the consensus weightings was selected as the representative model for later steps. The core PLSR model was identified at the point, at 250 genes, when both AUC and correlation performance of the model reached a similar level to the full model (FIGS. 3A and 3B). The dotted line on FIGS. 3A and B is showing one randomly selected control case on randomly selecting genes from the full PLSR model (the solid line selects genes by weighting). As can be seen in these figures, this particular random control (dotted line) seems to reach saturation quicker, while it still fluctuates more than the solid line.

Trimming the model based on pathway associations. The pathway-based PLSR model was built with the following steps: 1. The core PLSR model gene set (250 genes) was provided as input for GeneGo's pathway enrichment analysis; 2. Over-represented pathways were found for the input gene list (using a p-value cutoff of 0.05); 3. The core genes that also appeared on the over-represented pathways were selected as a subset (69 genes) of the core PLSR model (69 genes) and the remaining genes were discarded; 4. Re-train/Re-test the top PLSR model using the 69 gene "pathway based classifier" to verify by AUC and correlation that the subset performed similar to the core PLSR model. Over-represented pathways in the MLN4924 core model included the TGFbeta-SMAD signaling and adhesion receptor-induced signaling pathways for resistance and c-myc and c-myb transcription factor pathways for sensitivity. The genes identified in a pathway-based classifier for MLN4924 are listed in Table 1. Of the genes listed in Table 1, BAG2, MYC, MYB, CSDA and C1R were highly expressed in cell lines which were sensitive to MLN4924 and the remaining genes were highly expressed in cell lines which were resistant to MLN4924. Notably, two pump genes, ABCC3 and ABCG2, are within the signature gene set, consistent with previous knowledge that high pump gene expression links to MLN4924 resistance. Moreover, both MYB and MYC are present in the signature list, suggesting a MYC-related mechanism of MLN4924 treatment effect.

An alternative "pathway-based classifier" was generated by applying a more stringent cutoff on identifying over-represented signaling pathways (a p-value of 0.01 instead of 0.05). This results in a more highly correlated set of marker numbers 1 through 3 and 5 through 45 in Table 1.

A review of the behaviors of the genes in the pathway-based classifier, subset of the core PLSR model determined that four genes played a strong role in model prediction performance, MYB, MYC, CGA and RGS10. These genes all had negative PLSR loading values. Therefore higher expression values of these genes, by themselves or as a group, in a sample may indicate better MLN4924 sensitivity.

Example 4

Treating the Cell Line Panel with Erlotinib

For the Erlotinib model, the same cell line panel described in Example 1 was treated with erlotinib to identify sensitive and resistant cell lines. Growth and assay conditions were established for all 240 cell lines. Compounds were added in half-log dilutions for 10 concentrations using tipless acoustic transfer with an Echo 550. An additional "time zero" (T0) plate also was seeded at the same density and analyzed for cell number on day one to determine the number of doublings. Seventy-two hours after compound addition, the cells were fixed and stained with antibodies for activated caspase-3 and phosphohistone H3. The "drc" R-package was adopted to fit a four-parameter logistic curve and calculated IC50 values for the panel cell lines. After removing cell lines that have high variance (on replicate data) and/or missing proliferation data, 183 cell lines that have good quality of data were used for further studies.

Example 5

Building a Predictive Model for Erlotinib

The same expression data for the cell lines generated in Example 1 was used to build a model of erlotinib treatment using the following steps:

Data reduction. First, the cell line gene expression data underwent robust multi-array average (RMA) normalization to establish the baseline of the gene expression data. Next, an intensity cutoff of 40% of the whole genome was applied to the data to remove genes of low intensities or that may not be present in the system. Then, a variance cutoff of 1 was applied to keep only genes whose intensities varied the most in the cancer cell line panel. This data reduction step reduced the number of probesets from 54,675 to 3,787.

Feature selection. The correlation between each of the remaining (3787), filtered, probeset's expression and drug responses as $\log_2(IC50)$ was evaluated. Permutation was performed on each probeset by randomly assigning drug response to panel cell lines, and a raw p-value was calculated based on the permutation testing. Feature probesets were selected using a raw p-value cutoff of 0.01. Then, representative probesets were selected for each gene (the highest intensity probeset for each gene, which is normally the highest variance probeset for that gene as well). 485 genes were selected for PLSR model training and testing.

Splitting the data To find the top-performing models that also captured consensus features in the dataset, the data from the whole training set from the cell lines were divided by a special splitting approach: First, they were divided by a "balanced split" to divide the data into training (70%) and sep-testing (balance validation) (30%) subsets. Then, the training subset was further divided into sub-training (random training) (60% of training) and sub-testing (random validation) (40% of the training) subsets. Overall, the whole training set is divided into three parts: sub-training (random training) (42%), sub-testing (random testing) (28%), and sep-testing (balance validation) (30%). Thousands (200, 000) of rounds on splits in this way (200 balanced splits and 1000 sub-splits of each balanced training subset), to provide models for further evaluation.

Identifying top non-overlapping models. The top models were selected by checking multiple features on both sub-testing and sep-testing results: 1. Top models should have good performance on sub-testing on both AUC and correlation measures; 2. Among all splits, correlated cases between AUC and correlation were preferred on sub-testing subsets; 3. Sep-testing (from the balanced split) should have much narrower performance distribution compared to sub-testing on both AUC and correlation measures; 4. Top model performance in sep-testing should be at least similar to that in sub-testing; 5. Top models collectively should have relatively high performance among all splits in sep-testing. Overall, this specially designed split strategy helped to identify consensus information among top performing models.

The overlapping on cell lines was checked between each pair of top models. To check the overlap, first there was a permutation on splits, to generate an overlapping score distribution. A 90% quantile of 0.304 on pairwise overlapping of models was selected for a non-overlapping cutoff. As can be seen in the Table 6 below, model 3 significantly overlapped with other top models 4 and 5.

TABLE 6

Comparison of top models of erlotinib treatment for evaluation of overlap

| Model | 1 | 2 | 3 | 4 | 5 |
|---|---|---|---|---|---|
| 1 | 1 | | | | |
| 2 | 0.282 | 1 | | | |
| 3 | 0.261 | 0.240 | 1 | | |
| 4 | 0.230 | 0.220 | 0.316 | 1 | |
| 5 | 0.250 | 0.250 | 0.351 | 0.282 | 1 |

It was reasoned that if one can find a way to identify the consensus information within a training dataset, the resulting drug sensitivity signature (predictive model) should be robust and have high predictive power. This splitting strategy (division on random training, random validation and balance validation sample subsets), which creates balance validation subsets as well as random validation subsets. The feature selection was done on the whole dataset, so that the same feature genes could be used to train and compare models among different splits. This also enabled finding the best model that representing consensus information among the whole dataset. By identifying minimally overlapping high scored models and calculating consensus weighting among them, the common features were captured in the training dataset.

Finding consensus gene weights and selecting a core signature gene set. After identifying top models from the specially designed split strategy above, the following steps were used to find a core set of genes: 1. Removal of top model 3 that was over-lapping to other models; 2. Consensus weighting was performed on the remaining top models using Singular value decomposition (SVD); 3. Starting from highest weighted genes and adding one gene at a time, a forward search was undertaken to find the core signature set.

Figures 4A, 4B:
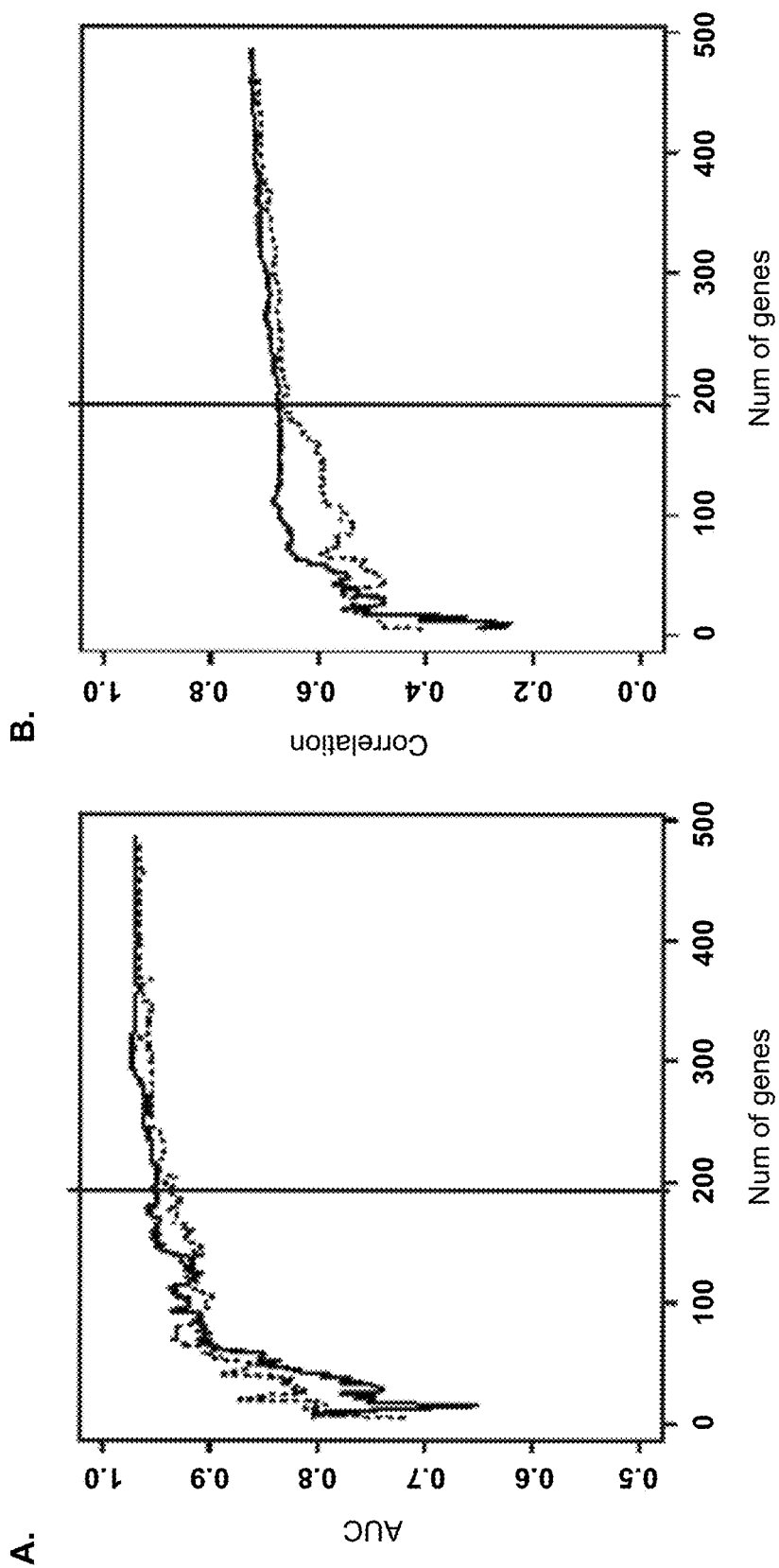

A review compared individual gene weighting between the consensus weighting and each individual top model, together with all pairwise comparisons between individual top models. Interestingly, these not-significantly-overlapped top models have correlated gene weights, therefore representing common features among the training dataset. The individual top model (model 5) that showed the highest similarity to the consensus weightings was selected as the representative model for later steps. Starting from the five highest weighted genes and adding one gene at a time, the representative PLSR model was retrained/retested by increasing signature gene size one at a time (a forward selection approach). The core PLSR model of was identified as an early plateau point on the model performance curves for both AUC and correlation measures. The plateau point of number of genes from model 5 to include in the core model was 191 genes, when both AUC and correlation performance of the model reached a similar level to the full model (FIGS. 4A and 4B). The dotted line on FIGS. 4 A and B is showing one randomly selected control case on randomly selecting genes from the full PLSR model (the solid line selects genes by weighting). As can be seen in these figures, forward searching from the highest weighted genes (solid line) works very well—quickly reaches saturation and fluctuates less than the random case (dotted line).

Trimming the model based on pathway associations. The pathway-based PLSR model was built with the following steps: 1. The core PLSR model gene set (191 genes) was provided as input for GeneGo's pathway enrichment analysis; 2. Over-represented pathways were found for the input gene list (using a p-value cutoff of 0.01); 3. The core genes that also appeared on the over-represented pathways were selected as a subset (51 genes) of the core PLSR model (51 genes) and the remaining genes were discarded; 4. Re-train/Re-test the top PLSR model using the 51 gene "pathway based classifier" to verify by AUC and correlation that the subset performed similar to the core PLSR model. These genes are listed in Table 2.

In the 51-gene signature, 22 genes correlated positively and 29 genes negatively with IC50 data. Interestingly, the EGFR ligand (NRG1) is among the signature genes, which is consistent with the fact that erlotinib is an anti-EGFR compound. Of the genes listed in Table 2, F2R, TUBA1A, MIR21, LEF1, COL1A2, SPATA13, VIM, L1CAM, IGFBP4, SDC2, VCAN, NRP1, GNG11, BMP4, ETV1, UBB, CCL2, NES, LGALS1, EPS8 and BAMBI were highly expressed in cell lines which were resistant to erlotinib and the remaining genes were highly expressed in cell lines which were sensitive to erlotinib.

Functional biomarkers are believed to be more robust on the larger datasets, although their predictive performance was not significantly different than gene signatures in several small scale studies. In one study, the authors developed a pathway-based modeling approach that can increase performance of pathway models Chuang et al. (2007) Mol. Syst. Biol. 3:140; Lee et al. (2008) PLos Comput. Biol. 4:e1000217). On each pre-selected canonical pathway, the authors identified a subset of genes whose expression profile collectively contributed more than the whole pathway. Then, the selected high contribution genes from multiple pathways were merged and used them as the input for model building and testing (Lu et al. (2005) Nature 435:834-838; Lee et al. supra. In the current work, this approach was adopted but with two key differences. First, the current approach started from the whole genome information to train the predictive model and to find a core signature gene set. This way, a pre-selected limited scaffold of biology captured on the pathway maps did not limit us. Second, canonical pathways enrichment was applied to filter core signature genes through the top scored pathways. The resulting 51-gene "functional" signature for Erlotinib was three times smaller than the original PSLR signature while had higher predictive accuracy on Erlotinib-treated patients.

Example 6

Testing the Erlotinib Pathway-based Model for Predicting Progression Free Survival PLSR models built on cancer cell line panel screen data against erlotinib response, was used to test patients' response to erlotinib. Notably, the model was trained on a panel of mixture cancer indications using IC50 values, while it was used to predict NSCLC patients' progression-free survival in the BATTLE trial (downloaded as BATTLE trial patients' baseline gene expression (Kim et al. (2011) *Cancer Discov.* 1:44-53) (GSE31437) from GEO database). A RMA normalization was done one each dataset separately, using Affy package from Bioconductor (Bolstat et al (2003) *Bioinformatics* 19:185-193).

The patient baseline gene expression data were generated using Affymetrix platform (HG Gene 1.0 ST), which is different microarray platform used on cell line panel in Example 1. To address this issue, first all probesets which overlapped between U133plus2 (Example 1 cell line data) and HG Gene 1.0 ST (BATTLE patient data) were identified. Then a RMA normalization on BATTLE data was performed against Example 1 cell line gene expression. Among the 191 genes in the core PLSR model trained from Example 1 data, 187 of them were also on the BATTLE dataset. Therefore the core PLSR model was re-trained using these 187 genes on Example 1 data to identify the pathway-based classifier which could be applied to predict patients' response to erlotinib on the BATTLE trial.

Core PLSR model performance FIGS. 5A and 5B show the core PLSR model performance against patients' survival on the BATTLE trial. FIG. 5A was the distribution of PLSR model predicted erlotinib responses—the vertical line represented a data-driven cutoff of 0.5 at the biggest separation point. FIG. 5B gives the PLSR model predicted scores vs clinic output (PFS) for each patient. The core PLSR model performance was evaluating using data driven cutoffs on both clinical and PLSR predicted numbers. Given the fact that prediction of patients' progression-free survival was performed from a model trained on in vitro cell line screen data on IC50s, the observed 76% overall accuracy is considered as a solid model performance.

Pathway-based PLSR model performance Similar to the testing of core PLSR model on BATTLE trial, the pathway-based PLSR predictive model was tested. It happens to be the case that the 51 genes in the cell-line pathway-based PLSR model also appear on the BATTLE gene expression dataset, so the 51-gene cell line panel pathway-based PLSR model was able to be directly tested on the BATTLE dataset. By adding orthogonal canonical pathway information, the size of signature gene set was reduced from 187 genes to 51 genes (from the core PLSR model to the pathway-based PLSR model), yet increased the overall accuracy of the model performance from 76% to 84%, using a cutoff value of 0.5 (FIGS. 6A and B).

Example 7

Building a Sorafenib Sensitivity Model

The same modeling framework was applied to build a Sorafenib predictive model, also on cell line screen data. Sorafenib is a pan-kinase inhibitor, a tyrosine kinase inhibitor that works on the vascular endothelial growth factor receptor (VEGFR) and other receptor tyrosine kinases (RAF/Multi-RTK), not EGFR. Different from Erlotinib's IC50 distribution (FIG. 5A), the Sorafenib IC50 values follow normal distribution (not shown). To better separate Sorafenib sensitive vs resistant cases, the middle one-third of panel cell lines was removed before the model training process. Even with this filtering, it was still harder to identify a good predictive model in Sorafenib case (vs. Erlotinib case).

Erlotinib and Sorafenib predictive model building were started with the same 183 cancer cell lines and their baseline gene expression data. Therefore, the data reduction is the same for both Erlotinib and Sorafenib. In the Sorafenib case, 903 feature genes were identified, with 550 core model genes, and eventually 113 genes for the final pathway signature (Table 3).

Similar to Erlotinib, a network of Sorafenib signature genes were generated using protein-protein interactions and canonical pathway information. The networks contained genes, which variants are significantly associated with the corresponding drug response. Specifically, PTEN deletions and HCF receptor amplification are associated with sensitivity to Sorafenib.

The genes positively correlated with IC50s and, as so, associated with resistance, tend to populate signaling pathways parallel or cross-talking to the drug target signaling (examples are PI3K signaling and calcium signaling). Activation of parallel pathways by overexpression or mutations conveys the common resistance mechanism for Sorafenib. One of Sorafenib-resistance pathways, EGFR signaling, is represented by 4 overexpressed ligands. Moreover, different genetic events in EGFR are associated with Sorafenib resistance among cell lines. Importantly, EGFR mutations were associated with worse response to Sorafenib in the BATTLE study.

A core set of signature genes for the sorafenib model includes genes along growth factor pathways: PDGFRA, FGFR1, HGF, IGF1R, MET, TGFB2, TGFA, IGFBP3, EGFR, IGFBP1.

Example 8

Testing the Erlotinib and Sorafenib Pathway-based Models Using the BATTLE Clinical Trial as an Independent Testing Dataset The BATTLE clinical trial data was used as an independent testing dataset, to evaluate the performance of the OncoPanel cell line data derived drug sensitivity models. In this Phase II trial (Kim et al. supra), subsets of 255 NSCLC patients were treated with either Erlotinib, Vandetanib, Sorafenib or Erlotinib+bexaroten combination. Among the 255 patients, there were 131 patients with tumor samples sufficient for molecular profiling and clinically evaluable (GSE33072). Among them, 25 patients were in the Erlotinib arm and 39 patients in the Sorafenib arm usable for model testing.

The baseline gene expression data in patients were generated using Affymetrix HG Gene 1.0 ST array, which is a different platform than the U133plus2 array used in the cell line panel. To address the issue of platform incompatibility, overlapping probe sets between U133plus2 and HG Gene 1.0 ST arrays were identified, then a quantile normalization on BATTLE data against cell line panel gene expression was performed. All 51 genes from Erlotinib functional pathway-based model were present in the BATTLE dataset, as well as all 113 Sorafenib signature genes.

The cutoffs of Erlotinib or Sorafenib predicted scores were data-driven by re-predicting IC50s on the cell line panel, using the corresponding drug sensitivity models. Since the BATTLE patients' baseline gene expression was normalized against cell line panel gene expression on the whole genome basis, the cutoffs defined from cell line panel dataset were applied to the BATTLE dataset.

For patients' PFS cutoffs, since Erlotinib or Sorafinib arm has small patient numbers (25 and 39 patients for Erlotinib and Sorafenib arms, respectively), arbitrarily cutoffs of Erlotinib and Sorafenib PFS were selected at 2.4 and 4 months, respectively. Shown as horizontal lines in FIGS. 7A-D, these cutoffs showed reasonable PFS separation on patients treated by Erlotinib or Sorafenib, respectively.

The erlotinib-generated and sorafenib-generated pathway-based classifiers were tested on their own clinical response data and on each other'sa data. Sorafenib is a tyrosine kinase inhibitor that works on the vascular endothelial growth factor receptor (VEGFR) and other receptor tyrosine kinases (RAF/Multi-RTK), not EGFR, i.e., it shares some mechanistic similarities with erlotinib, but does not have the same target.

Figure 7A:
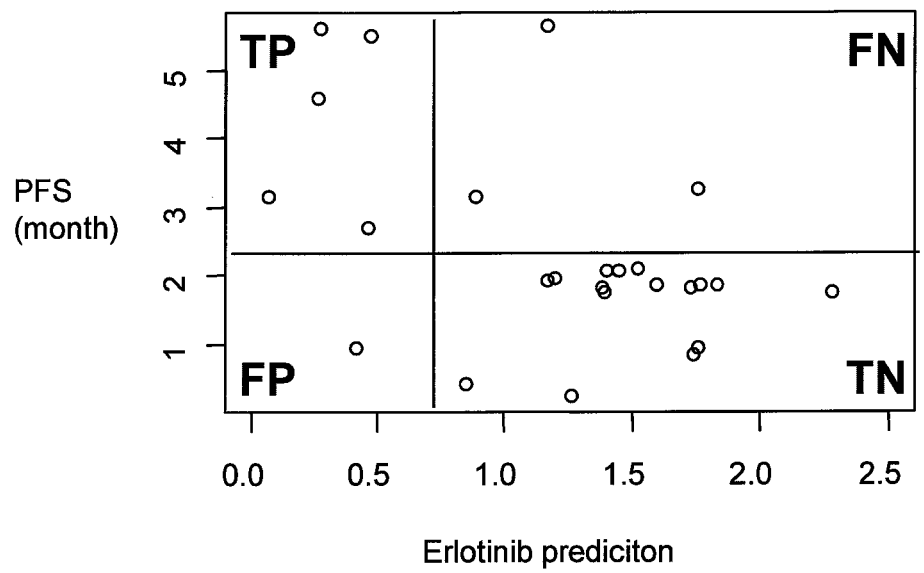

Erlotinib model predicts Erlotinib response. As shown in FIG. 7A, the Erlotinib model built from the cell line panel Erlotinib screen data (IC50s), using a 0.75 separation cutoff value, predicted patients' response for the Erlotinib treated patients. The Erlotinib model performance for accuracy, sensitivity, specificity, positive predictive value, and negative predictive value are 84%, 63%, 94%, 83% and 84%, respectively.

Sorafenib model predicts Sorafinib response. Similarly, the Sorafenib model built from cell line panel Sorafenib screen data (IC50s) can predict drug response for the 39 Sorafenib treated patients (FIG. 7B) using a 2.0 separation cutoff value. The Sorafenib model performance for accuracy, sensitivity, specificity, positive predictive value, and negative predictive value are 79%, 89%, 77%, 53% and 96%, respectively.

Erlotinib model does not predict Sorafenib response. The Erlotinib model was further tested to predict responses of Sorafenib treated patients. For this patient population with heavily pre-treatments in the BATTLE clinical trial, both the PFS and model predicted scores suggested that the majority of the patients are not Erlotinib sensitive. As a result, the overall accuracy of Erlotinb model in predicting Sorafenib treatment outcome was 64% with a cutoff of 0.75 (FIG. 7C), 49% with a cutoff of 0.5 (not shown). Interestingly, the Erlotinib model predicted four patients in the Sorafenib treated arm to be Erlotinib sensitive but none of them was actually sensitive to Sorafenib treatment, which corresponds to a positive predictive value of 0%. In comparison, when use Erlotinib model to predict Erlotinib treated patients' response, the positive predictive value was 83%.

Figure 7B:
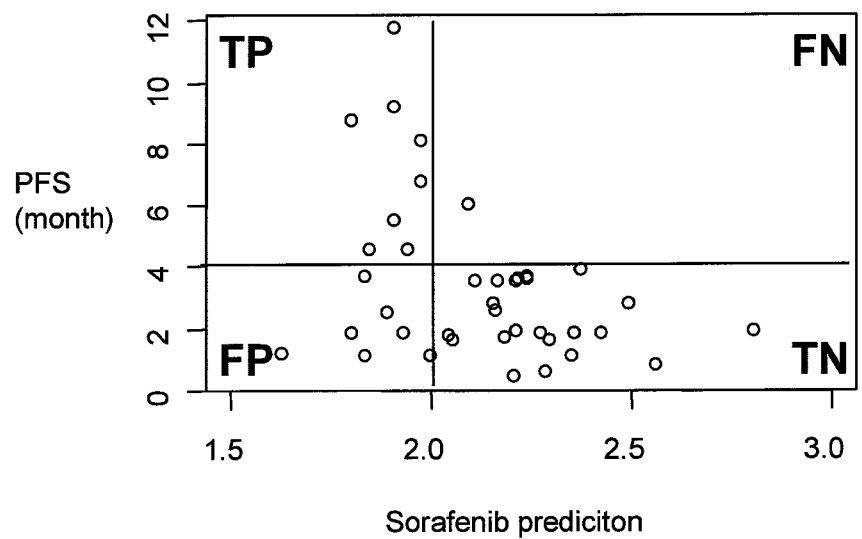
Figure 7C:
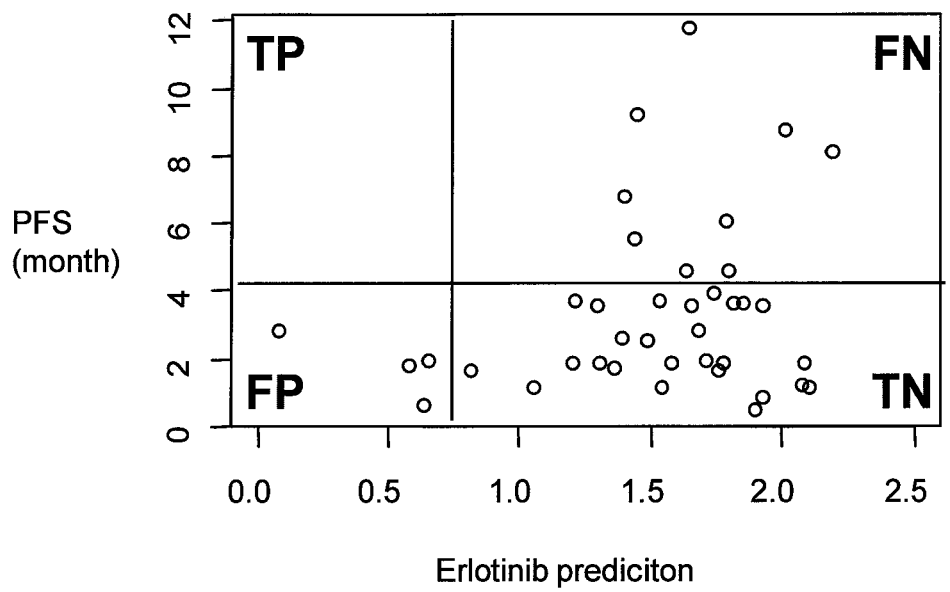
Figure 7D:
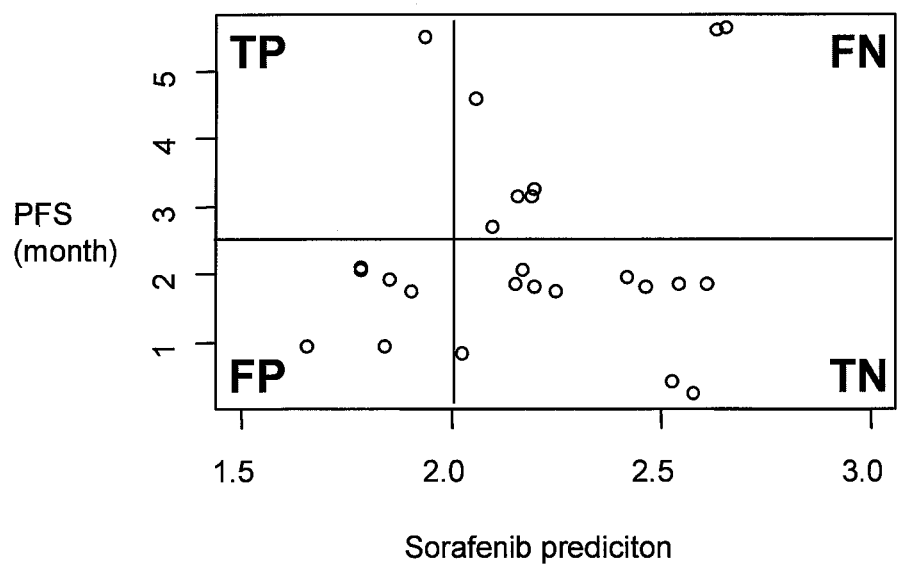

Sorafenib model does not predict Erlotinib response. Sorafenib model failed to predict BATTLE Erlotinib treated patients' response, with a positive predictive value of 14% and the overall accuracy using Sorafenib model to predict Erlotinib response of 48% (FIG. 7D). It was worth noting that even in case of using Sorafenib model to predict Sorafenib treated patients' response, the positive predictive value was only 53% (much lower that Erlotinb models 83%). On the other hand, the Sorafenib model had a very high negative predictive value at 96%, so that the overall model accuracy was 79% (only slightly lower than Erlotinib model's 84%).

Putting together, Erlotinib or Sorafenib models trained from cell line panel data can be used to predict well the corresponding treatment patient response. However, the models performed poorly in cross-evaluation (i.e. Sorafenib signature for predicting Erlotinib response and vice versa). This suggests that both Erlotinib and Sorafenib models are drug specific.

The signature genes on Erlotinib predictive model correctly captured Erlotinib mode of action (MOA) as an EGFR inhibitor. Moreover, the reconstructed signaling network for Erlotinib signature featured several highly expressed growth factors linked to Erlotinib resistance. Similarly, the network built for Sorafenib signature was also clearly linked to its MOA.

There are some cell line based signature generation works previously done in the field. For example, in one NCI-60 study, the "co-expression extrapolation" (COXEN) algorithm was developed for selecting the few genes expressed in sync between cell lines and primary tumors (Lee et al. (2007) Proc. Natl. Acad. Sci. USA 104:13086-13091); both tumor and cell lines expression patterns were used for deriving a multi-gene predictor. Lately, the COXEN algorithm was applied on 55-sample ovarian cancer patients using a cell line-trained multi-gene predictor (Ferriss et al. (2012) PloS one 7:e30550. One potential limitation for the COXEN algorithm was its feature selection approach: it did clustering analysis on both preclinical and clinical data to select input genes for model training. In the current work, our model was built entirely on cell line panel data, so the BATTLE clinical dataset can be used as an independent testing dataset.

The training and testing datasets and the end-points were obviously different: the models were built from a 2D in vitro cell line panel with IC50 curves as phenotype. The validation study was conducted on an expression dataset of primary tumors from BATTLE clinical trial with progress free survival (PFS) time used as the clinical end-point. Moreover, the training data (cell line panel) cover a mixture of cancer indications, while only non-small cell lung cancer (NSCLC) was the only indication in the BATTLE trial. The signatures were generated on the Affymetrix U133plus2 platform and tested on the data generated on Affymetrix Human Gene 1.0 ST platform. Such high discrepancy between experimental conditions commanded a careful consideration for the modeling approach and feature selection. Overall, the cell lines derived Erlotinib and Sorafenib sensitivity models predicted BATTLE trial PFS outcomes with high accuracy of 84% and 79%, respectively (FIGS. 7A and 7B).

Example 9

Testing the Erlotinib and Sorafenib Pathway-based Models for Predicting Survival Another way to assess cell line data derived drug sensitivity models was to test them for patient stratification. Patients in the BATTLE clinical trial were assigned to a marker positive (drug sensitive) or a marker negative (drug resistant) sub-group based on corresponding drug's predicted sensitivity scores, then marker +/− patient groups were compared based on the clinical output progression-free survival (PFS).

Figure 8A:
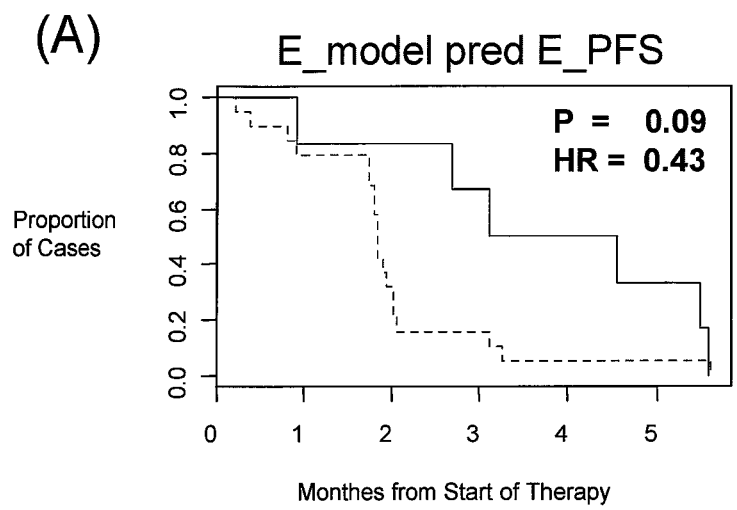
Figure 8B:
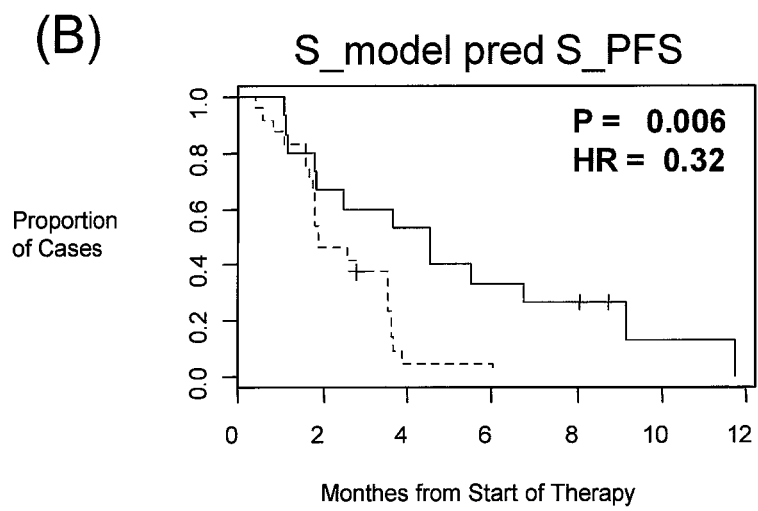

FIG. 8A shows that the Erlotinib PLSR signature was able to predict Erlotinib patient with longer PFS. The median PFS for the Erlotinib-sensitive patient group (solid line) was 3.84 month while the PFS for Erlotinib-resistant patients (dashed line) was 1.84 month, corresponding to a p-value of 0.09 and Hazard ratio of 0.43. The median PFS for all the patients in the BATTLE trial was 1.90 month, suggesting that Erlotinib model, indeed, selected the patient group with twice as long survival, and, therefore, clearly benefiting from Erlotinib treatment. Since all the patients in Erlotinb treatment arm were EGFR wild-type, it was not possible to use the EGFR mutation biomarker here. On the other hand, the current gene expression based biomarker works reasonably well on separating Erlotinib sensitive vs resistant patients.

When use Sorafenib model to stratify BATTLE patients in Sorafenib arms, the model-identified marker-sensitive group (solid line) had PFS 2.66 months survival benefit vs. marker-resistant group (dashed line) (FIG. 8B), with a p-value of 0.006 and a Hazard-ratio of 0.32. The median PFS survival was 4.53 and 1.87 months, for marker-sensitive and marker-insensitive groups, respectively. Sorafenib was not approved on Lung cancer. However, the phase III clinical trial which led to FDA approval on Kidney cancer observed a median survival benefit of 167 days vs. 84 days (Sorafenib vs. placebo), corresponding to 5.57 and 2.80 months (a 2.77 month PFS benefit).

Figure 8C:
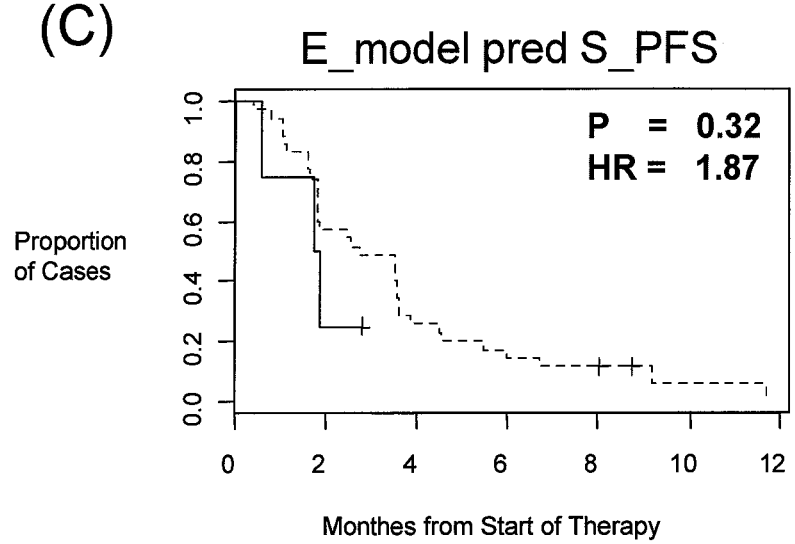
Figure 8D:
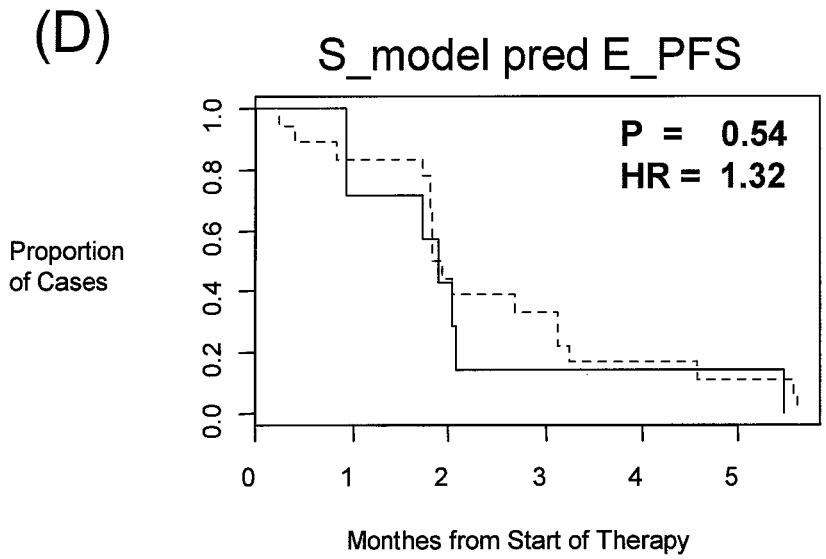

Importantly, the signatures were drug-specific and did not work across-arms. The Erlotinib predictive model failed to separate marker-sensitive vs. marker-insensitive groups for the Sorafenib treatment arm (p-value of 0.32 for separation of solid and dashed lines; FIG. 8C) and the Sorafenib model failed to distinguish the groups for the Erlotinib treatment arm (p-value of 0.54 for separation of solid and dashed lines; FIG. 8D). Neither signature conveyed survival benefit for marker-sensitive groups, suggesting that the predictive models are drug specific.

KRAS mutation is normally considered to be linked to anti-EGFR therapeutic responses in NSCLC patients (Langer (2011) P T 36:263-279), and KRAS mutation status is often collected on evaluating clinical outputs (Weickhardt et al (2012) J. Clin. Oncol. 30:1505-1512). The predictive power for survival was evaluated using either the PLSR generated signature or the KRAS mutation status, by grouping patients in the BATTLE trial then estimating the potential survival advantage using each biomarker.

Figure 8E:
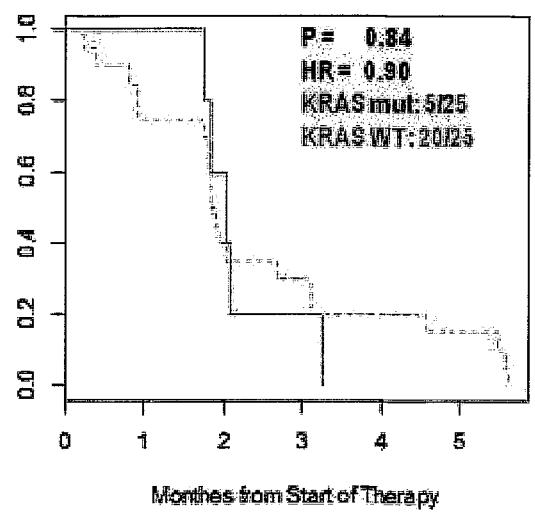

As shown in FIG. 8A, the 51 gene PLSR signature identified erlotinib-sensitive patients tended to respond well on erlotinib treatment with longer PFS—The p-value of 0.09 is not significant but it is most likely driven by small sample size (25 patients). On the other hand, KRAS mutation status provided little information on patients' survival after erlotinib treatment (p-value of 0.84 for separation of solid and dashed lines; FIG. 8E).

Given the fact the Erlotinib is an EGFR inhibitor while Sorafenib has multiple tyrosine kinase receptors as targets, one would expect that model specificity between Erlotinib and Sorafenib would be difficult to achieve. Strikingly, the Erlotinib and Sorafenib drug sensitivity models were drug specific, i.e. the Erlotinib model failed to predict Sorafenib patients' PFS and vice versa (FIGS. 7 and 8).

Example 10

Testing the MLN4924 Pathway-based Model on Melanoma Explant Response

Surgical specimens of human melanoma tumors were implanted subcutaneously into mice. After subsequent growth and passage in mice, tumors were excised and expanded into cohorts for treatment. Mice were treated subcutaneously with MLN4924 and the tumor growth was measured to identify sensitive and resistant tumors. Total RNA isolated from the melanoma explants (i.e., human tumor xenografts) was hybridized on an Affymetrix gene arrays.

To determine the ability of the MLN4924 pathway-based classifier to predict response of melanoma explants to MLN4924, some technical steps needed to be performed prior to the evaluation: The gene expression data from Example 1 was on Affymetrix U133plus2 platform, while the melanoma explant gene expression was generated on Affymetrix HuGene10stv1platform. Therefore, first the common genes needed to be found on these two platforms. (2). A quantile based normalization was applied, to adjust distribution of melanoma gene expression against that of the Example 1 cell lines (since the PLSR model is trained on Example 1 data). (3). Among the 69-gene signature we obtained from Example 1 dataset, there are 65 genes that also presented on the Melanoma dataset (BAG2, CD36, PTPRM and VCAN were missing). Therefore the MLN4924 PLSR model was retrained using the 65 genes, to get a predictive model that can be applied to melanoma dataset. (4). A cell line PLSR model derived cutoff was adopted to assign sensitive- or resistant-labels on predicted results, which were then compared to experimental data.

FIG. 9 shows the predicted vs experimental $\log_2(IC50)$ values on the Example 1 testing dataset, which was set aside in the training process to evaluate the modeling performance. The overall correlation coefficient between the predicted and experimental obtained $\log_2(IC50)$ values are 0.52, and a data driven cutoff to separate sensitive vs resistant cell lines is shown as the horizontal line at −1.45.

Adopting the model as well as the cutoff, predictions were made on the melanoma explants. Overall, the PLSR model made eight correct predictions out of the ten Melanoma explants, therefore 80% accuracy (shown in Table 7 below).

TABLE 7

Comparison between Prediction and Experimental Result on Melanoma Explant.

| Explant | Experimental Result with MLN4924 treatment | Prediction with Pathway-based classifier |
|---|---|---|
| 1 | Sensitive | Resistant |
| 2 | Sensitive | Sensitive |
| 3 | Sensitive | Resistant |
| 4 | Resistant | Resistant |
| 5 | Resistant | Resistant |
| 6 | Resistant | Resistant |
| 7 | Resistant | Resistant |
| 8 | Resistant | Resistant |
| 9 | Resistant | Resistant |
| 10 | Resistant | Resistant |

Similar to the erlotinib testing case, this example started from an in vitro cell line panel to build a PLSR predictive model. Although the model was built on mixtures of cancer indication cell line samples, it was used to predict within cancer indication tumor/patient samples. Most importantly, the model was built on in vitro data, while it was used to predict in vivo drug response.

Example 11

Comparisons with Xenograft Models of MLN4924 Treatment

The MLN4924 PLSR model described herein was generated based on the behavior of cells grown and treated in vitro with MLN4924. The ability of in vitro cell line inhibition results to predict in vivo treatment results was compared to PLSR model prediction of in vivo treatment results.

Tumor models were grown both in vitro and in vivo as xenografts in rats or mice. Treatment with MLN4924 generated cell viability data for in vitro cultures and pharmacokinetic exposure relationships in xenograft subjects. Gene expression information was obtained from xenograft samples of tumor cells from untreated or vehicle-treated animals, normalized on the Affymetrix array.

In general, for xenograft studies, tumor cell lines are prepared for injection after growth in culture and primary human tumors are prepared for implantation as tumor fragments. Xenografts typically are subcutaneously injected or implanted, respectively, and grown to a certain size before commencing treatment. Growth of xenografts is monitored by measuring tumor volume. Plasma concentration of MLN4924 at various dose levels (i.e., 10, 30, 60, 90 mg/kg) was determined and used to generate a PK model. Total MLN4924 exposure (AUC) delivered in each study group was calculated using the PK model.

A variety of studies with various in vivo tumor formats, doses, dosing schedules and tumor inhibition activity of MLN4924 were compiled for each tumor type. As a result of this variety, a method was needed to compare the relative sensitivity of the tumor types. An analysis in multiple tumor types showed that the antitumor activity was related to the total exposure or AUC of MLN4924 during the study. Normalized tumor growth rates (G) were computed for each treatment arm in the antitumor activity studies, and data points were fitted to the equation $G_{treat}/G_{control}=1+$Slope*AUC. Using this method, an average plasma concentration needed during the inhibitory activity study to reach tumor stasis was obtained for each xenograft model, with a range of coefficient of variance percentages (CV %). Table 8 provides the results of the compilation. To simplify the comparisons, Table 8 ranks the tumor types by overall xenograft sensitivity to MLN4924 (rank of 1 is most sensitive, 16 is least sensitive).

TABLE 8

Compilation of MLN4924 treatment of xenograft models

| Name | Type | C avg at stasis (µg/ml) | CV % | Sensitivity Rank |
|---|---|---|---|---|
| HCT116 (grown in rat) | colorectal carcinoma | 1.490 | 5.914 | 1 |
| HCT116 (grown in mouse) | colorectal carcinoma | 1.983 | 3.803 | 2 |
| HL-60 | promyelocytic leukemia | 2.023 | 4.520 | 3 |
| PHTX-02B | Breast cancer | 3.691 | 10.285 | 4 |
| NCI-H82 | small cell lung cancer | 5.316 | 7.504 | 5 |
| PC3 | prostate cancer | 5.968 | 15.144 | 6 |
| A375 | melanoma | 6.837 | 11.075 | 7 |
| NCI-H69 | small cell lung cancer | 6.868 | 8.905 | 8 |
| HT29 | colon adenocarcinoma | 7.171 | 11.862 | 9 |
| PHTX-50M | melanoma | 8.501 | 13.669 | 10 |
| DU-145 | prostate cancer | 9.365 | 15.277 | 11 |
| SKOV3 | ovarian carcinoma | 9.890 | 16.657 | 12 |
| PHTX-51M | melanoma | 11.588 | 4.828 | 13 |
| NCI-H322M | non-small cell lung carcinoma | 14.722 | 18.601 | 14 |
| NCI-H460 | non-small cell lung carcinoma | 17.070 | 8.872 | 15 |
| DLD-1 | colon adenocarcinoma | 17.476 | 16.220 | 16 |

FIG. 10A shows the comparison of the ability (expressed as log$_2$(IC50)) of MLN4924 to inhibit the xenograft with the same tumor in culture (where culture data were available). FIG. 10B shows the comparison of the ability (expressed as log$_2$(IC50)) of MLN4924 to inhibit the xenograft with the prediction using the expression of the markers of Table 1.

Example 12

Isolation of Nucleic Acid and Nucleic Acid Sequencing Methods

Genomic Isolations and DNA Sequencing. DNA isolation from cells and tumors is conducted using DNAEASY® isolation kit (Qiagen, Valencia, Calif.). RNA isolation is conducted using MegaMax (Ambion division of Applied Biosystems, Austin, Tex.). Genomic isolations are conducted following manufacturer recommend protocols.

SANGER Sequencing Methodology. PCR amplifications are conducted using optimized cycling conditions per gene-exon. Primer extension sequencing is performed using Applied Biosystems BigDye version 3.1. The reactions are then run on Applied Biosystem's 3730xl DNA Analyzer. Sequencing base calls are done using KB™ Basecaller (Applied Biosystems). Somatic Mutation calls are determined by Mutation Surveyor (SoftGenetics) and confirmed manually by aligning sequencing data with the corresponding reference sequence using Seqman (DNASTAR).

SEQUENOM Sequencing Methodology. Sequenom (San Diego, Calif.) assays are designed using TypePLEX® chemistry with single-base extension. This process consists of three steps: 1) A text file containing the SNPs or mutations of interest and flanking sequence is uploaded at mysequenom.com where it is run through a web based program ProxSNP, 2) The output of ProxSNP is run through PreXTEND and 3) the output of PreXTEND is run through Assay Design which determines the expected mass weight of the extend products to ensure separation between all potential peaks found within a multiplexed reaction.

PCR primers are then designed to bracket the region identified in the assay design steps. The region of interest is amplified in PCR reactions using the primers. 15 nl of amplified and extended product is spotted on a 384 SpectroCHIP II using a Nanodispenser RS1000. A 3-point calibrant is added to every chip to ensure proper performance of the Sequenom Maldi-tof compact mass spectrometer.

The SpectroCHIP II is placed in the Sequenom MALDI-TOF compact mass spectrometer. The mass spectrometer is set to fire a maximum of 9 acquisitions for each spot on the 384 well spectroCHIP. TypePLEX Gold kit SpectroCHIP II from Sequenom (10142-2) is used following manufacturers recommended protocols. Analysis is performed using Sequenom analysis software, MassARRAY® Typer Analyzer v4.

NEXT GENERATION SEQUENCING (NGS) methodology. Targeted NGS using the Illumina platform (Illumina, Inc. San Diego, Calif.) is used to confirm and identify low frequency mutations in a marker. Primer pairs are designed to amplify coding exons. PCR products are quantified using a PicoGreen assay and combined in equal molar ratios for each sample. The purified products are end-repaired and concatenated by ligation. The concatenated products are used for Hi-Seq 2000 library preparation. The concatenated PCR products are sheared and used to make barcoded Hi-Seq 2000 libraries consisting of 12 barcoded samples per multiplexed pool. The pooled Hi-Seq 2000 libraries undergo clonal amplification by cluster generation on eight lanes of a Hi-Seq 2000 flow cell and are sequenced using 1×100 single-end sequencing on a Hi-Seq 2000. Matching of primary sequencing reads to the human genome build Hg18, as well as SNP analysis are performed using Illumina's CASAVA software version 1.7.1.

General Procedures
Quantitative RT-PCR cDNA synthesis and quantitative RT-PCR is performed using ABI Gene Expression Assays, reagents, and ABI PRISM® 7900HT Sequence Detection Systems (Applied Biosystems, Foster City, Calif.) using the following cycle conditions: hold at 50° C. for 2 minutes for AmpErase UNG activation, then 95.0° C. for 10 minutes to activate DNA polymerase then run 40 two-part cycles of 95.0° C. for 15 seconds and 60.0° C. for 1 minute. The dCt is calculated by using the average Ct of control genes B2M (Hs99999907_m1) and RPLPO (Hs99999902_m1). Relative mRNA expression quantification is derived using the Comparative Ct Method (Applied Biosystems). mRNA expression fold change values are generated from a normal sample and corresponding tumor sample.

Sample Handling for Myeloma Samples

Upon collection of patient bone marrow aspirate, the myeloma cells are enriched via rapid negative selection. The enrichment procedure employs a cocktail of cell-type specific antibodies coupled with an antibody that binds red blood cells RosetteSep (Stem Cell Technologies). The antibody cocktail has antibodies with the following specificity: CD14 (monocytes), CD2 (T and NK cells), CD33 (myeloid progenitors and monocytes), CD41 (platelets and megakaryocytes), CD45RA (naïve B and T cells) and CD66b (granulocytes). The antibodies cross-link the non-myeloma cell types to the red blood cells in the samples. The bound cell types are removed using a modified ficoll density gradient. Myeloma cells are then collected and frozen.

Total RNA is isolated using a QIAGEN® Group RNEASY® isolation kit (Valencia, Calif.) and quantified by spectrophotometry.

DNA is isolated from the flow through fraction of the column used in the RNA isolation method.

EQUIVALENTS

Although embodiments of the invention have been described using specific terms, such description are for illustrative purposes only, and it is to be understood that changes and variations may be made without departing from the spirit or scope of the invention. Those skilled in the art will recognize, or be able to ascertain using no more than routine experimentation, many equivalents of the specific embodiments of the invention described herein. Such equivalents are intended to be encompassed by the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10662477B2). An electronic copy of the "Sequence Listing" will also be available from the USPTO upon request and payment of the fee set forth in 37 CFR 1.19(b)(3).

What is claimed is:

1. A method of treating a patient having cancer, the method comprising administering an NAE inhibitor that is ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulphamate or a pharmaceutically acceptable salt thereof to a patient having a marker gene set consisting of markers 1-3 and 5-45 of Table 1, wherein sensitivity of the patient's cancer to the NAE inhibitor is determined using a partial least squares regression (PLSR)-based algorithm to generate a predictive outcome score based on the gene expression levels of the gene markers and comparing the predictive outcome score to a cutoff value.

2. The method of claim 1, wherein the gene markers comprises at least one marker in a pathway selected from the group consisting of TGFbeta-SMAD signaling pathway, adhesion receptor-induced signaling pathway, c-myc transcription factor pathway and c-myb transcription factor pathway.

3. The method of claim 1, wherein the cancer is a hematological cancer or a solid tumor cancer.

4. The method of claim 3, wherein the solid tumor cancer is selected from the group consisting of skin cancer, breast cancer, colon cancer, lung cancer, pancreatic cancer, esophageal cancer, bladder cancer, and head and neck cancer.

5. The method of claim 3, wherein the hematological cancer is selected from the group consisting of myeloma, leukemia, lymphoma, and myelodysplastic syndrome.

6. The method of claim 3, wherein the hematological cancer is selected from the group consisting of multiple myeloma, Waldenstrom's syndrome, chronic lymphocytic leukemia, acute myelogenous leukemia, chronic myelogenous leukemia, B-cell lymphomas, monocytic leukemia, or non-Hodgkin's lymphoma.

7. The method of claim 1, wherein the pharmaceutically acceptable salt is a hydrochloride salt.

8. The method of claim 1, wherein the cutoff value is a separation cutoff value.

9. The method of claim 1, wherein the predictive outcome score is expressed in terms of $\log_2(IC50)$ of the NAE inhibitor.

10. The method of claim 9, wherein the $\log_2(IC50)$ has a cutoff value range of −3 to 1.0.

11. The method of claim 1, wherein a predictive outcome score below the cutoff value indicates sensitivity to the NAE inhibitor.

12. A method of treating a patient having cancer, the method comprising administering an NAE inhibitor that is ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulphamate or a pharmaceutically acceptable salt thereof to a patient having a marker gene set comprising at least one gene marker selected from the group consisting of markers 1, 2, 3 and 4 identified in Table 1, wherein sensitivity of the patient's cancer to the NAE inhibitor is determined using a partial least squares regression (PLSR)-based algorithm to generate a predictive outcome score based on the gene expression levels of the at least one gene marker and comparing the predictive outcome score to a cutoff value.

13. The method of claim 12, wherein the patient has at least one additional gene marker selected from the group consisting of marker 46, marker 47, or both marker 46 and marker 47 identified in Table 1.

14. The method of claim 13, wherein the at least one gene marker comprises at least one marker in a pathway selected from the group consisting of TGFbeta-SMAD signaling pathway, adhesion receptor-induced signaling pathway, c-myc transcription factor pathway and c-myb transcription factor pathway.

15. The method of claim 12, wherein the cancer is a hematological cancer or a solid tumor cancer.

16. The method of claim 15, wherein the solid tumor cancer is selected from the group consisting of skin cancer, breast cancer, colon cancer, lung cancer, pancreatic cancer, esophageal cancer, bladder cancer, and head and neck cancer.

17. The method of claim 15, wherein the hematological cancer is selected from the group consisting of myeloma, leukemia, lymphoma, and myelodysplastic syndrome.

18. The method of claim 15, wherein the hematological cancer is selected from the group consisting of multiple myeloma, Waldenstrom's syndrome, chronic lymphocytic leukemia, acute myelogenous leukemia, chronic myelogenous leukemia, B-cell lymphomas, monocytic leukemia, or non-Hodgkin's lymphoma.

19. The method of claim 12, wherein the marker gene set consists of markers 1-3 and 5-45 of Table 1.

20. The method of claim 12, wherein the marker gene set consists of the markers 1-69 of Table 1.

21. The method of claim 12, wherein the cutoff value is a separation cutoff value.

22. The method of claim 12, wherein the predictive outcome score is expressed in terms of $\log_2(IC50)$ of the NAE inhibitor.

23. The method of claim 22, wherein the $\log_2(IC50)$ has a cutoff value range of −3 to 1.0.

24. The method of claim 22, wherein a predictive outcome score below the cutoff value indicates sensitivity to the NAE inhibitor.

25. The method of claim 12, wherein the pharmaceutically acceptable salt is a hydrochloride salt.

26. A method of treating a patient having cancer, the method comprising administering an NAE inhibitor that is ((1S,2S,4R)-4-{4-[(1S)-2,3-dihydro-1H-inden-1-ylamino]-7H-pyrrolo[2,3-d]pyrimidin-7-yl}-2-hydroxycyclopentyl)

methyl sulphamate or a pharmaceutically acceptable salt thereof to a patient having a marker gene set consisting of markers 1-69 of Table 1, wherein sensitivity of the patient's cancer to the NAE inhibitor is determined using a partial least squares regression (PLSR)-based algorithm to generate a predictive outcome score based on the gene expression levels of the gene markers and comparing the predictive outcome score to a cutoff value.

* * * * *